US010435336B2

(12) United States Patent
Kreischer et al.

(10) Patent No.: US 10,435,336 B2
(45) Date of Patent: Oct. 8, 2019

(54) OLEFIN COMPOSITIONS

(71) Applicant: Chevron Phillips Chemical Company LP, The Woodlands, TX (US)

(72) Inventors: Bruce E. Kreischer, Humble, TX (US); Ronald D. Knudsen, Saratoga Springs, UT (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 15/864,924

(22) Filed: Jan. 8, 2018

(65) Prior Publication Data
US 2018/0127332 A1 May 10, 2018

Related U.S. Application Data

(63) Continuation of application No. PCT/US2016/037581, filed on Jun. 15, 2016.

(30) Foreign Application Priority Data

Jul. 14, 2015 (WO) ............... PCT/US2015/040433

(51) Int. Cl.
*C07C 11/02* (2006.01)
*C07C 2/34* (2006.01)
*C07C 2/88* (2006.01)

(52) U.S. Cl.
CPC .............. *C07C 2/34* (2013.01); *C07C 2/88* (2013.01); *C07C 11/02* (2013.01); *C07C 2531/14* (2013.01); *C07C 2531/18* (2013.01); *C07C 2531/22* (2013.01)

(58) Field of Classification Search
CPC ............. C07C 2/26; C07C 11/02; C07C 2/08
See application file for complete search history.

(56) References Cited

U.S. PATENT DOCUMENTS

| 5,198,563 | A | 3/1993 | Reagen et al. |
| 5,288,823 | A | 2/1994 | Reagen et al. |
| 5,331,104 | A | 7/1994 | Reagen et al. |
| 5,340,785 | A | 8/1994 | Reagen et al. |
| 5,360,879 | A | 11/1994 | Reagen et al. |
| 5,376,612 | A | 12/1994 | Reagen et al. |
| 5,382,738 | A | 1/1995 | Reagen et al. |
| 5,399,539 | A | 3/1995 | Reagen et al. |
| 5,438,027 | A | 8/1995 | Reagen et al. |
| 5,470,926 | A | 11/1995 | Reagen et al. |
| 5,523,507 | A | 6/1996 | Reagen et al. |
| 5,543,375 | A | 8/1996 | Lashier et al. |
| 5,563,312 | A | 10/1996 | Knudsen et al. |
| 5,689,028 | A | 11/1997 | Lashier et al. |
| 5,750,816 | A | 5/1998 | Araki et al. |
| 5,763,723 | A | 6/1998 | Reagen et al. |
| 5,814,575 | A | 9/1998 | Reagen et al. |
| 5,856,257 | A | 1/1999 | Freeman et al. |
| 5,856,612 | A | 1/1999 | Araki et al. |
| 5,859,303 | A | 1/1999 | Lashier |
| 5,910,619 | A | 6/1999 | Urata et al. |
| 6,133,495 | A | 10/2000 | Urata et al. |
| 6,380,451 | B1 | 4/2002 | Kreischer et al. |
| 6,455,648 | B1 | 9/2002 | Freeman et al. |
| 6,844,290 | B1* | 1/2005 | Maas ............... B01J 31/143 502/103 |
| 7,157,612 | B2 | 1/2007 | Ewert et al. |
| 7,285,607 | B2 | 10/2007 | Blann et al. |
| 7,297,832 | B2 | 11/2007 | Blann et al. |
| 7,323,524 | B2 | 1/2008 | Blann et al. |

(Continued)

FOREIGN PATENT DOCUMENTS

| CN | 103100419 A | 5/2013 |
| EP | 608447 A1 | 8/1994 |
| EP | 706983 A1 | 4/1996 |
| EP | 3322680 A0 | 5/2018 |
| WO | 0147839 A1 | 7/2001 |
| WO | 2013013300 A1 | 1/2013 |
| WO | 2014094114 A1 | 6/2014 |
| WO | 2015094207 A1 | 6/2015 |
| WO | 2017010998 A1 | 1/2017 |
| WO | 2017011127 A1 | 1/2017 |

OTHER PUBLICATIONS

Deckers, Patrick J. W., et al., "Catalytic Trimerization of Ethene with Highly Active Cyclopentadienyl-Arene Titanium Catalysts," Organometallics, 2002, vol. 21, pp. 5122-5135, American Chemical Society.
Do, Loi H., et al., "Mechanistic Studies of Ethylene and α-Olefin Co-Oligomerization Catalyzed by Chromium-PNP Complexes," Organometallics, 2012, vol. 31, pp. 5143-4149, American Chemical Society.
Foreign communication from a related counterpart application—International Search Report and Written Opinion, PCT/US2015/040433, dated Feb. 23, 2016, 15 pages.
Foreign communication from a related counterpart application—International Search Report and Written Opinion, PCT/US2016/037581, dated Aug. 23, 2016, 13 pages.
McNaught, Alan D., et al., "Compendium of Chemical Terminology," IUPAC Recommendations, Second edition, 1997, 5 pages, Wiley-Blackwell.

(Continued)

Primary Examiner — Ellen M McAvoy
(74) Attorney, Agent, or Firm — Conley Rose, P.C.

(57) ABSTRACT

A composition comprising: a) at least 76 mol % $C_{10}$ monoolefins, the $C_{10}$ monoolefins comprising i) at least 3 mol % 2-butyl-1-hexene, ii) at least 8 mol % 3-propyl-1-heptene, iii) at least 6 mol % 4-ethyl-1-octene, and iv) at least 20 mol % 5-methyl-1-nonene; and b) at least 1 mol % $C_{14}$ monoolefins. A composition comprising at least 95 mol % $C_{10}$ monoolefins, the $C_{10}$ monoolefins comprising i) at least 3 mol % 2-butyl-1-hexene, ii) at least 10 mol % 3-propyl-1-heptene, iii) at least 7 mol % 4-ethyl-1-octene, and iv) at least 24 mol % 5-methyl-1-nonene. Processes to prepare a composition comprising at least 76 mol % $C_{10}$ monoolefins and at least 1 mol % $C_{14}$ monoolefins, or a composition comprising at least 95 mol % $C_{10}$ monoolefins, where the $C_{10}$ monoolefins comprise i) at least 3 mol % 2-butyl-1-hexene, ii) at least 10 mol % 3-propyl-1-heptene, iii) at least 7 mol % 4-ethyl-1-octene, and iv) at least 24 mol % 5-methyl-1-nonene.

20 Claims, No Drawings

(56) References Cited

U.S. PATENT DOCUMENTS

| | | | |
|---|---|---|---|
| 7,378,537 | B2 | 5/2008 | Small et al. |
| 7,384,886 | B2 | 6/2008 | Knudsen et al. |
| 7,476,775 | B2 | 1/2009 | Kreischer |
| 7,511,183 | B2 | 3/2009 | Blann et al. |
| 7,525,009 | B2 | 4/2009 | Blann et al. |
| 7,718,838 | B2 | 5/2010 | Woodard et al. |
| 7,820,581 | B2 | 10/2010 | Knudsen et al. |
| 7,829,749 | B2 | 11/2010 | Gao et al. |
| 7,906,681 | B2 | 3/2011 | Gao et al. |
| 7,910,670 | B2 | 3/2011 | Knudsen et al. |
| 7,964,763 | B2 | 6/2011 | Dixon et al. |
| 7,994,363 | B2 | 8/2011 | Gao et al. |
| 8,049,052 | B2 | 11/2011 | Kreischer et al. |
| 8,076,523 | B2* | 12/2011 | Bollmann ............... B01J 31/16 585/502 |
| 8,076,524 | B2* | 12/2011 | Lattner ................... C07C 2/32 585/502 |
| 8,134,038 | B2 | 3/2012 | McGuinness et al. |
| 8,211,949 | B2 | 7/2012 | Varineau et al. |
| 8,252,874 | B2* | 8/2012 | De Boer ............. B01J 31/0265 502/167 |
| 8,252,955 | B2 | 8/2012 | Gao et al. |
| 8,252,956 | B2 | 8/2012 | Gao et al. |
| 8,268,941 | B2 | 9/2012 | Kleingeld et al. |
| 8,329,608 | B2 | 12/2012 | Knudsen et al. |
| 8,334,420 | B2 | 12/2012 | Small et al. |
| 8,344,198 | B2 | 1/2013 | Ewert et al. |
| 8,367,786 | B2 | 2/2013 | Dixon et al. |
| 8,461,406 | B2 | 6/2013 | Overett et al. |
| 8,471,085 | B2 | 6/2013 | Sydora |
| 8,680,003 | B2 | 3/2014 | Sydora et al. |
| 8,865,610 | B2 | 10/2014 | Sydora et al. |
| 9,283,555 | B2 | 3/2016 | Sydora et al. |
| 9,328,297 | B1* | 5/2016 | Nyce ..................... C10G 50/00 |
| 9,732,106 | B2 | 8/2017 | Sydora et al. |
| 2005/0187391 | A1 | 8/2005 | Knudsen et al. |
| 2007/0185357 | A1* | 8/2007 | De Boer ............... B01J 31/143 585/511 |
| 2009/0306442 | A1 | 12/2009 | Pretorius et al. |
| 2010/0036185 | A1 | 2/2010 | Yokoyama et al. |
| 2010/0113257 | A1 | 5/2010 | Kreischer et al. |
| 2010/0113851 | A1 | 5/2010 | Kreischer et al. |
| 2010/0113852 | A1 | 5/2010 | Sydora |
| 2010/0274065 | A1 | 10/2010 | Sydora |
| 2010/0331503 | A1 | 12/2010 | Emoto et al. |
| 2011/0257350 | A1 | 10/2011 | Jaber et al. |
| 2011/0282016 | A1 | 11/2011 | Carter et al. |
| 2012/0041241 | A1 | 2/2012 | Ewart et al. |
| 2012/0088933 | A1 | 4/2012 | Carter et al. |
| 2012/0101321 | A1 | 4/2012 | Brown et al. |
| 2012/0142989 | A1 | 6/2012 | Jaber et al. |
| 2012/0199467 | A1 | 8/2012 | Gildenhuys et al. |
| 2012/0271087 | A1 | 10/2012 | Brown et al. |
| 2012/0316303 | A1 | 12/2012 | Hanton et al. |
| 2013/0150605 | A1 | 6/2013 | Sydora et al. |
| 2013/0150642 | A1 | 6/2013 | Sydora et al. |
| 2013/0331629 | A1 | 12/2013 | Sydora et al. |
| 2015/0232395 | A1* | 8/2015 | Nyce ..................... C07C 2/84 518/705 |
| 2015/0284303 | A1* | 10/2015 | Zoricak .................. C07C 2/36 585/522 |
| 2015/0299069 | A1* | 10/2015 | Azam ..................... C07C 2/36 585/513 |
| 2018/0016204 | A1* | 1/2018 | Coffin ................... C07C 2/08 |

OTHER PUBLICATIONS

Periodic Table of Elements, Feb. 4, 1985, C&EN, p. 27.

Suzuki, Yasuhiko, et al., "Trimerization of Ethylene to 1-Hexene with Titanium Complexes Bearing Phenoxy-Imine Ligands with Pendant Donors Combined with MAO," Organometallics, 2010, vol. 29, pp. 2394-2396, American Chemical Society.

Zhou, Yong, et al., "Structural Analysis of Isomers in Commercial α-Olefins with 13C NMR Spectroscopy," Petroleum Processing and Petrochemical, 2005, vol. 36, No. 5, pp. 51-56.

Zilbershtein, Timur M., et al., "Decene Formation in Ethylene Trimerization Reaction Catalyzed by Cr-Pyrrole System," Applied Cat A: Gen, 2014, vol. 475, pp. 371-378, Elsevier B.V.

Foreign Communication from a related counterpart application—European Examination Report, Application No. 16736305.0, dated Feb. 13, 2019, 6 pages.

* cited by examiner

OLEFIN COMPOSITIONS

CROSS-REFERENCE TO RELATED APPLICATIONS

This application is a continuation application of International Application No. PCT/US2016/037581 filed Jun. 15, 2016, published as WO 2017/011127A1, which claims the benefit of and priority to International Application No. PCT/US2015/040433 filed Jul. 14, 2015 in the U.S. Receiving Office, published as WO 2017/010998A1, both entitled "Olefin Compositions," each of which is incorporated by reference herein in its entirety.

TECHNICAL FIELD OF THE INVENTION

The present disclosure relates to compositions containing decene isomers and methods of making same. More specifically, the present disclosure relates to compositions containing decene isomers produced in an ethylene oligomerization process.

BACKGROUND OF THE INVENTION

Olefins, such as decenes, can be used for manufacturing a variety of products, or as a fuel source. Commercial 1-decene has many potential uses and 1-decene demand can often out-pace 1-decene supply. However, many applications may not require a feedstock having a high 1-decene content and compositions containing a mixture of decene isomers can be utilized in particular applications depending upon the quantity and identity of the components found in the compositions containing the decene isomers. Thus, there is a need to develop and identify sources which can provide compositions containing decene isomers.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Embodiments disclosed and described herein are directed to a composition comprising a) at least 76 mol % $C_{10}$ monoolefins, the $C_{10}$ monoolefins comprising i) at least 3 mol % 2-butyl-1-hexene, ii) at least 8 mol % 3-propyl-1-heptene, iii) at least 6 mol % 4-ethyl-1-octene, and iv) at least 20 mol % 5-methyl-1-nonene; and b) at least 1 mol % $C_{14}$ monoolefins. Other embodiments disclosed and described herein are directed to a composition comprising at least 95 mol % $C_{10}$ monoolefins, the $C_{10}$ monoolefins comprising i) at least 3 mol % 2-butyl-1-hexene, ii) at least 10 mol % 3-propyl-1-heptene, iii) at least 7 mol % 4-ethyl-1-octene, and iv) at least 24 mol % 5-methyl-1-nonene.

Further embodiments disclosed and described herein are directed to a process comprising a) contacting 1) ethylene, 2) a catalyst system comprising i) a chromium containing compound, ii) a heteroatomic ligand, and iii) an alkylaluminum compound, and 3) optionally a reaction system diluent, b) forming an oligomer product comprising 1-hexene and/or 1-octene in a reaction system, c) discharging a reaction system effluent from the reaction system; d) contacting the reaction system effluent with a catalyst system deactivating agent; and e) isolating a first composition comprising (1) at least 76 mol % $C_{10}$ monoolefins, the $C_{10}$ monoolefins comprising (i) at least 3 mol % 2-butyl-1-hexene, (ii) at least 8 mol % 3-propyl-1-heptene, (iii) at least 6 mol % 4-ethyl-1-octene, and (iv) at least 20 mol % 5-methyl-1-nonene, and (2) at least 1 mol % $C_{14}$ monoolefins.

DETAILED DESCRIPTION OF THE INVENTION

Disclosed herein are compositions comprising at least 76 mol % $C_{10}$ monoolefins. Also disclosed herein are compositions comprising at least 95 mol % $C_{10}$ monoolefins. In an embodiment, a process for producing a $C_{10}$ monoolefins composition can comprise (a) contacting 1) ethylene, 2) a catalyst system comprising i) a chromium containing compound, ii) a heteroatomic ligand, and iii) a metal alkyl compound, and 3) optionally a reaction system diluent; (b) forming an oligomer product comprising 1-hexene and/or 1-octene in a reaction system; (c) discharging a reaction system effluent from the reaction system; (d) contacting the reaction system effluent with a catalyst system deactivating agent; and (e) isolating a first composition comprising at least 76 mol % $C_{10}$ monoolefins. In some embodiments, the process can comprise isolating a second composition comprising at least 95 mol % $C_{10}$ monoolefins. In other embodiments, the process can comprise recovering a second composition comprising at least 95 mol % $C_{10}$ monoolefins from the first composition comprising at least 76 mol % $C_{10}$ monoolefins.

To define more clearly the terms used herein, the following definitions are provided. Unless otherwise indicated, the following definitions are applicable to this disclosure. If a term is used in this disclosure, but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Groups of elements of the Periodic Table are indicated using the numbering scheme indicated in the version of the Periodic Table of elements published in Chemical and Engineering News, 63(5), 27, 1985. In some instances, a group of elements can be indicated using a common name assigned to the group; for example, alkali metals for Group 1 elements, alkaline earth metals (or alkaline metals) for Group 2 elements, transition metals for Groups 3-12 elements, and halogens for Group 17 elements.

Regarding claim transitional terms or phrases, the transitional term "comprising", which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. The term "consisting essentially of" occupies a middle ground between closed terms like "consisting of" and fully open terms like "comprising." Absent an indication to the contrary, when describing a compound or composition, "consisting essentially of" is not to be construed as "comprising," but is intended to describe the recited component that includes materials which do not significantly alter the composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class to which is utilized and it is possible to have different transitional terms or phrases utilized with different features within a claim. For example, a method can comprise several recited steps (and other non-recited steps), but utilize a catalyst system preparation consisting of specific steps, or alternatively, consisting essentially of specific steps, but utilize a catalyst system comprising recited components and other non-recited components.

While compositions and methods are described in terms of "comprising" (or other broad term) various components and/or steps, the compositions and methods can also be described using narrower terms, such as "consist essentially of" or "consist of" the various components and/or steps.

The terms "a," "an," and "the" are intended, unless specifically indicated otherwise, to include plural alternatives, e.g., at least one. For instance, the disclosure of "a trialkylaluminum compound" is meant to encompass one trialkylaluminum compound, or mixtures or combinations of more than one trialkylaluminum compound, unless otherwise specified.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers, unless explicitly indicated otherwise; e.g., a general reference to pentane includes n-pentane, 2-methyl-butane, and 2,2-dimethylpropane, while a general reference to a butyl group includes an n-butyl group, a sec-butyl group, an iso-butyl group, and a tert-butyl group. Additionally, the reference to a general structure or name encompasses all enantiomers, diastereomers, and other optical isomers, whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner. By way of example, an "alkyl group" can formally be derived by removing one hydrogen atom from an alkane, while an "alkylene group" can formally be derived by removing two hydrogen atoms from an alkane. Moreover, a more general term can be used to encompass a variety of groups that formally are derived by removing any number ("one or more") of hydrogen atoms from a parent compound, which in this example can be described as an "alkane group," and which encompasses an "alkyl group," an "alkylene group," and materials having three or more hydrogens atoms, as necessary for the situation, removed from the alkane. Throughout the disclosure of a substituent, ligand, or other chemical moiety that can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedures, unless specified otherwise or the context requires otherwise.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from one or two carbon atoms of an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, phosphines, and so forth. In one aspect, the hydrogen atom(s) removed to form the "organyl group," "organylene group," or "organic group" can be attached to a carbon atom belonging to a functional group, for example, an acyl group (—C(O)R), a formyl group (—C(O)H), a carboxy group (—C(O)OH), a hydrocarboxycarbonyl group (—C(O)OR), a cyano group (—C≡N), a carbamoyl group (—C(O)NH$_2$), an N-hydrocarbylcarbamoyl group (—C(O)NHR), or an N,N'-dihydrocarbylcarbamoyl group (—C(O)NR$_2$), among other possibilities. In another aspect, the hydrogen atom(s) removed to form the "organyl group," "organylene group," or "organic group" can be attached to a carbon atom not belonging to, and remote from, a functional group, for example, —CH$_2$C(O)CH$_3$, —CH$_2$NR$_2$, and the like. An "organyl group," "organylene group," or "organic group" can be aliphatic, inclusive of being cyclic or acyclic, or can be aromatic. "Organyl groups," "organylene groups," and "organic groups" also encompass heteroatom-containing rings, heteroatom-containing ring systems, heteroaromatic rings, and heteroaromatic ring systems. "Organyl groups," "organylene groups," and "organic groups" can be linear or branched unless otherwise specified. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," respectively, as members.

For the purposes of this application, the term or variations of the term "organyl group consisting of inert functional groups" refers to an organyl group wherein the organic functional group(s) and/or atom(s) other than carbon and hydrogen present in the functional group are restricted to those functional group(s) and/or atom(s) other than carbon and hydrogen which do not complex with a metal compound and/or are inert under the process conditions defined herein. Thus, the term or variation of the term "organyl group consisting of inert functional groups" further defines the particular organyl groups that can be present within the organyl group consisting of inert functional groups. Additionally, the term "organyl group consisting of inert functional groups" can refer to the presence of one or more inert functional groups within the organyl group. The term or variation of the term "organyl group consisting of inert functional groups" definition includes the hydrocarbyl group as a member (among other groups). Similarly, an "organylene group consisting of inert functional groups" refers to an organic group formed by removing two hydrogen atoms from one or two carbon atoms of an organic compound consisting of inert functional groups and an "organic group consisting of inert functional groups" refers to a generalized organic group consisting of inert functional groups formed by removing one or more hydrogen atoms from one or more carbon atoms of an organic compound consisting of inert functional groups.

For purposes of this application, an "inert functional group" is a group which does not substantially interfere with the process described herein in which the material having an inert functional group takes part and/or does not complex with a metal compound of a metal complex. The term "does not complex with the metal compound" can include groups that could complex with a metal compound but in particular molecules described herein may not complex with a metal compound due to its positional relationship within a ligand. For example, while an ether group can complex with a metal compound, an ether group located at a para position of a substituted phenyl phosphinyl group may be an inert functional group because a single metal compound cannot complex with both the para ether group and the $N^2$-phosphinyl formamidine group of the same metal complex molecule. Thus, the inertness of a particular functional group is not only related to the functional group's inherent inability to complex the metal compound, but can also be related to the functional group's position within the metal complex. Non-limiting examples of inert functional groups which do not substantially interfere with processes described herein can include halo (fluoro, chloro, bromo, and iodo), nitro, hydrocarboxy groups (e.g., alkoxy, and/or aroxy, among others), sulfidyl groups, and/or hydrocarbyl groups, among others.

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Non-limiting examples of hydrocarbyl groups include ethyl, phenyl, tolyl, propenyl, and the like. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g., halogenated alkane indicates the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl group are derived by removal of a hydrogen atom from a primary, secondary, and tertiary carbon atom, respectively, of an alkane. The n-alkyl group can be derived by removal of a hydrogen atom from a terminal carbon atom of a linear alkane.

An aliphatic compound is an acyclic or cyclic, saturated or unsaturated carbon compound, excluding aromatic compounds. Thus, an aliphatic compound is an acyclic or cyclic, saturated or unsaturated carbon compound, excluding aromatic compounds; that is, an aliphatic compound is a non-aromatic organic compound. An "aliphatic group" is a generalized group formed by removing one or more hydrogen atoms (as necessary for the particular group) from a carbon atom of an aliphatic compound. Thus, an aliphatic compound is an acyclic or cyclic, saturated or unsaturated carbon compound, excluding aromatic compounds. That is, an aliphatic compound is a non-aromatic organic compound. Aliphatic compounds and therefore aliphatic groups can contain organic functional group(s) and/or atom(s) other than carbon and hydrogen.

The term "substituted" when used to describe a compound or group, for example, when referring to a substituted analog of a particular compound or group, is intended to describe any non-hydrogen moiety that formally replaces a hydrogen in that group, and is intended to be non-limiting. A group or groups can also be referred to herein as "unsubstituted" or by equivalent terms, such as "non-substituted," which refers to the original group in which a non-hydrogen moiety does not replace a hydrogen within that group. "Substituted" is intended to be non-limiting and include inorganic substituents or organic substituents.

The term "olefin" whenever used in this specification and claims refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s).

The term "alkene" whenever used in this specification and claims refers to a linear or branched aliphatic hydrocarbon olefin that has one or more carbon-carbon double bonds. Alkenes having only one, only two, only three, etc., such multiple bonds can be identified by use of the term "mono," "di," "tri," etc., within the name. For example, alkamonoenes, alkadienes, and alkatrienes refer to linear or branched acyclic hydrocarbon olefins having only one carbon-carbon double bond (acyclic having a general formula of $C_nH_{2n}$—), only two carbon-carbon double bonds (acyclic having a general formula of $C_nH_{2n-2}$), and only three carbon-carbon double bonds (acyclic having a general formula of $C_{11}H_{2n-4}$), respectively. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replaced with a halogen atom.

The term "alpha olefin" as used in this specification and claims refers to an olefin that has a carbon-carbon double bond between the first and second carbon atoms of the longest contiguous chain of carbon atoms. The term "alpha olefin" includes linear and branched alpha olefins unless expressly stated otherwise. In the case of branched alpha olefins, a branch can be at the 2 position (a vinylidene) and/or the 3 position or higher with respect to the olefin double bond. The term "vinylidene" whenever used in this specification and claims refers to an alpha olefin having a branch at the 2 position with respect to the olefin double bond. By itself, the term "alpha olefin" does not indicate the presence or absence of other carbon-carbon double bonds unless explicitly indicated.

The term "normal alpha olefin" whenever used in this specification and claims refers to a linear aliphatic monoolefin having a carbon-carbon double bond between the first and second carbon atoms. It is noted that "normal alpha olefin" is not synonymous with "linear alpha olefin" as the term "linear alpha olefin" can include linear olefinic compounds having a double bond between the first and second carbon atoms.

The terms "room temperature" or "ambient temperature" are used herein to describe any temperature from 15° C. to 35° C. wherein no external heat or cooling source is directly applied to the reaction vessel. Accordingly, the terms "room temperature" and "ambient temperature" encompass the individual temperatures and any and all ranges, subranges, and combinations of subranges of temperatures from 15° C. to 35° C. wherein no external heating or cooling source is directly applied to the reaction vessel. The term "atmospheric pressure" is used herein to describe an earth air pressure wherein no external pressure modifying means is utilized. Generally, unless practiced at extreme earth altitudes, "atmospheric pressure" is about 1 atmosphere (alternatively, about 14.7 psi or about 101 kPa).

Features within this disclosure that are provided as a minimum value can be alternatively stated as "at least" or "greater than or equal to" any recited minimum value for the feature disclosed herein. Features within this disclosure that are provided as a maximum value can be alternatively stated as "less than or equal to" or "below" any recited maximum value for the feature disclosed herein.

Within this disclosure, the normal rules of organic nomenclature will prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. By way of another example, reference to a 3-substituted naphth-2-yl indicates that there is a non-hydrogen substituent located at the 3 position and hydrogens located at the 1, 4, 5, 6, 7, and 8 positions. References to compounds or groups having substitutions at positions in addition to the indicated position will be referenced using comprising or some other alternative language. For example, a reference to a phenyl group comprising a substituent at the 4 position refers to a phenyl group having a non-hydrogen substituent group at the 4 position and hydrogen or any non-hydrogen group at the 2, 3, 5, and 6 positions.

Use of the term "optionally" with respect to any element of a claim is intended to mean that the subject element is required, or alternatively, is not required. Both alternatives are intended to be within the scope of the claim.

Unless otherwise specified, any carbon-containing group for which the number of carbon atoms is not specified can have, according to proper chemical practice, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, or any range or combination of ranges between these values. For example, unless otherwise specified, any carbon-containing group can have from 1 to 30 carbon atoms, from 1 to 25 carbon atoms, from 1 to 20 carbon atoms, from 1 to 15 carbon atoms, from 1 to 10 carbon atoms, or from 1 to 5 carbon atoms. Moreover, other identifiers or qualifying terms can be utilized to indicate the presence or absence of a particular substituent, a particular regiochemistry and/or stereochemistry, or the presence or absence of a branched underlying structure or backbone.

Processes and/or methods described herein utilize steps, features, and compounds which are independently described herein. The process and methods described herein may or may not utilize step identifiers (e.g., 1), 2), etc., a), b), etc., or i), ii), etc.), features (e.g., 1), 2), etc., a), b), etc., or i), ii), etc.), and/or compound identifiers (e.g., first, second, etc.). However, it should be noted that processes and/or methods described herein can have multiple steps, features (e.g., reagent ratios, formation conditions, among other considerations), and/or multiple compounds having the same general descriptor. Consequently, it should be noted that the processes and/or methods described herein can be modified to use an appropriate step or feature identifier (e.g., 1), 2), etc., a), b), etc., or i), ii), etc.) and/or compound identifier (e.g., first, second, etc.) regardless of step, feature, and/or compound identifier utilized in a particular aspect and/or embodiment described herein and that step or feature identifiers can be added and/or modified to indicate individual different steps/features/compounds utilized within the process and/or methods without detracting from the general disclosure.

Embodiments disclosed herein can provide the materials listed as suitable for satisfying a particular feature of the embodiment delimited by the term "or." For example, a particular feature of the disclosed subject matter can be disclosed as follows: Feature X can be A, B, or C. It is also contemplated that for each feature the statement can also be phrased as a listing of alternatives such that the statement "Feature X is A, alternatively B, or alternatively C" is also an embodiment of the present disclosure whether or not the statement is explicitly recited.

In an embodiment, the compositions described herein can comprise $C_{10}$ monoolefins. Generally, a monoolefin is a linear or branched aliphatic hydrocarbon olefin that has one and only one carbon-carbon double bond. Generally, a $C_n$ monoolefin is a linear or branched aliphatic hydrocarbon olefin that has n and only n carbon atoms, and one and only one carbon-carbon double bond. A $C_{10}$ monoolefin is a linear or branched aliphatic hydrocarbon olefin that has ten and only ten carbon atoms, and one and only one carbon-carbon double bond.

In an embodiment, the composition disclosed herein can comprise (a) at least 76 mol %, at least 78 mol %, at least 80 mol %, or at least 82 mol % $C_{10}$ monoolefins, and (b) at least 1 mol %, at least 2 mol %, at least 3 mol %, or at least 4 mol % $C_{14}$ monoolefins. In an embodiment, the compositions disclosed herein can comprise (a) from 76 mol % to 92 mol %, from 78 mol % to 90 mol %, from 80 mol % to 88 mol %, or from 82 mol % to 86 mol % $C_{10}$ monoolefins; and (b) from 1 mol % to 12 mol %, from 2 mol % to 10 mol %, from 3 mol % to 8 mol %, or from 4 mol % to 7 mol % $C_{14}$ monoolefins. For purposes of the disclosure herein, a composition comprising (a) at least 76 mol % $C_{10}$ monoolefins, and (b) at least 1 mol % $C_{14}$ monoolefins can also be referred to as a "first composition" or "first compositions."

In another embodiment, the composition(s) disclosed herein can comprise at least 95 mol %, at least 96 mol %, at least 97 mol %, at least 98 mol %, or at least 99 mol % $C_{10}$ monoolefins. For purposes of the disclosure herein, a composition comprising at least 95 mol % $C_{10}$ monoolefins can also be referred to as a "second composition" or "second compositions."

Embodiments of $C_{10}$ monoolefins are described herein (e.g., identity and molar amounts of specific $C_{10}$ monoolefins and molar ratios of specific $C_{10}$ monoolefins, among other $C_{10}$ monoolefins features). These $C_{10}$ monoolefin embodiments can be used without limitation to further describe any composition disclosed herein comprising $C_{10}$ monoolefins disclosed herein (e.g., the "first composition" or the "second composition").

In an embodiment, the $C_{10}$ monoolefins of any composition comprising $C_{10}$ monoolefins described herein can comprise, can consist essentially of, or can be, 2-butyl-1-hexene, 3-propyl-1-heptene, 4-ethyl-1-octene, and 5-methyl-1-nonene. In an embodiment, the $C_{10}$ monoolefins of any composition comprising $C_{10}$ monoolefins described herein can comprise i) at least 3 mol %, at least 4 mol %, at least 5 mol %, at least 6 mol %, at least 7 mol %, or at least 8 mol % 2-butyl-1-hexene; ii) at least 8 mol %, at least 9 mol %, at least 10 mol %, at least 11 mol %, at least 12 mol %, or at least 13 mol % 3-propyl-1-heptene; iii) at least 6 mol %, at least 7 mol %, at least 8 mol %, at least 9 mol %, at least 10 mol %, or at least 11 mol % 4-ethyl-1-octene; and iv) at least 20 mol %, at least 22 mol %, at least 24 mol %, at least 26 mol %, at least 28 mol %, or at least 30 mol % 5-methyl-1-nonene.

In an embodiment, the $C_{10}$ monoolefins of any composition comprising $C_{10}$ monoolefins described herein can comprise from 3 mol % to 20 mol %, from 4 mol % to 18 mol %, from 5 mol % to 17 mol %, from 6 mol % to 16 mol %, or from 7 mol % to 15 mol % 2-butyl-1-hexene. In an embodiment, the $C_{10}$ monoolefins of any composition comprising $C_{10}$ monoolefins described herein can comprise from 10 mol % to 32 mol %, from 11 mol % to 30 mol %, from 12 mol % to 28 mol %, from 13 mol % to 26 mol %, or from 14 mol % to 24 mol % 3-propyl-1-heptene. In an embodiment, the $C_{10}$ monoolefins of any composition comprising $C_{10}$ monoolefins described herein can comprise from 7 mol % to 25 mol %, from 8 mol % to 24 mol %, from 9 mol % to 23 mol %, from 10 mol % to 22 mol %, or from 11 mol % to 21 mol % 4-ethyl-1-octene. In an embodiment, the $C_{10}$ monoolefins of any composition comprising $C_{10}$ monoolefins described herein can comprise from 24 mol % to 52 mol %, from 26 mol % to 50 mol %, from 28 mol % to 48 mol %, from 30 mol % to 46 mol %, or from 32 mol % to 44 mol % 5-methyl-1-nonene.

In an embodiment, the $C_{10}$ monoolefins of any composition comprising $C_{10}$ monoolefins described herein can comprise i) from 3 mol % to 20 mol %, from 4 mol % to 18 mol %, from 5 mol % to 17 mol %, from 6 mol % to 16 mol %, or from 7 mol % to 15 mol % 2-butyl-1-hexene; ii) from 10 mol % to 32 mol %, from 11 mol % to 30 mol %, from 12 mol % to 28 mol %, from 13 mol % to 26 mol %, or from 14 mol % to 24 mol % 3-propyl-1-heptene; iii) from 7 mol % to 25 mol %, from 8 mol % to 24 mol %, from 9 mol % to 23 mol %, from 10 mol % to 22 mol %, or from 11 mol % to 21 mol % 4-ethyl-1-octene; and iv) from 24 mol % to 52 mol %, from 26 mol % to 50 mol %, from 28 mol % to 48 mol %, from 30 mol % to 46 mol %, or from 32 mol % to 44 mol % 5-methyl-1-nonene.

In an embodiment, the $C_{10}$ monoolefins of any composition comprising $C_{10}$ monoolefins described herein can have a molar ratio of 5-methyl-1-nonene to 2-butyl-1-hexene of at least 2:1, at least 2.4:1, at least 2.6:1, or at least 2.8:1. In an embodiment, the $C_{10}$ monoolefins of any composition comprising $C_{10}$ monoolefins described herein can have a molar ratio of 5-methyl-1-nonene to 3-propyl-1-heptene of at least 1.2:1, at least 1.4:1, at least 1.6:1, or at least 1.8:1. In an embodiment, the $C_{10}$ monoolefins of any composition comprising $C_{10}$ monoolefins described herein can have molar ratio of 5-methyl-1-nonene to 4-ethyl-1-octene of at least 1.6:1, at least 1.7:1, at least 1.9:1, or at least 2.1:1. In an embodiment, the $C_{10}$ monoolefins of any composition comprising $C_{10}$ monoolefins described herein can have a molar ratio of 5-methyl-1-nonene to 2-butyl-1-hexene of at least 2:1, at least 2.4:1, at least 2.6:1, or at least 2.8:1; a molar ratio of 5-methyl-1-nonene to 3-propyl-1-heptene of at least 1.2:1, at least 1.4:1, at least 1.6:1, or at least 1.8:1; and a molar ratio of 5-methyl-1-nonene to 4-ethyl-1-octene of at least 1.6:1, at least 1.7:1, at least 1.9:1, or at least 2.1:1.

In an embodiment, the $C_{10}$ monoolefins of any composition comprising $C_{10}$ monoolefins described herein can comprise linear $C_{10}$ monoolefins. In such embodiment, the linear $C_{10}$ monoolefins can comprise, can consist essentially of, or can be, 1-decene, 4-decene, 5-decene, or combinations thereof; alternatively, 1-decene; alternatively, 4-decene and/or 5-decene; alternatively, 4-decene; or alternatively, 5-decene. In an embodiment, the $C_{10}$ monoolefins of any composition comprising $C_{10}$ monoolefins described herein can comprise less than or equal to 26 mol %, less than or equal to 24 mol %, less than or equal to 22 mol %, less than or equal to 20 mol %, or less than or equal to 18 mol % linear $C_{10}$ monoolefins. In an embodiment, the $C_{10}$ monoolefins of any composition comprising $C_{10}$ monoolefins described herein can comprise from 1 mol % to 16 mol %, from 2 mol % to 15 mol %, from 3 mol % to 14 mol %, from 4 mol % to 13 mol %, or from 6 mol % to 12 mol % 4-decene and/or 5-decene. In some embodiments, the $C_{10}$ monoolefins of any composition comprising $C_{10}$ monoolefins described herein can comprise less than or equal to 10 mol %, less than or equal to 9 mol %, less than or equal to 8 mol %, less than or equal to 7 mol %, or less than or equal to 6 mol % 1-decene. In other embodiments, the $C_{10}$ monoolefins of any composition comprising $C_{10}$ monoolefins described herein can comprise from 0.5 mol % to 9 mol %, from 1 mol % to 8 mol %, from 1.5 mol % to 7 mol %, or from 2 mol % to 6 mol % 1-decene.

In an embodiment, the first compositions disclosed herein can further comprise $C_{9-}$ monoolefins, $C_{11+}$ monoolefins, or combinations thereof; alternatively, $C_{9-}$ monoolefins; or alternatively, monoolefins. In an embodiment, the $C_{9-}$ monoolefins can comprise, can consist essentially of, or can be, a $C_7$ monoolefin, a $C_8$ monoolefin, a $C_9$ monoolefin, or combinations thereof; alternatively, a $C_7$ monoolefin; alternatively, a $C_8$ monoolefin; or alternatively, a $C_9$ monoolefin. In some embodiments, the $C_{9-}$ monoolefins can comprise, can consist essentially of, or can be, a $C_8$ monoolefin. In an embodiment, the $C_{11+}$ monoolefins can comprise, can consist essentially of, or can be, a $C_{11}$ monoolefin, a $C_{12}$ monoolefin, a $C_{13}$ monoolefin, a $C_{14}$ monoolefin, a $C_{15}$ monoolefin, a $C_{16}$ monoolefin, a $C_{17}$ monoolefin, a $C_{18}$ monoolefin, or combinations thereof; alternatively, a $C_{11}$ monoolefin; alternatively, a $C_{12}$ monoolefin; alternatively, a $C_{13}$ monoolefin; alternatively, a $C_{14}$ monoolefin; alternatively, a $C_{15}$ monoolefin; alternatively, a $C_{16}$ monoolefin; alternatively, a $C_{17}$ monoolefin; or alternatively, a $C_{18}$ monoolefin. In some embodiments, the $C_{11+}$ monoolefins can comprise, can consist essentially of, or can be, a $C_{12}$ monoolefin, a $C_{16}$ monoolefin, a $C_{18}$ monoolefin, or combinations thereof; alternatively, a $C_{12}$ monoolefin; alternatively, a $C_{16}$ monoolefin; or alternatively, a $C_{18}$ monoolefin.

In an embodiment, the first compositions disclosed herein can further comprise $C_8$ monoolefins, $C_{12}$ monoolefins, $C_{16}$ monoolefins, $C_{18}$ monoolefins, or combinations thereof; alternatively, $C_8$ monoolefins; alternatively, $C_{12}$ monoolefins; alternatively, $C_{16}$ monoolefins and/or $C_{18}$ monoolefins; alternatively, $C_{16}$ monoolefins; or alternatively, $C_{18}$ monoolefins. In an embodiment, the $C_8$ monoolefins can comprise 1-octene. In an embodiment, the $C_{12}$ monoolefins can comprise 1-dodecene.

In an embodiment, the first compositions disclosed herein can further comprise from 0.1 mol % to 5 mol %, from 0.25 mol % to 4 mol %, or from 0.5 mol % to 3 mol % $C_8$ monoolefins. In such embodiment, the $C_8$ monoolefins can comprise at least 95 mol %, at least 96 mol %, at least 97 mol %, at least 98 mol %, or at least 99 mol % 1-octene. In an embodiment, the first compositions disclosed herein can further comprise from 0.1 mol % to 5 mol %, from 0.25 mol % to 4 mol %, or from 0.5 mol % to 3 mol % $C_{12}$ monoolefins. In such embodiment, the $C_{12}$ monoolefins can comprise from 54 mol % to 74 mol %, from 56 mol % to 72 mol %, from 58 mol % to 70 mol %, or from 60 mol % to 68 mol % 1-dodecene. In an embodiment, the first compositions disclosed herein can further comprise from 0.05 mol % to 2 mol %, from 0.04 mol % to 1.5 mol %, from 0.06 mol % to 1.25 mol %, from 0.08 mol % to 1 mol %, or from 0.1 mol % to 0.75 mol % $C_{16}$ monoolefins and/or $C_{18}$ monoolefins In an embodiment, the first compositions disclosed herein can further comprise saturated hydrocarbons. In such embodiment, the saturated hydrocarbons can comprise, can consist essentially of, or can be, acyclic saturated hydrocarbons, cyclic saturated hydrocarbons, or combinations thereof; alternatively, acyclic saturated hydrocarbons; or alternatively, cyclic saturated hydrocarbons.

In an embodiment, the acyclic saturated hydrocarbons can comprise, can consist essentially of, or can be, a $C_7$ to $C_{18}$ acyclic saturated hydrocarbon. In such embodiment, the $C_7$ to $C_{18}$ acyclic saturated hydrocarbon can comprise, can consist essentially of, or can be, a $C_7$ acyclic saturated hydrocarbon, a $C_8$ acyclic saturated hydrocarbon, a $C_9$ acyclic saturated hydrocarbon, a $C_{10}$ acyclic saturated hydrocarbon, a $C_{11}$ acyclic saturated hydrocarbon, a $C_{12}$ acyclic saturated hydrocarbon, a $C_{13}$ acyclic saturated hydrocarbon, a $C_{14}$ acyclic saturated hydrocarbon, a $C_{15}$ acyclic saturated hydrocarbon, a $C_{16}$ acyclic saturated hydrocarbon, a $C_{17}$ acyclic saturated hydrocarbon, a $C_{18}$ acyclic saturated hydrocarbon, or combinations thereof; alternatively, a $C_7$ acyclic saturated hydrocarbon; alternatively, a $C_8$ acyclic saturated hydrocarbon; alternatively, a $C_9$ acyclic saturated hydrocarbon; alternatively, a $C_{10}$ acyclic saturated hydrocarbon; alternatively, a $C_{11}$ acyclic saturated hydrocarbon; alternatively, a $C_{12}$ acyclic saturated hydrocarbon; alternatively, a $C_{13}$ acyclic saturated hydrocarbon; alternatively, a $C_{14}$ acyclic saturated hydrocarbon; alternatively, a $C_{15}$ acyclic saturated hydrocarbon; alternatively, a $C_{16}$ acyclic saturated hydrocarbon; alternatively, a $C_{17}$ acyclic saturated hydrocarbon; or alternatively, a $C_{18}$ acyclic saturated hydrocarbon. In some embodiments, the $C_7$ to $C_{18}$ acyclic saturated hydrocarbon can comprise, can consist essentially of, or can be, a $C_8$ acyclic saturated hydrocarbon, a $C_{10}$ acyclic saturated hydrocarbon, a $C_{12}$ acyclic saturated hydrocarbon, a $C_{14}$ acyclic saturated hydrocarbon, a $C_{16}$ acyclic saturated hydrocarbon, a $C_{18}$ acyclic saturated hydrocarbon, or combinations thereof. In other embodiments, the $C_7$ to $C_{18}$ acyclic saturated hydrocarbon can comprise, can consist essentially of, or can be, a $C_8$ acyclic saturated hydrocarbon, a $C_{10}$ acyclic saturated hydrocarbon, a $C_{12}$ acyclic saturated hydrocarbon, a $C_{14}$ acyclic saturated hydrocarbon, or combinations thereof. In an embodiment, the acyclic saturated hydrocarbons can comprise, can consist essentially of, or can be, octane, decane, dodecane, tetradecane, or combinations thereof; alternatively, decane, dodecane, or combinations thereof; alternatively, octane; alternatively, decane; alternatively, dodecane; or alternatively, tetradecane. In an embodiment, the acyclic saturated hydrocarbons can comprise, can consist essentially of, or can be, decane, dodecane, or combinations thereof; alternatively, decane; or alternatively, dodecane.

In an embodiment, the saturated hydrocarbons can comprise, can consist essentially of, or can be, acyclic saturated hydrocarbons. In an embodiment, the first compositions disclosed herein can further comprise from 0.2 mol % to 6 mol %, from 0.3 mol % to 4 mol %, from 0.4 mol % to 2 mol %, or from 0.5 mol % to 1.5 mol % acyclic saturated hydrocarbons. In an embodiment, the acyclic saturated hydrocarbons can comprise from 10 mol % to 26 mol %, from 12 mol % to 24 mol %, or from 14 mol % to 22 mol % octane. In an embodiment, the acyclic saturated hydrocarbons can comprise from 24 mol % to 48 mol %, from 27 mol % to 45 mol %, or from 30 mol % to 42 mol % decane. In an embodiment, the acyclic saturated hydrocarbons can comprise from 22 mol % to 40 mol %, from 24 mol % to 38 mol %, or from 26 mol % to 36 mol % dodecane. In an embodiment, the acyclic saturated hydrocarbons can comprise from 7 mol % to 23 mol %, from 9 mol % to 21 mol %, or from 11 mol % to 19 mol % tetradecane. In some embodiments, the acyclic saturated hydrocarbons can comprise a) from 10 mol % to 26 mol %, from 12 mol % to 24 mol %, or from 14 mol % to 22 mol % octane; b) from 24 mol % to 48 mol %, from 27 mol % to 45 mol %, or from 30 mol % to 42 mol % decane; c) from 22 mol % to 40 mol %, from 24 mol % to 38 mol %, or from 26 mol % to 36 mol % dodecane; and d) from 7 mol % to 23 mol %, from 9 mol % to 21 mol %, or from 11 mol % to 19 mol % tetradecane.

In an embodiment, the saturated hydrocarbons can comprise, can consist essentially of, or can be, a cyclic saturated hydrocarbon. In an embodiment, the first compositions disclosed herein can further comprise from 1.9 mol % to 5.1 mol %, from 2.1 mol % to 4.9 mol %, from 2.3 mol % to 4.7 mol %, or from 2.5 mol % to 4.5 mol % cyclic saturated hydrocarbons. In an embodiment, the saturated hydrocarbons can comprise, can consist essentially of, or can be, a $C_5$ to $C_8$ cyclic saturated hydrocarbon. In such embodiment, the $C_5$ to $C_8$ cyclic saturated hydrocarbon can comprise, can consist essentially of, or can be, a $C_5$ cyclic saturated hydrocarbon, a $C_6$ cyclic saturated hydrocarbon, a $C_7$ cyclic saturated hydrocarbon, a $C_8$ cyclic saturated hydrocarbon, or combinations thereof; alternatively, a $C_5$ cyclic saturated hydrocarbon; alternatively, a $C_6$ cyclic saturated hydrocarbon; alternatively, a $C_7$ cyclic saturated hydrocarbon; or alternatively, a $C_8$ cyclic saturated hydrocarbon. In some embodiments, the $C_5$ to $C_8$ cyclic saturated hydrocarbon can comprise, can consist essentially of, or can be, a $C_6$ cyclic saturated hydrocarbon, a $C_7$ cyclic saturated hydrocarbon, or combinations thereof. In an embodiment, the cyclic saturated hydrocarbons can comprise, can consist essentially of, or can be, methylcyclopentane, cyclohexane, methylcyclohexane, or combinations thereof; alternatively, methylcyclopentane; alternatively, cyclohexane; or alternatively, methylcyclohexane.

In an embodiment, the first composition can comprise an aromatic hydrocarbon. In an embodiment, the first compositions disclosed herein can further comprise from 1 mol % to 3.4 mol %, from 1.2 mol % to 3.2 mol %, from 1.4 mol % to 3.0 mol %, or from 1.6 mol % to 2.8 mol % of an aromatic hydrocarbon. In an embodiment, the first compositions disclosed herein can further comprise a $C_6$ to $C_{12}$ aromatic hydrocarbon or $C_6$ to $C_{12}$ aromatic compound. In such embodiment, the $C_6$ to $C_{12}$ aromatic hydrocarbon can comprise, can consist essentially of, or can be, a $C_6$ aromatic hydrocarbon, a $C_7$ aromatic hydrocarbon, a $C_8$ aromatic hydrocarbon, a $C_9$ aromatic hydrocarbon, a $C_{10}$ aromatic hydrocarbon, a $C_{11}$ aromatic hydrocarbon, a $C_{12}$ aromatic hydrocarbon, or combinations thereof; alternatively, a $C_6$ aromatic hydrocarbon, a $C_7$ aromatic hydrocarbon, a $C_8$ aromatic hydrocarbon, or combinations thereof; alternatively, a $C_6$ aromatic hydrocarbon; alternatively, a $C_7$ aromatic hydrocarbon; alternatively, a $C_8$ aromatic hydrocarbon; alternatively, a $C_9$ aromatic hydrocarbon; alternatively, a $C_{10}$ aromatic hydrocarbon; alternatively, a $C_{11}$ aromatic hydrocarbon; or alternatively, a $C_{12}$ aromatic hydrocarbon. In some embodiments, the $C_6$ to $C_{12}$ aromatic hydrocarbon can comprise, can consist essentially of, or can be, a $C_6$ aromatic hydrocarbon, a $C_7$ aromatic hydrocarbon, a $C_8$ aromatic hydrocarbon, or combinations thereof; alternatively, a $C_6$ aromatic hydrocarbon; alternatively, a $C_7$ aromatic hydrocarbon; or alternatively, a $C_8$ aromatic hydrocarbon. In an embodiment, the $C_6$ to $C_{12}$ aromatic hydrocarbon can comprise, can consist essentially of, or can be, benzene, toluene, ethylbenzene, xylene, mesitylene, hexamethylbenzene, or combination thereof; alternatively, benzene, toluene, ethylbenzene, xylene, mesitylene, or combinations thereof; alternatively, toluene, ethylbenzene, xylene, or combinations thereof; alternatively, benzene; alternatively, toluene; alternatively, ethylbenzene; alternatively, xylene; alternatively, mesitylene; or alternatively, hexamethylbenzene.

In an embodiment, the first compositions disclosed herein can further comprise an alcohol. In an embodiment, the first compositions disclosed herein can further comprise from 0.4 mol % to 3 mol %, from 0.6 mol % to 3 mol %, from 0.8 mol % to 2.5 mol %, or from 1 mol % to 2 mol % of an alcohol. In some embodiments, the alcohol can comprise, can consist essentially of, or can be, a $C_4$ to $C_{12}$ alcohol; alternatively a $C_6$ to $C_{12}$ alcohol; or alternatively a $C_6$ to $C_{10}$ alcohol. In some embodiments, the alcohol can comprise, can consist essentially of, or can be, a $C_4$ alcohol, a $C_5$ alcohol, a $C_6$ alcohol, a $C_7$ alcohol, a $C_8$ alcohol, a $C_9$ alcohol, a $C_{10}$ alcohol, a $C_{11}$ alcohol, a $C_{12}$ alcohol, or combinations thereof; alternatively, a $C_6$ alcohol, a $C_7$ alcohol, a $C_8$ alcohol, a $C_9$ alcohol, a $C_{10}$ alcohol, a $C_{11}$ alcohol, a $C_{12}$ alcohol, or combinations thereof; alternatively, a $C_6$ alcohol, a $C_7$ alcohol, a $C_8$ alcohol, a $C_9$ alcohol, a $C_{10}$ alcohol, or combinations thereof; alternatively, a $C_4$ alcohol; alternatively, a $C_5$ alcohol; alternatively, a $C_6$ alcohol; alternatively, a $C_7$ alcohol; alternatively, a $C_8$ alcohol; alternatively, a $C_9$ alcohol; alternatively, a $C_{10}$ alcohol; alternatively, a $C_{11}$ alcohol; or alternatively, a $C_{12}$ alcohol. In an embodiment, the alcohol can comprise, can consist essentially of, or can be, 1-hexanol, 2-hexanol, 3-hexanol, 1-heptanol, 2-heptanol, 3-heptanol, 4-heptanol, 2-ethyl-1-hexanol, 2-methyl-3-heptanol, 1-octanol, 2-octanol, 3-octanol, 4-octanol, 1-decanol, 2-decanol, 3-decanol, 4-decanol, 5-decanol, 7-methyl-2-decanol, 2-ethyl-1-decanol, or combinations thereof; alternatively, 1-hexanol, 2-hexanol, 3-hexanol, 1-heptanol, 2-heptanol, 3-heptanol, 4-heptanol, 2-ethyl-1-hexanol, 2-methyl-3-heptanol, 1-octanol, 2-octanol, 3-octanol, 4-octanol, 1-decanol, 2-decanol, 3-decanol, 4-decanol, 5-decanol, or combination thereof; alternatively, 1-hexanol; alternatively, 2-hexanol; alternatively, 3-hexanol; alternatively, 1-heptanol; alternatively, 2-heptanol; alternatively, 3-heptanol; alternatively, 4-heptanol; alternatively, 2-ethyl-1-hexanol; alternatively, 2-methyl-3-heptanol; alternatively, 1-octanol; alternatively, 2-octanol; alternatively, 3-octanol; alternatively, 4-octanol; alternatively, 1-decanol; alternatively, 2-decanol; alternatively, 3-decanol; alternatively, 4-decanol; alternatively, 5-decanol; alternatively, 7-methyl-2-decanol; or alternatively, 2-ethyl-1-decanol.

In an embodiment, the second compositions disclosed herein can comprises less than 3 mol %, less than 2.5 mol %, less than 2 mol %, less than 1.5 mol %, less than 1 mol %, or less than 0.5 mol % $C_{9-}$ hydrocarbons. In some embodiments, the $C_{9-}$ hydrocarbons that can be present in the second compositions disclosed herein can comprise, can consist essentially of, or can be saturated $C_{9-}$ hydrocarbons (acyclic and/or cyclic), $C_{9-}$ monoolefins, or combinations thereof; alternatively, saturated $C_{9-}$ hydrocarbons (acyclic and/or cyclic); or alternatively, $C_{9-}$ monoolefins.

In an embodiment, the $C_{9-}$ monoolefins that can be present in the second compositions disclosed herein can comprise, can consist essentially of, or can be, a $C_7$ monoolefin, a $C_8$ monoolefin, a $C_9$ monoolefin, or combinations thereof; alternatively, a $C_7$ monoolefin; alternatively, a $C_8$ monoolefin; or alternatively, a $C_9$ monoolefin. In some embodiments, the $C_{9-}$ monoolefins that can be present in the second compositions disclosed herein can comprise, can consist essentially of, or can be, a $C_8$ monoolefin. In an embodiment, the $C_{9-}$ monoolefins that can be present in the second compositions disclosed herein can comprise, can consist essentially of, or can be, 1-octene.

In an embodiment the $C_{9-}$ saturated hydrocarbons that can be present in the second compositions disclosed herein can comprise, can consist essentially of, or can be $C_{9-}$ acyclic saturated hydrocarbons, $C_{9-}$ cyclic saturated hydrocarbons, or combinations thereof; alternatively, $C_{9-}$ acyclic saturated hydrocarbons; or alternatively, $C_{9-}$ cyclic saturated hydrocarbons. In an embodiment, the $C_{9-}$ acyclic saturated hydrocarbons that can be present in the second compositions disclosed herein can comprise, can consist essentially of, or can be, a $C_7$ acyclic saturated hydrocarbon, a $C_8$ acyclic saturated hydrocarbon, a $C_9$ acyclic saturated hydrocarbon, or combinations thereof; alternatively, a $C_7$ acyclic saturated hydrocarbon; alternatively, a $C_8$ acyclic saturated hydrocarbon; or alternatively, a $C_9$ acyclic saturated hydrocarbon.

In an embodiment, the $C_{9-}$ cyclic saturated hydrocarbon that can be present in the second compositions disclosed herein can comprise, can consist essentially of, or can be, a $C_6$ cyclic saturated hydrocarbon, a $C_7$ cyclic saturated hydrocarbon, a $C_8$ cyclic saturated hydrocarbon, a $C_9$ cyclic saturated hydrocarbon, or combinations thereof; a $C_6$ cyclic saturated hydrocarbon; alternatively, a $C_7$ cyclic saturated hydrocarbon; alternatively, a $C_8$ cyclic saturated hydrocarbon; or alternatively, a $C_8$ cyclic saturated hydrocarbon. In an embodiment, the $C_{9-}$ cyclic saturated hydrocarbons that can be present in the second compositions disclosed herein can comprise, can consist essentially of, or can be, methylcyclopentane, cyclohexane, methylcyclohexane, or combinations thereof; alternatively, methylcyclopentane; alternatively, cyclohexane; or alternatively, methylcyclohexane.

In an embodiment, the second compositions disclosed herein can comprise less than 1 mol %, less than 0.75 mol %, less than 0.5 mol %, less than 0.25 mol %, less than 0.1 mol %, less than 0.05 mol %, less than 0.25 mol %, or less than 0.01 mol % of a $C_6$ to $C_{12}$ aromatic hydrocarbon. In an embodiment, the aromatic hydrocarbons that can be present in the second compositions disclosed herein can comprise, can consist essentially of, or can be, benzene, toluene, ethylbenzene, xylene, mesitylene, or combination thereof; alternatively, benzene, toluene, ethylbenzene, xylene, mesitylene, or combinations thereof; alternatively, toluene, ethylbenzene, xylene, or combinations thereof; alternatively, benzene; alternatively, toluene; alternatively, ethylbenzene; alternatively, xylene; or alternatively, mesitylene.

In an embodiment, the second compositions disclosed herein can comprise less than 1 mol %, less than 0.75 mol %, less than 0.5 mol %, less than 0.25 mol %, less than 0.1 mol %, less than 0.05 mol %, less than 0.25 mol %, or less than 0.01 mol % alcohol. In an embodiment, the alcohols that can be present in the second compositions disclosed herein can comprise, can consist essentially of, or can be, 1-hexanol, 2-hexanol, 3-hexanol, 1-heptanol, 2-heptanol, 3-heptanol, 4-heptanol, 2-ethyl-1-hexanol, 2-methyl-3-heptanol, 1-octanol, 2-octanol, 3-octanol, 4-octanol, or combinations thereof; alternatively, 1-hexanol; alternatively, 2-hexanol; alternatively, 3-hexanol; alternatively, 1-heptanol; alternatively, 2-heptanol; alternatively, 3-heptanol; alternatively, 4-heptanol; alternatively, 2-ethyl-1-hexanol; alternatively, 2-methyl-3-heptanol; alternatively, 1-octanol; alternatively, 2-octanol; alternatively, 3-octanol; or alternatively, 4-octanol. In another embodiment, the alcohols that can be present in the second compositions disclosed herein can comprise, can consist essentially of, or can be, 1-hexanol, 2-hexanol, 3-hexanol, or combinations thereof; alternatively, 1-hexanol; alternatively, 2-hexanol; or alternatively, 3-hexanol.

In an embodiment, the second compositions disclosed herein can comprises less than 3 mol %, less than 2.5 mol %, less than 2 mol %, less than 1.5 mol %, less than 1 mol %, or less than 0.5 mol % hydrocarbons. In some embodiments, the hydrocarbons that can be present in the second compositions disclosed herein can comprise, can consist essentially of, or can be saturated $C_{11+}$ hydrocarbons (acyclic and/or cyclic), $C_{11+}$ monoolefins, or combinations thereof; alternatively, saturated $C_{11+}$ hydrocarbons (acyclic and/or cyclic); or alternatively, $C_{11+}$ monoolefins. In an embodiment, the $C_{11+}$ monoolefin that can be present in the second compositions disclosed herein can comprise, can consist essentially of, or can be, a $C_{11}$ monoolefin, a $C_{12}$ monoolefin, a $C_{13}$ monoolefin, or combinations thereof; alternatively, a $C_{11}$ monoolefin; alternatively, a $C_{12}$ monoolefin; or alternatively, a $C_{13}$ monoolefin. In an embodiment, the $C_{11+}$ acyclic saturated hydrocarbon that can be present in the second compositions disclosed herein can comprise, can consist essentially of, or can be, a $C_{11}$ acyclic saturated hydrocarbon, a $C_{12}$ acyclic saturated hydrocarbon, a $C_{13}$ acyclic saturated hydrocarbon, or combinations thereof; alternatively, a $C_{11}$ acyclic saturated hydrocarbon; alternatively, a $C_{12}$ acyclic saturated hydrocarbon; or alternatively, a $C_{13}$ acyclic saturated hydrocarbon. In an embodiment, the $C_{11+}$ acyclic saturated hydrocarbon that can be present in the second compositions can comprise, can consist essentially of, or can be, dodecane.

Generally, the compositions disclosed herein can be prepared by a process comprising a) contacting 1) ethylene, 2) a catalyst system comprising i) a chromium containing compound, ii) a heteroatomic ligand, and iii) an alkylaluminum compound, and 3) optionally a reaction system diluent; b) forming an oligomer product comprising 1-hexene and/or 1-octene in a reaction system; c) discharging a reaction system effluent from the reaction system; d) contacting the reaction system effluent with a catalyst system deactivating agent; and e) isolating the composition. In an embodiment, the process can comprise a) contacting 1) ethylene, 2) a catalyst system comprising i) a chromium containing compound, ii) a heteroatomic ligand, and iii) an alkylaluminum compound, and 3) optionally a reaction system diluent; b) forming an oligomer product comprising 1-hexene and/or 1-octene in a reaction system; c) discharging a reaction system effluent from the reaction system; d) contacting the reaction system effluent with a catalyst system deactivating agent; and e) isolating a composition comprising (a) at least 76 mol %, at least 78 mol %, at least 80 mol %, or at least 82 mol % $C_{10}$ monoolefins, the $C_{10}$ monoolefins comprising (i) at least 3 mol %, at least 4 mol %, at least 5 mol %, at least 6 mol %, at least 7 mol %, or at least 8 mol % 2-butyl-1-hexene, (ii) at least 8 mol %, at least 9 mol %, at least 10 mol %, at least 11 mol %, at least 12 mol %, or at least 13 mol % 3-propyl-1-heptene, (iii) at least 6 mol %, at least 7 mol %, at least 8 mol %, at least 9 mol %, at least 10 mol %, or at least 11 mol % 4-ethyl-1-octene, and (iv) at least 20 mol %, at least 22 mol %, at least 24 mol %, at least 26 mol %, at least 28 mol %, or at least 30 mol % 5-methyl-1-nonene, and (b) at least 1 mol %, at least 2 mol %, at least 3 mol %, or at least 4 mol % $C_{14}$ monoolefins. In another embodiment, the process can comprise a) contacting 1) ethylene, 2) a catalyst system comprising i) a chromium containing compound, ii) a heteroatomic ligand, and iii) an alkylaluminum compound, and 3) optionally a reaction system diluent; b) forming an oligomer product comprising 1-hexene and/or 1-octene in a reaction system; c) discharging a reaction system effluent from the reaction system; d) contacting the reaction system effluent with a catalyst system deactivating agent; and e) isolating a composition comprising at least 95 mol %, at least 96 mol %, at least 97 mol %, at least 98 mol %, or at least 99 mol % $C_{10}$ monoolefins, the $C_{10}$ monoolefins comprising (i) at least 3 mol %, at least 4 mol %, at least 5 mol %, at least 6 mol %, or at least 7 mol % 2-butyl-1-hexene, (ii) at least 10 mol %, at least 11 mol %, at least 12 mol %, at least 13 mol %, or at least 14 mol % 3-propyl-1-heptene, (iii) at least 7 mol %, at least 8 mol %, at least 9 mol %, at least 10 mol %, or at least 11 mol % 4-ethyl-1-octene, and (iv) at least 24 mol %, at least 26 mol %, at least 28 mol %, at least 30 mol %, or at least 32 mol % 5-methyl-1-nonene. In yet another embodiment, the process can comprise a) contacting 1) ethylene, 2) a catalyst system comprising i) a chromium containing compound, ii) a heteroatomic ligand, and iii) an alkylaluminum compound, and 3) optionally a reaction system diluent; b) forming an oligomer product comprising 1-hexene and/or 1-octene in a reaction system, c) discharging a reaction system effluent from the reaction system; d)

contacting the reaction system effluent with a catalyst system deactivating agent; e) isolating a first composition comprising (a) at least 76 mol %, at least 78 mol %, at least 80 mol %, or at least 82 mol % $C_{10}$ monoolefins, the $C_{10}$ monoolefins comprising (i) at least 3 mol %, at least 4 mol %, at least 5 mol %, at least 6 mol %, at least 7 mol %, or at least 8 mol % 2-butyl-1-hexene, (ii) at least 8 mol %, at least 9 mol %, at least 10 mol %, at least 11 mol %, at least 12 mol %, or at least 13 mol % 3-propyl-1-heptene, (iii) at least 6 mol %, at least 7 mol %, at least 8 mol %, at least 9 mol %, at least 10 mol %, or at least 11 mol % 4-ethyl-1-octene, and (iv) at least 20 mol %, at least 22 mol %, at least 24 mol %, at least 26 mol %, at least 28 mol %, or at least 30 mol % 5-methyl-1-nonene, and (b) at least 1 mol %, at least 2 mol %, at least 3 mol %, or at least 4 mol % $C_{14}$ monoolefins; and f) recovering a second composition comprising at least 95 mol %, at least 96 mol %, at least 97 mol %, at least 98 mol %, or at least 99 mol % $C_{10}$ monoolefins, the $C_{10}$ monoolefins comprising (i) at least 3 mol %, at least 4 mol %, at least 5 mol %, at least 6 mol %, or at least 7 mol % 2-butyl-1-hexene, (ii) at least 10 mol %, at least 11 mol %, at least 12 mol %, at least 13 mol %, or at least 14 mol % 3-propyl-1-heptene, (iii) at least 7 mol %, at least 8 mol %, at least 9 mol %, at least 10 mol %, or at least 11 mol % 4-ethyl-1-octene, and (iv) at least 24 mol %, at least 26 mol %, at least 28 mol %, at least 30 mol %, or at least 32 mol % 5-methyl-1-nonene from the first composition. Further features of the compositions which can be isolated as a step of the processes are independently described herein and these features can be utilized without limitation to further describe the processes described herein which can produce the compositions disclosed herein.

For purposes of the disclosure herein, the term "reaction system" refers to a portion of a process, associated equipment and associated process lines where all necessary reaction components and reaction conditions are present such that a reaction (e.g., oligomerization reaction, ethylene oligomerization, ethylene trimerization, ethylene tetramerization, etc.) can occur at a desired rate. Further, for purposes of the disclosure herein, the reaction system begins where the necessary reaction components and reaction conditions are present to maintain a reaction within 25% of an average reaction rate (e.g., reaction rate is greater than or equal to 25% of the average reaction rate) and the reaction system ends where the conditions do not maintain a reaction rate within 25% of the average reaction rate (e.g., reaction rate is less than 25% of the average reaction rate), based upon a volume average of the reaction rate of the reaction system). For example, in terms of an ethylene oligomerization process, the reaction system begins at the point where sufficient ethylene and catalyst system (e.g., active catalyst system) is present under sufficient reaction conditions to maintain oligomer product production at a desired rate and the reaction system ends at a point where either the catalyst system is deactivated, sufficient ethylene is not present to sustain oligomer product production, or other reaction conditions are not sufficient to maintain the oligomer product production and/or a desired oligomer product production rate. For purposes of the disclosure herein, the reaction system can comprise one or more reactor systems, one or more reactors, and/or associated equipment where all the necessary reaction components and reaction conditions are present such that the reaction can occur at a desired rate.

In an embodiment, the compositions disclosed herein can be isolated from an ethylene trimerization process comprising contacting ethylene and any ethylene trimerization catalyst system disclosed herein to form a trimerization product (or oligomer product) comprising 1-hexene. In other embodiments, the compositions disclosed herein can be isolated from an ethylene tetramerization process comprising contacting ethylene and any ethylene tetramerization catalyst system disclosed herein to form a tetramerization product (or oligomer product) comprising 1-octene. In yet other embodiments, the compositions disclosed herein can be isolated from an ethylene trimerization and tetramerization process comprising contacting ethylene and any ethylene trimerization and tetramerization catalyst system disclosed herein to form a trimerization and tetramerization product (or oligomer product) comprising 1-hexene and 1-octene. Features of the trimerization catalyst system, tetramerization catalyst system, and trimerization and tetramerization catalyst system are independently described herein and these features can be utilized without limitation to further describe the processes described herein which can produce the compositions disclosed herein.

In a further embodiment, ethylene trimerization, ethylene tetramerization, or ethylene trimerization and tetramerization can be performed in the presence of a solvent. In an embodiment, ethylene trimerization, ethylene tetramerization, or ethylene trimerization and tetramerization can comprise contacting hydrogen with ethylene and the catalyst system. In an embodiment the process can further comprise recovering the trimer, tetramer, or trimer and tetramer. Generally, ethylene, the catalyst system (or components of the catalyst system), reaction system solvent (if utilized), hydrogen (if utilized), and any other materials can be a fed to the reaction system and can be supplied to the reaction system via one or more feed lines. For purposes of the disclosure herein, the terms "ethylene trimerization mixture," "ethylene tetramerization mixture," or "ethylene trimerization and tetramerization mixture" refer to a mixture (e.g., reaction mixture) comprising ethylene, the catalyst system (or components of the catalyst system), reaction system solvent (if utilized), hydrogen (if utilized), and any other materials necessary for the oligomerization process.

In some ethylene trimerization, tetramerization, or trimerization and tetramerization embodiments, the ethylene trimerization mixture, ethylene tetramerization mixture, or ethylene trimerization and tetramerization mixture can comprise at least 0.1 wt. %, at least 0.5 wt. %, at least 1 wt. %, at least 2.5 wt. %, at least 5 wt. %, at least 7.5 wt. %, or at least 10 wt. % ethylene, based upon the ethylene trimerization, tetramerization, or trimerization and tetramerization mixture. In other ethylene trimerization, tetramerization, or trimerization and tetramerization embodiments, the ethylene trimerization mixture, ethylene tetramerization mixture, or ethylene trimerization and tetramerization mixture can comprise a maximum of 50 wt. %, 40 wt. %, 30 wt. %, 25 wt. %, 20 wt. %, 17.5 wt. %, or 15 wt. % ethylene, based upon the trimerization, tetramerization, or trimerization and tetramerization mixture. In an ethylene trimerization, tetramerization, or trimerization and tetramerization embodiment, the ethylene in the ethylene trimerization mixture, ethylene tetramerization mixture, or ethylene trimerization and tetramerization mixture can range from any minimum weight percent disclosed herein to any maximum weight percent disclosed herein. In an ethylene trimerization, tetramerization, or trimerization and tetramerization embodiment, the ethylene in the ethylene trimerization mixture, ethylene tetramerization mixture, or ethylene trimerization and tetramerization mixture can range from 0.1 wt. % to 50 wt. %, from 5 wt. % to 40 wt. %, from 5 wt. % to 30 wt. %, from 10 wt. % to 30 wt. %, from 10 wt. % to 25 wt. %, from 10 wt. % to 20 wt. %, from 10 wt. % to 15 wt.

%, or combinations thereof. As will be appreciated by one of skill in the art, and with the help of this disclosure, any other suitable ranges for the amount of ethylene that can be present in the ethylene trimerization mixture, ethylene tetramerization mixture, or ethylene trimerization and tetramerization mixture can be used.

In some embodiments, the process (e.g., ethylene oligomerization process) can be an ethylene trimerization process, ethylene tetramerization process, or an ethylene trimerization and tetramerization process comprising contacting 1) ethylene and 2) a catalyst system comprising i) a chromium containing compound, ii) a heteroatomic ligand, and iii) an alkylaluminum compound to form an ethylene trimerization product, an ethylene tetramerization product, or an ethylene trimerization and tetramerization product (respectively). In other embodiments, the process can be an ethylene trimerization process, ethylene tetramerization process, or an ethylene trimerization and tetramerization process, comprising contacting 1) ethylene and 2) a catalyst system comprising i) a chromium containing compound complexed to a heteroatomic ligand, and ii) an alkylaluminum compound to form an ethylene trimerization product, an ethylene tetramerization product, or an ethylene trimerization and tetramerization product (respectively). In some embodiments, an optional halogen containing compound can be a component of the catalyst system, or alternatively, a halogen containing compound can be a further component of the ethylene trimerization mixture, ethylene tetramerization mixture, or ethylene trimerization and tetramerization mixture contacted to form an ethylene trimerization product, an ethylene tetramerization product, or an ethylene trimerization and tetramerization product. In other embodiments, a solvent (e.g., reaction system diluent) can be a further component of the ethylene trimerization mixture, ethylene tetramerization mixture, or ethylene trimerization and tetramerization mixture contacted to form an ethylene trimerization product, an ethylene tetramerization product, or an ethylene trimerization and tetramerization product. In yet other embodiments, hydrogen can be a further component of the ethylene trimerization mixture, ethylene tetramerization mixture, or ethylene trimerization and tetramerization mixture contacted to form an ethylene trimerization product, an ethylene tetramerization product, or an ethylene trimerization and tetramerization product. In further embodiments, the process (e.g., ethylene oligomerization process, ethylene trimerization process, ethylene tetramerization process, or ethylene trimerization and tetramerization process) can include steps for forming an oligomer product in a reaction system (as described herein), discharging a reaction system effluent from the reaction system (as described herein), contacting the reaction system effluent with a catalyst system deactivating agent (as described herein), and/or isolating a composition (e.g., the first composition and/or second composition).

In the context of the compositions disclosed herein, an ethylene trimerization process, an ethylene tetramerization process, or an ethylene trimerization and tetramerization process can utilize a solvent. For purposes of the disclosure herein, the terms "solvent," "diluent," "reaction system solvent" and "reaction system diluent" can be used interchangeably and refer to and include materials which can act as a solvent or a diluent in the process disclosed herein. In an embodiment, the solvent can be a hydrocarbon, a halogenated hydrocarbon, or combinations thereof. Hydrocarbons and halogenated hydrocarbons which can be used as solvent can include, for example, aliphatic hydrocarbons, aromatic hydrocarbons, petroleum distillates, halogenated aliphatic hydrocarbons, halogenated aromatic hydrocarbons, or combinations thereof. Aliphatic hydrocarbons which can be used as a solvent include $C_3$ to $C_{20}$ aliphatic hydrocarbons, alternatively, $C_4$ to $C_{15}$ aliphatic hydrocarbons, or alternatively, $C_5$ to $C_{10}$ aliphatic hydrocarbons, for example. The aliphatic hydrocarbons which can be used as a solvent can be cyclic or acyclic and/or can be linear or branched, unless otherwise specified. Non-limiting examples of suitable acyclic aliphatic hydrocarbon solvents that can be utilized singularly or in any combination include propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or a mixture of linear and branched $C_7$ acyclic aliphatic hydrocarbons), octane (n-octane or a mixture of linear and branched $C_8$ acyclic aliphatic hydrocarbons), or combinations thereof. Non-limiting examples of suitable cyclic aliphatic hydrocarbon which can be used as a solvent include cyclohexane, methyl cyclohexane, or combinations thereof. Aromatic hydrocarbons which can be used as a solvent include aromatic hydrocarbons, or $C_6$ to $C_{10}$ aromatic hydrocarbons. Non-limiting examples of suitable aromatic hydrocarbons that can be utilized singularly or in any combination as a solvent include benzene, toluene, xylene (including ortho-xylene, meta-xylene, para-xylene, or mixtures thereof), ethylbenzene, or combinations thereof. Halogenated aliphatic hydrocarbons which can be used as a solvent include $C_1$ to $C_{15}$ halogenated aliphatic hydrocarbons, alternatively, $C_1$ to $C_{10}$ halogenated aliphatic hydrocarbons, or alternatively, $C_1$ to $C_5$ halogenated aliphatic hydrocarbons, for example. The halogenated aliphatic hydrocarbons which can be used as a solvent can be cyclic or acyclic and/or can be linear or branched, unless otherwise specified. Non-limiting examples of suitable halogenated aliphatic hydrocarbons which can be used as a solvent include methylene chloride, chloroform, carbon tetrachloride, dichloroethane, trichloroethane, or combinations thereof. Halogenated aromatic hydrocarbons which can be useful as a solvent include $C_6$ to $C_{20}$ halogenated aromatic hydrocarbons, or alternatively, $C_6$ to $C_{10}$ halogenated aromatic hydrocarbons, for example. Non-limiting examples of suitable halogenated aromatic hydrocarbons which can be used as a solvent include chlorobenzene, dichlorobenzene, or combinations thereof, for example.

The choice of solvent can be made on a basis of convenience in processing. For example, isobutane can be chosen to be compatible with diluents used for formation of polyolefins in a subsequent processing step. In some embodiments, the solvent can be chosen to be easily separable from the trimer, tetramer, or trimer and tetramer. In other embodiments, a component of the trimerization, tetramerization, or trimerization and tetramerization product or feedstock can be utilized as the solvent. For example, since 1-hexene can be a component of the trimerization product of an ethylene trimerization process, it can be chosen as the solvent to decrease the need for separation. In yet other embodiments, a process can be carried out in a solvent which is a product of the ethylene trimerization, tetramerization, or trimerization and tetramerization process. Therefore, the choice of reaction system diluent, or solvent, can be based on the selection of the initial olefin reactant (e.g., ethylene) and/or the trimerization, tetramerization, or trimerization and tetramerization product. For example, if the catalyst system is used to trimerize ethylene to 1-hexene, the solvent for the trimerization reaction can be 1-hexene.

In the context of the compositions disclosed herein, an ethylene trimerization process, an ethylene tetramerization process, or an ethylene trimerization and tetramerization process, the reaction mixture (e.g., ethylene trimerization mixture, ethylene tetramerization mixture, or ethylene trimerization and tetramerization mixture) can further comprise a catalyst system (e.g., oligomerization catalyst system, ethylene trimerization catalyst system, ethylene tetramerization catalyst system, or ethylene trimerization and tetramerization catalyst system), or one or more components thereof. In an embodiment, the ethylene trimerization catalyst system, ethylene tetramerization catalyst system, or ethylene trimerization and tetramerization catalyst system can comprise a chromium containing compound, a heteroatomic ligand, and a metal alkyl compound (or alternatively, an alkylaluminum compound). In an embodiment, the ethylene trimerization catalyst system, ethylene tetramerization catalyst system, or ethylene trimerization and tetramerization catalyst system can comprise a chromium containing compound complexed to a heteroatomic ligand, and a metal alkyl compound (or alternatively, an alkylaluminum compound). In another aspect, the ethylene trimerization catalyst system, ethylene tetramerization catalyst system, or ethylene trimerization and tetramerization catalyst system can further comprise a halogen containing compound. The chromium containing compound, chromium containing compound complexed to a heteroatomic ligand, heteroatomic ligand, metal alkyl compound (or alternatively, alkylaluminum compound), and optional halogen containing compound are each independent elements of the catalyst system. These independent elements components of the catalyst system are independently described herein and the catalyst system can be further described utilizing any combination of the chromium containing compound disclosed herein, the heteroatomic ligand disclosed herein, the chromium containing compound complexed to a heteroatomic ligand disclosed herein, the metal alkyl compound (or alternatively, alkylaluminum compound) disclosed herein, and optional halogen containing compound disclosed herein.

Generally, the chromium containing compound (of the catalyst systems disclosed herein) can have a chromium oxidation state of from 0 to 6, or from 2 to 3 (i.e., a chromium(II) compound or a chromium(III) compound). Non-limiting examples of chromium(II) compounds which can be used in the catalyst system disclosed herein can include chromium(II) nitrate, chromium(II) sulfate, chromium(II) fluoride, chromium(II) chloride, chromium(II) bromide, or chromium(II) iodide. Non-limiting examples of chromium(III) compounds which can be used in the catalyst systems disclosed herein can include chromium(III) nitrate, chromium(III) sulfate, chromium(III) fluoride, chromium (III) chloride, chromium(III) bromide, or chromium(III) iodide. In some embodiments, the catalyst system can comprise a chromium(II) alkoxide, a chromium(II) carboxylate, a chromium(II) beta-dionate, a chromium(III) alkoxide, a chromium(III) carboxylate, or a chromium(III) beta-dionate. In some embodiments, each carboxylate group of the chromium containing compound independently can be a $C_2$ to $C_{24}$ carboxylate group, alternatively, a $C_4$ to $C_{19}$ carboxylate group, or alternatively, a $C_5$ to $C_{12}$ carboxylate group. In other embodiments, each alkoxy group of the chromium containing compound independently can be a $C_1$ to $C_{24}$ alkoxy group, alternatively, a $C_4$ to $C_{19}$ alkoxy group, or alternatively, a $C_5$ to $C_{12}$ alkoxy group. In yet other embodiments, each aryloxy group of the chromium containing compound independently can be a $C_6$ to $C_{24}$ aryloxy group, alternatively, a $C_6$ to $C_{19}$ aryloxy group, or alternatively, a $C_6$ to $C_{12}$ aryloxy group. In still yet other embodiments, each beta-dionate group of the chromium containing compound independently can be a $C_5$ to $C_{24}$ beta-dionate group, alternatively, a $C_5$ to $C_{19}$ beta-dionate group, or alternatively, a $C_5$ to $C_{12}$ beta-dionate group. Chromium carboxylates can be particularly useful for the catalyst systems disclosed herein. In an aspect, the catalyst systems disclosed herein can comprise a chromium carboxylate comprising a $C_2$ to $C_{24}$ monocarboxylate, alternatively, a $C_4$ to $C_{19}$ monocarboxylate, or alternatively, a $C_5$ to $C_{12}$ monocarboxylate.

In an embodiment, each carboxylate group of the chromium carboxylate independently can be an acetate, a propionate, a butyrate, a pentanoate, a hexanoate, a heptanoate, an octanoate, a nonanoate, a decanoate, an undecanoate, a dodecanoate, a tridecanoate, a tetradecanoate, a pentadecanoate, a hexadecanoate, a heptadecanoate, or an octadecanoate; or alternatively, a pentanoate, a hexanoate, a heptanoate, an octanoate, a nonanoate, a decanoate, an undecanoate, or a dodecanoate. In some embodiments, each carboxylate group of the chromium carboxylate independently can be acetate, propionate, n-butyrate, isobutyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, laurate (n-dodecanoate), or stearate (n-octadecanoate); or alternatively, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate).

In an embodiment, the chromium containing compound can comprise, can consist essentially of, or can be, a chromium(II) carboxylate or a chromium(III) carboxylate. In an embodiment, the chromium(II) carboxylates can comprise, can consist essentially of, or can be, chromium(II) acetate, chromium(II) propionate, chromium(II) butyrate, chromium(II) isobutyrate, chromium(II) neopentanoate, chromium(II) oxalate, chromium(II) octanoate, chromium (II) 2-ethylhexanoate, chromium(II) laurate, or chromium (II) stearate; or alternatively, chromium(II) acetate, chromium(II) propionate, chromium(II) butyrate, chromium(II) isobutyrate, chromium(II) neopentanoate, chromium(II) octanoate, chromium(II) 2-ethylhexanoate, chromium(II) laurate, or chromium(II) stearate. In an embodiment, the chromium(III) carboxylates can comprise, can consist essentially of, or can be, chromium(III) acetate, chromium(III) propionate, chromium(III) butyrate, chromium(III) isobutyrate, chromium(III) neopentanoate, chromium(III) oxalate, chromium(III) octanoate, chromium(III) 2-ethylhexanoate, chromium(III) 2,2,6,6,-tetramethylheptanedionate, chromium(III) naphthenate, chromium(III) laurate, or chromium(III) stearate.

In an embodiment, the heteroatomic ligand (whether it is a separate component of the catalyst system or is a ligand complexed to the chromium containing compound of the catalyst system) can comprise, can consist essentially of, or can be, an amine compound, an amide compound, an imide compound, or combinations thereof. In an embodiment, the heteroatomic ligand (whether it is a separate component of the catalyst system or is a ligand complexed to the chromium containing compound of the catalyst system) can comprise, can consist essentially of, or can be, a pyrrole compound, a diphosphino aminyl compound, an $N^2$-phosphinyl amidine compound, an $N^2$-phosphinyl formamidine compound, an $N^2$-phosphinyl guanidine compound, or combinations thereof. In some embodiments, the heteroatomic ligand (whether it is a separate component of the catalyst system or is a ligand complexed to the chromium containing compound of the catalyst system) can comprise, can consist essentially of, or can be, a pyrrole compound; alternatively, a diphosphino aminyl compound; alternatively, an $N^2$-phosphinyl amidine compound; alternatively, an $N^2$-phosphinyl formamidine compound; or alternatively, an $N^2$-phosphinyl guanidine compound.

In an embodiment, the amine compound can be a $C_2$ to $C_{30}$ amine; alternatively, a $C_2$ to $C_{20}$ amine; alternatively, $C_2$ to $C_{15}$ amine; or alternatively, a $C_2$ to $C_{10}$ amine. In an embodiment, the amide compound can be a $C_3$ to $C_{30}$ amide; alternatively, a $C_3$ to $C_{20}$ amide; alternatively, $C_3$ to $C_{15}$ amide; or alternatively, a $C_3$ to $C_{10}$ amide. In an embodiment, the imide compound can be a $C_4$ to $C_{30}$ imide; alternatively, a $C_4$ to $C_{20}$ imide; alternatively, $C_4$ to $C_{15}$ imide; or alternatively, a $C_4$ to $C_{10}$ imide.

In an aspect, the pyrrole compound (also called the "pyrrole") which can be utilized in the catalyst systems disclosed herein can comprise any pyrrole compound that can form a chromium pyrrolide complex. As used in this disclosure, the term "pyrrole compound" refers to pyrrole ($C_5H_5N$), derivatives of pyrrole (e.g., indole), substituted pyrroles, as well as metal pyrrolide compounds. A pyrrole compound is defined as a compound comprising a 5-membered, nitrogen-containing heterocycle, such as, for example, pyrrole, derivatives of pyrrole, or combinations thereof. Broadly, the pyrrole compound can be pyrrole or any heteroleptic or homoleptic metal complex or salt containing a pyrrolide radical or ligand. Generally, the pyrrole compound can be a $C_4$ to $C_{30}$ pyrrole; alternatively, a $C_4$ to $C_{20}$ pyrrole; alternatively, $C_4$ to $C_{15}$ pyrrole; or alternatively, a $C_4$ to $C_{10}$ pyrrole.

In an aspect, the pyrrole compound which can be utilized in the catalyst systems disclosed herein can have Formula P1 or Formula I1. In an embodiment, the pyrrole compound which can be utilized in the catalyst systems disclosed herein can have Formula P1; or alternatively Formula I1.

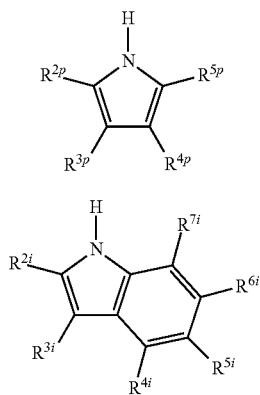

In an aspect, $R^{2p}$, $R^{3p}$, $R^{4p}$, and $R^{5p}$ of Formula P1 and $R^{2i}$, $R^{3i}$, $R^{4i}$, $R^{5i}$, $R^{6i}$, and $R^{7i}$ of Formula I1 can each independently be hydrogen, a $C_1$ to $C_{18}$ organyl group, or a $C_3$ to $C_{60}$ silyl group; alternatively, hydrogen, a $C_1$ to $C_{15}$ organyl group, or a $C_3$ to $C_{45}$ silyl group; alternatively, hydrogen, a $C_1$ to $C_{10}$ organyl group, or a $C_3$ to $C_{30}$ silyl group; alternatively, hydrogen, a $C_1$ to $C_5$ organyl group, or a $C_3$ to $C_{15}$ silyl group; alternatively, hydrogen, or a $C_1$ to $C_{18}$ organyl group; alternatively, hydrogen, or a $C_1$ to $C_{15}$ organyl group; alternatively, hydrogen, or a $C_1$ to $C_{10}$ organyl group; or alternatively, hydrogen, or a $C_1$ to $C_5$ organyl group. In an embodiment, $R^{2p}$, $R^{3p}$, $R^{4p}$, and $R^{5p}$ of Formula P1 and $R^{2i}$, $R^{3i}$, $R^{4i}$, $R^{5i}$, $R^{6i}$, and $R^{7i}$ of Formula I1 can each independently be hydrogen, a $C_1$ to $C_{18}$ hydrocarbyl group, or a $C_3$ to $C_{60}$ silyl group; alternatively, hydrogen, a $C_1$ to $C_{15}$ hydrocarbyl group, or a $C_3$ to $C_{45}$ silyl group; alternatively, hydrogen, a $C_1$ to $C_{10}$ hydrocarbyl group, or a $C_3$ to $C_{35}$ silyl group; alternatively, hydrogen, a $C_1$ to $C_5$ hydrocarbyl group, or a $C_3$ to $C_{15}$ silyl group; alternatively, hydrogen, or a $C_1$ to $C_{18}$ hydrocarbyl group; alternatively, hydrogen, or a $C_1$ to $C_{15}$ hydrocarbyl group; alternatively, hydrogen, or a $C_1$ to $C_{10}$ hydrocarbyl group; or alternatively, hydrogen, or a $C_1$ to $C_5$ hydrocarbyl group.

In an embodiment, the pyrrole compound which can be utilized in the catalyst systems disclosed herein can comprise, can consist essentially of, or can be, pyrrole, 2,5-dimethylpyrrole, 2-methyl-5-ethylpyrrole, 2-methyl-5-propylpyrrole, 2,5-diethylpyrrole, 3,4-dimethylpyrrole, 2,5-di-n-propylpyrrole, 2,5-di-n-butylpyrrole, 2,5-di-n-pentylpyrrole, 2,5-di-n-hexylpyrrole, 2,5-di-n-heptylpyrrole, 2,5-di-n-octylpyrrole, 2,5-dibenzylpyrrole, 2,4-dimethyl-3-ethylpyrrole, 2,3,5-triethylpyrrole, 2,3,5-tri-n-butylpyrrole, 2,3,5-tri-n-pentylpyrrole, 2,3,5-tri-n-hexylpyrrole, 2,3,5-tri-n-heptylpyrrole, 2,3,5-tri-n-octylpyrrole, 2,3,4,5-tetraethylpyrrole, 2,3,4,5-tetra-n-butylpyrrole, 2,3,4,5-tetra-n-hexylpyrrole, 2,5-bis(2',2',2'-trifluoroethyl)pyrrole, 2,5-bis(2'-methoxymethyl)pyrrole, 2-methyl-4-isopropylpyrrole, 2-ethyl-4-isopropylpyrrole, 2-methyl-4-sec-butylpyrrole, 2-ethyl-4-sec-butylpyrrole, 2-methyl-4-isobutylpyrrole, 2-ethyl-4-isobutylpyrrole, 2-methyl-4-t-butylpyrrole, 2-ethyl-4-t-butylpyrrole, 2-methyl-4-neopentylpyrrole, 2-ethyl-4-neopentylpyrrole, 3,4-diisopropylpyrrole, 3,4-di-sec-butylpyrrole, 3,4-diisobutylpyrrole, 3,4-di-t-butylpyrrole, 3,4-di-neopentylpropylpyrrole, tetrahydroindole, dipyrrolylmethane, indole, 3,4-dichloropyrrole, 2,3,4,5-tetrachloropyrrole, pyrrole-2-carboxylic acid, 2-acetylpyrrole, pyrrole-2-carboxaldehyde, 3-acetyl-2,4-dimethylpyrrole, ethyl-2,4-dimethyl-5-(ethoxycarbonyl)-3-pyrrole-propionate, or ethyl-3,5-dimethyl-2-pyrrolecarboxylate. In some embodiments, pyrrole compounds that can be used in the catalyst system disclosed herein comprise, but are not limited to pyrrole-2-carboxylic acid, 2-acetylpyrrole, pyrrole-2-carboxaldehyde, tetrahydroindole, 2,5-dimethylpyrrole, 2,4-dimethyl-3-ethylpyrrole, 3-acetyl-2,4-dimethylpyrrole, ethyl-2,4-dimethyl-5-(ethoxycarbonyl)-3-pyrrole-propionate, ethyl-3,5-dimethyl-2-pyrrolecarboxylate, 3,4-dichloropyrrole, 2,3,4,5-tetrachloropyrrole, 2-acetylpyrrole, pyrazole, pyrrolidine, indole, dipyrrolylmethane, or combinations thereof. In other embodiments, the pyrrole compound which can be utilized in the catalyst systems disclosed herein can comprise, can consist essentially of, or can be, pyrrole, 2,5-dimethylpyrrole, 2-methyl-5-ethylpyrrole, 2-methyl-5-propylpyrrole, 2,5-diethylpyrrole, or combinations thereof; alternatively, pyrrole; alternatively, 2,5-dimethylpyrrole; alternatively, 2-methyl-5-ethylpyrrole; alternatively, 2-methyl-5-propylpyrrole; or alternatively, 2,5-diethylpyrrole.

In an embodiment, the pyrrole compound which can be utilized in the catalyst systems disclosed herein can comprise a metal pyrrolide, such as an alkyl metal pyrrolide. In some embodiments, the pyrrole compound which can be utilized in the catalyst systems disclosed herein can comprise, individually or in any combination, a dialkylaluminum pyrrolide of any pyrrole provided herein. Alkyl groups will be described in more detail later herein (e.g., as alkyl groups for the metal alkyl) and these alkyl groups can be utilized to further describe the alkyl metal pyrrolide and/or the dialkylaluminum pyrrolide which can be utilized as the pyrrole compound which can be utilized in the catalyst systems disclosed herein. In other embodiments, the pyrrole compound which can be utilized in the catalyst systems disclosed herein can comprise diethylaluminum 2,5-dimethylpyrrolide, ethylaluminum di(2,5-dimethylpyrrolide), aluminum tri(2,5-dimethylpyrrolide), or combinations thereof.

In an embodiment, the heteroatomic ligand can be a diphosphino aminyl compound. A diphosphino aminyl compound is a compound having a moiety characterized by having a P—N—P (phosphorus-nitrogen-phosphorus) linkage. For purposes of the disclosure herein, the moiety having the P—N—P linkage can hereafter be referred to as a "PNP moiety" or as a "diphosphino aminyl moiety." Further, for purposes of the disclosure herein, the heteroatomic ligand comprising the diphosphino aminyl moiety can be referred to as a "PNP ligand," a "diphosphino aminyl ligand," or a "diphosphino aminyl compound."

In an embodiment, the heteroatomic ligand can comprise a diphosphino aminyl moiety having Structure PNP1:

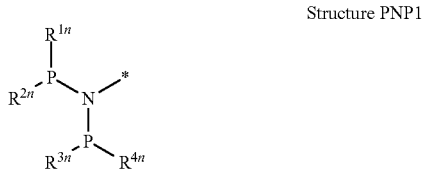

Structure PNP1 wherein $R^{1n}$, $R^{2n}$, $R^{3n}$, and $R^{4n}$ can be any group described herein and the undesignated aminyl nitrogen valence (*) represents the remainder of the heteroatomic ligand. In an embodiment, $R^{1n}$, $R^{2n}$, $R^{3n}$, and $R^{4n}$ can each be different. In some embodiments, $R^{1n}$, $R^{2n}$, $R^{3n}$, and $R^{4n}$ can each be the same. In other embodiments, $R^{1n}$ and $R^{2n}$ can be the same, and $R^{3n}$ and $R^{4n}$ can be the same, but different from $R^{1n}$ and $R^{2n}$. In yet other embodiments, $R^{1n}$ and $R^{3n}$ can be the same, and $R^{2n}$ and $R^{4n}$ can be the same, but different from $R^{1n}$ and $R^{3n}$.

In an embodiment, $R^{1n}$, $R^{2n}$, $R^{3n}$, and/or $R^{4n}$ of the diphosphino aminyl moiety independently can be a $C_1$ to $C_{30}$ alkyl group; alternatively, a $C_1$ to $C_{20}$ alkyl group; alternatively, a $C_1$ to $C_{15}$ alkyl group; alternatively, a $C_1$ to $C_{10}$ alkyl group; or alternatively, a $C_1$ to $C_5$ alkyl group. In yet other embodiments, $R^{1n}$, $R^{2n}$, $R^{3n}$, and/or $R^{4n}$ of the diphosphino aminyl moiety independently can be a $C_6$ to $C_{30}$ aromatic group; alternatively, a $C_6$ to $C_{20}$ aromatic group; alternatively, a $C_6$ to $C_{15}$ aromatic group; or alternatively, a $C_6$ to $C_{10}$ aromatic group. In still yet other embodiments, $R^{1n}$, $R^{2n}$, $R^{3n}$, and/or $R^{4n}$ of the diphosphino aminyl moiety independently can be a phenyl group or a $C_6$ to $C_{30}$ substituted phenyl group; alternatively, a phenyl group or a $C_6$ to $C_{20}$ substituted phenyl group; alternatively, a phenyl group or a $C_6$ to $C_{15}$ substituted phenyl group; alternatively, a phenyl group or a $C_6$ to $C_{10}$ substituted phenyl group; or alternatively, a phenyl group. In further embodiments, $R^{1n}$ and $R^{2n}$, and/or $R^{3n}$ and $R^{4n}$ of the diphosphino aminyl moiety can be joined to form a ring (regardless of particular type of group—organyl, organyl consisting of inert functional groups, hydrocarbyl, or any species within) containing a phosphorus atom of the diphosphino aminyl moiety. General substituent groups are provided herein and these general substituent groups can be utilized to further describe the substituted phenyl groups which can be utilized as $R^{1n}$ and $R^{2n}$, and/or $R^{3n}$ and $R^{4n}$ for the diphosphino aminyl moiety.

In an embodiment, $R^{1n}$, $R^{2n}$, $R^{3n}$, and $R^{4n}$ independently can be an organyl group; alternatively, an organyl group comprising inert functional groups; or alternatively, a hydrocarbyl group. In an embodiment, the organyl group which can be utilized as $R^{1n}$, $R^{2n}$, $R^{3n}$, and $R^{4n}$ can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In an embodiment, the organyl group comprising inert functional groups which can be utilized as $R^{1n}$, $R^{2n}$, $R^{3n}$, and $R^{4n}$ can be a $C_1$ to $C_{30}$ organyl group comprising inert functional groups; alternatively, a $C_1$ to $C_{20}$ organyl group comprising inert functional groups; alternatively, a $C_1$ to $C_{15}$ organyl group comprising inert functional groups; alternatively, a $C_1$ to $C_{10}$ organyl group comprising inert functional groups; or alternatively, a $C_1$ to $C_5$ organyl group comprising inert functional groups. In an embodiment, the hydrocarbyl group which can be utilized as $R^{1n}$, $R^{2n}$, $R^{3n}$, and $R^{4n}$ can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group. In further embodiments, two or more of $R^{1n}$, $R^{2n}$, $R^{3n}$, and $R^{4n}$ can be joined to form a ring or a ring system.

In an embodiment, the heteroatomic ligand can be a compound having an $N^2$-phosphinyl formamidine group. Generally, a formamidine group has the general structure

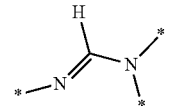

Within the formamidine group, the nitrogen participating in a double bond with the central carbon atom is referred to as the $N^1$ nitrogen atom and the nitrogen atom participating in a single bond with the central carbon atom is referred to as the $N^2$ nitrogen atom. Similarly, the groups attached to the $N^1$ and $N^2$ nitrogen atoms are referred to as the $N^1$ group and $N^2$ group, respectively. An $N^2$-phosphinyl formamidine group has the general structure

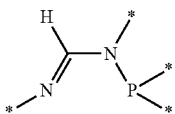

Within the $N^2$-phosphinyl formamidine group, the $N^1$ and $N^2$ nitrogen atoms and the $N^1$ and $N^2$ groups have the same meaning as described for the formamidine group. Consequently, an $N^2$-phosphinyl formamidine group has the phosphinyl group attached to the $N^2$ nitrogen atom.

In an embodiment, the heteroatomic ligand can be an $N^2$-phosphinyl formamidine compound having Structure NPF1. In an embodiment, a chromium containing compound complexed to an $N^2$-phosphinyl formamidine compound can have Structure NPFCr1.

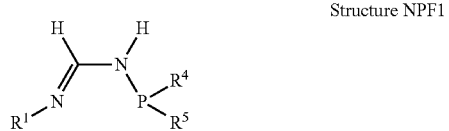

Structure NPF1

Structure NPFCr1

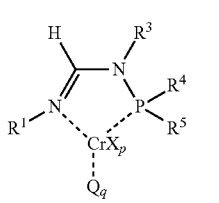

$R^1$, $R^3$, $R^4$, and $R^5$ within the $N^2$-phosphinyl formamidine compound having Structure NPF1 and an $N^2$-phosphinyl formamidine chromium complex (e.g., a chromium containing compound complexed to an $N^2$-phosphinyl formamidine compound) having Structure NPFCr1 are independently described herein and can be utilized without limitation to further describe the $N^2$-phosphinyl formamidine compound having Structure NPF1 and the $N^2$-phosphinyl formamidine chromium complex having Structure NPFCr1. $CrX_p$ represents the chromium containing compound of the $N^2$-phosphinyl formamidine chromium complex having Structure NPFCr1. Q represents an optional neutral ligand within the $N^2$-phosphinyl formamidine chromium complex having Structure NPFCr1, while q represents the number of optional neutral ligands present. $CrX_p$, Q, and q are independently described herein and can be utilized without limitation to further describe the $N^2$-phosphinyl formamidine chromium complex having Structure NPFCr1. Additionally, $CrX_p$, Q, and q can be combined with the independently described $R^1$, $R^3$, $R^4$, and $R^5$ to further describe the $N^2$-phosphinyl formamidine chromium complex having Structure NPFCr1.

In an embodiment, the heteroatomic ligand can be a compound having an $N^2$-phosphinyl amidine group. Generally, an amidine group has the general structure

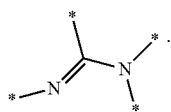

Within the amidine group, the nitrogen participating in a double bond with the central carbon atom is referred to as the $N^1$ nitrogen atom and the nitrogen atom participating in a single bond with the central carbon atom is referred to as the $N^2$ nitrogen atom. Similarly, the groups attached to the $N^1$ and $N^2$ nitrogen atoms are referred to as the $N^1$ group and $N^2$ group, respectively. An $N^2$-phosphinyl amidine group has the general structure

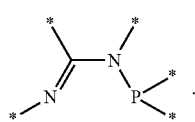

Within the $N^2$-phosphinyl amidine group, the $N^1$ and $N^2$ nitrogen atoms and the $N^1$ and $N^2$ groups have the same meaning as described for the amidine group. Consequently, an $N^2$-phosphinyl amidine group has the phosphinyl group attached to the $N^2$ nitrogen atom. Within the amidine group and $N^2$-phosphinyl amidine group, the carbon atom between the two nitrogen atoms is the central carbon atom and any substituent attached to it is referred to as the central carbon group. For the purpose of the disclosure herein, a compound having a pyridine group with a 2-amine group (or its analogues—e.g., a pyrimidine ring, an imidazole ring, a compound having 2-aminopyridine group, and the like) or having a 2-phosphinylamine group is not considered to constitute an amidine group or $N^2$-phosphinyl amidine group, respectively.

In an embodiment, the heteroatomic ligand (whether it is a separate component of the catalyst system or is a ligand complexed to the transition metal compound of the catalyst system) can be an $N^2$-phosphinyl amidine compound having Structure NPA1. In an embodiment, the chromium containing compound complexed to an $N^2$-phosphinyl amidine compound can have Structure NPACr1.

Structure NPA1

Structure NPACr1

$R^1$, $R^2$, $R^3$, $R^4$, and $R^5$ within the $N^2$-phosphinyl amidine compound having Structure NPA1 and an $N^2$-phosphinyl amidine chromium complex (e.g., a chromium containing compound complexed to an $N^2$-phosphinyl amidine compound) having Structure NPACr1 are independently described herein and can be utilized without limitation to further describe the $N^2$-phosphinyl amidine compound having Structure NPA1 and the $N^2$-phosphinyl amidine chromium complex having Structure NPACr1. $CrX_p$ represents the chromium containing compound of the $N^2$-phosphinyl amidine chromium complex having Structure NPACr1. Q represents an optional neutral ligand of the $N^2$-phosphinyl amidine chromium complex having Structure NPACr1, while q represents the number of optional neutral ligands present. $CrX_p$, Q, and q are independently described herein and can be utilized without limitation to further describe the $N^2$-phosphinyl amidine chromium complex having Structure NPACr1. Additionally, $CrX_p$, Q, and q can be combined with the independently described $R^1$, $R^2$, $R^3$, $R^4$, and $R^5$ to further describe the $N^2$-phosphinyl amidine chromium complex having Structure NPACr1.

In an embodiment, the heteroatomic ligand can be a compound having an $N^2$-phosphinyl guanidine group. Generally, a guanidine group has the general structure

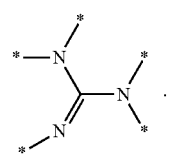

Within the guanidine core, the nitrogen participating in a double bond with the central carbon atom is referred to as the $N^1$ nitrogen atom and the two nitrogen atoms participating in a single bond with the central carbon atom are referred to as the N² nitrogen atom and the N³ nitrogen atom. Similarly, the groups attached to the N¹, N² and N³ nitrogen atoms are referred to as the N¹ group, N² group, and N³ group, respectively. An N²-phosphinyl guanidine group, such as those found in a ligand of the N²-phosphinyl guanidine complexes described herein, has the general structure

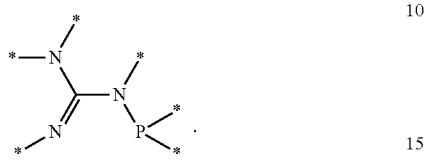

Within an N²-phosphinyl guanidine group, the nitrogen participating in a double bond with the central carbon atom of the guanidine core is referred to as the N¹ nitrogen atom, the nitrogen atom participating in a single bond with the central carbon atom of the guanidine core and a bond with the phosphorus atom of the phosphinyl group is referred to as the N² nitrogen atom, and the remaining nitrogen atom participating in a single bond with the central carbon atom of the guanidine core is referred to as the N³ nitrogen atom. It should be noted that a guanidine core or an N²-phosphinyl guanidine group can be a portion of a larger group (or compound) which does not contain guanidine in its name. For example, while the compound 7-dimethylphosphinylimidazo[1,2-a]imidazole could be classified as a compound having an imidazo[1,2-a]imidazole core (or a compound having a phosphinylimidazo[1,2-a]imidazole group), 7-dimethylphosphinylimidazo[1,2-a]imidazole would still be classified as a compound having a guanidine core (or as a compound having an N²-phosphinyl guanidine group) since it contains the defined general structure of the guanidine core (or the N²-phosphinyl guanidine group).

In an embodiment, an N²-phosphinyl guanidine compound can have Structure Gu1, Structure Gu2, Structure Gu3, Structure Gu4, or Structure Gu5; alternatively, Structure Gu1; alternatively, Structure Gu2; alternatively, Structure Gu3; alternatively, Structure Gu4; or alternatively, Structure Gu5. In an embodiment, an N²-phosphinyl guanidine chromium complex (e.g., a chromium containing compound complexed to an N²-phosphinyl guanidine compound) can have Structure GuCr1, Structure GuCr2, Structure GuCr3, Structure GuCr4, or Structure GuCr5; alternatively, Structure GuCr1; alternatively, Structure GuCr2; alternatively, Structure GuCr3; alternatively, Structure GuCr4; or alternatively, Structure GuCr5.

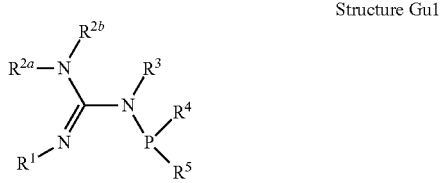

Structure Gu1

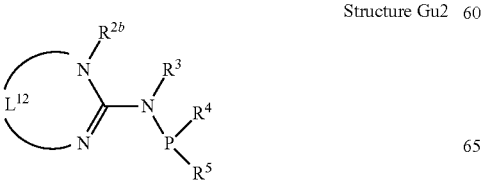

Structure Gu2

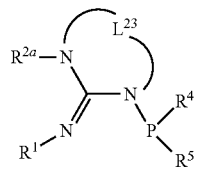

Structure Gu3

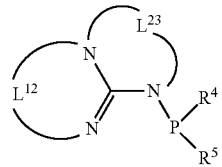

Structure Gu4

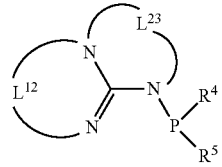

Structure Gu5

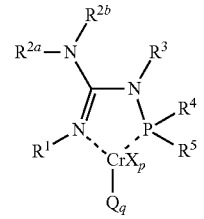

Structure GuCr1

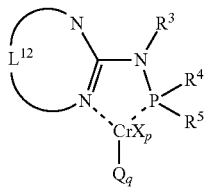

Structure GuCr2

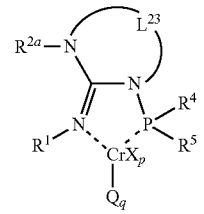

Structure GuCr3

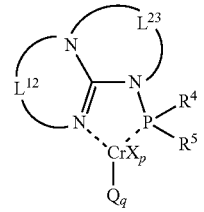

Structure GuCr4

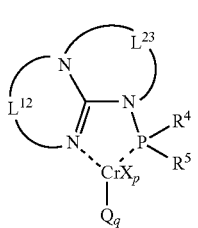

Structure GuCr5

$R^1$, $R^{2a}$, $R^{2b}$, $R^3$, $R^4$, $R^5$, $L^{12}$, and $L^{23}$, within the appropriate i) $N^2$-phosphinyl guanidine compound Structures Gu1, Gu2, Gu3, Gu4, and/or Gu5, and/or ii) $N^2$-phosphinyl guanidine chromium complex Structures GuCr1, GuCr2, GuCr3, GuCr4 and/or GuCr5 are independently described herein and can be utilized without limitation to further describe the appropriate i) $N^2$-phosphinyl guanidine compound Structures Gu1, Gu2, Gu3, Gu4, and/or Gu5, and/or ii) $N^2$-phosphinyl guanidine chromium complex Structures GuCr1, GuCr2, GuCr3, GuCr4, and/or GuCr5. $CrX_p$ within the $N^2$-phosphinyl guanidine chromium complex Structures GuCr1, GuCr2, GuCr3, GuCr4, and/or GuCr5 represents the chromium containing compound of the $N^2$-phosphinyl guanidine chromium complexes. Q represents an optional neutral ligand of the $N^2$-phosphinyl guanidine chromium complex Structures GuCr1, GuCr2, GuCr3, GuCr4, and/or GuCr5, while q represents the number of optional neutral ligands present. $CrX_p$, Q, and q are independently described herein and can be utilized without limitation to further describe the $N^2$-phosphinyl guanidine chromium complex Structures GuCr1, GuCr2, GuCr3, GuCr4, and/or GuCr5. Additionally, $CrX_p$, Q, and q can be combined with the independently described $R^1$, $R^{2a}$, $R^{2b}$, $R^3$, $R^4$, and $R^5$ to further describe the $N^2$-phosphinyl guanidine chromium complex Structures GuCr1, GuCr2, GuCr3, GuCr4, and/or GuCr5.

Generally, $R^1$ for the $N^2$-phosphinyl formamidine compounds, the $N^2$-phosphinyl formamidine chromium complexes, the $N^2$-phosphinyl amidine compounds, the $N^2$-phosphinyl amidine chromium complexes, the $N^2$-phosphinyl guanidine compounds, and/or the $N^2$-phosphinyl guanidine chromium complexes, which have an $R^1$ group can be an organyl group; alternatively, an organyl group consisting essentially of inert functional groups; or alternatively, a hydrocarbyl group. In some embodiments, the $R^1$ organyl group for the $N^2$-phosphinyl formamidine compounds, the $N^2$-phosphinyl formamidine chromium complexes, the $N^2$-phosphinyl amidine compounds, the $N^2$-phosphinyl amidine chromium complexes, the $N^2$-phosphinyl guanidine compounds, and/or the $N^2$-phosphinyl guanidine chromium complexes, which have an $R^1$ group can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In other embodiments, the $R^1$ organyl group consisting essentially of inert functional groups for the $N^2$-phosphinyl formamidine compounds, the $N^2$-phosphinyl formamidine chromium complexes, the $N^2$-phosphinyl amidine compounds, the $N^2$-phosphinyl amidine chromium complexes, the $N^2$-phosphinyl guanidine compounds, and/or the $N^2$-phosphinyl guanidine chromium complexes, which have an $R^1$ group can be a $C_1$ to $C_{30}$ organyl group consisting essentially of inert functional groups; alternatively, a $C_1$ to $C_{20}$ organyl group consisting essentially of inert functional groups; alternatively, a $C_1$ to $C_{15}$ organyl group consisting essentially of inert functional groups; alternatively, a $C_1$ to $C_{10}$ organyl group consisting essentially of inert functional groups; or alternatively, a $C_1$ to $C_5$ organyl group consisting essentially of inert functional groups. In yet other embodiments, the $R^1$ hydrocarbyl group for the $N^2$-phosphinyl formamidine compounds, the $N^2$-phosphinyl formamidine chromium complexes, the $N^2$-phosphinyl amidine compounds, the $N^2$-phosphinyl amidine chromium complexes, the $N^2$-phosphinyl guanidine compounds, and/or the $N^2$-phosphinyl guanidine chromium complexes, which have an $R^1$ group can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; alternatively, a $C_1$ to $C_5$ hydrocarbyl group; alternatively, a $C_1$ to $C_{30}$ alkyl group; alternatively, a $C_1$ to $C_{20}$ alkyl group; alternatively, a $C_1$ to $C_{15}$ alkyl group; alternatively, a $C_1$ to $C_{10}$ alkyl group; or alternatively, a $C_1$ to $C_5$ alkyl group. In still yet other embodiments, the $R^1$ group for the $N^2$-phosphinyl formamidine compounds, the $N^2$-phosphinyl formamidine chromium complexes, the $N^2$-phosphinyl amidine compounds, the $N^2$-phosphinyl amidine chromium complexes, the $N^2$-phosphinyl guanidine compounds, and/or the $N^2$-phosphinyl guanidine chromium complexes, which have an $R^1$ group can be a $C_3$ to $C_{30}$ aromatic group; alternatively, a $C_3$ to $C_{20}$ aromatic group; alternatively, a $C_3$ to $C_{15}$ aromatic group; or alternatively, a $C_3$ to $C_{10}$ aromatic group. In further embodiments, the $R^1$ group for the $N^2$-phosphinyl formamidine compounds, the $N^2$-phosphinyl formamidine chromium complexes, the $N^2$-phosphinyl amidine compounds, the $N^2$-phosphinyl amidine chromium complexes, the $N^2$-phosphinyl guanidine compounds, and/or the $N^2$-phosphinyl guanidine chromium complexes, which have an $R^1$ group can be a phenyl group or a $C_6$ to $C_{30}$ substituted phenyl group; alternatively, a phenyl group or a $C_6$ to $C_{20}$ substituted phenyl group; alternatively, a phenyl group or a $C_6$ to $C_{15}$ substituted phenyl group; or alternatively, a phenyl group or a $C_6$ to $C_{10}$ substituted phenyl group. General substituent groups are provided herein (and will be described in more detail later herein) and these general substituent groups can be utilized to further describe the substituted phenyl groups which can be utilized as $R^1$ for the $N^2$-phosphinyl formamidine compounds, the $N^2$-phosphinyl formamidine chromium complexes, the $N^2$-phosphinyl amidine compounds, the $N^2$-phosphinyl amidine chromium complexes, the $N^2$-phosphinyl guanidine compounds, and/or the $N^2$-phosphinyl guanidine chromium complexes.

Generally, $R^2$ for the $N^2$-phosphinyl amidine compounds and/or the $N^2$-phosphinyl amidine chromium complexes can be an organyl group; alternatively, an organyl group consisting essentially of inert functional groups; or alternatively, a hydrocarbyl group. In some embodiments, $R^2$ for the $N^2$-phosphinyl amidine compounds and/or the $N^2$-phosphinyl amidine chromium complexes can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In other embodiments, $R^2$ for the $N^2$-phosphinyl amidine compounds and/or the $N^2$-phosphinyl amidine chromium complexes can be a $C_1$ to $C_{30}$ organyl group consisting essentially of inert functional groups; alternatively, a $C_1$ to $C_{20}$ organyl group consisting essentially of inert functional groups; alternatively, a $C_1$ to $C_{15}$ organyl group consisting essentially of inert functional groups; alternatively, a $C_1$ to $C_{10}$ organyl group consisting essentially of inert functional groups; or alternatively, a $C_1$ to $C_5$ organyl group consisting essentially of inert functional groups. In yet other embodiments, $R^2$ for the N²-phosphinyl amidine compounds and/or the N²-phosphinyl amidine chromium complexes can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; alternatively, a $C_1$ to $C_5$ hydrocarbyl group; alternatively, a $C_1$ to $C_{30}$ alkyl group; alternatively, a $C_1$ to $C_{20}$ alkyl group; alternatively, a $C_1$ to $C_{15}$ alkyl group; alternatively, a $C_1$ to $C_{10}$ alkyl group; or alternatively, a $C_1$ to $C_5$ alkyl group. In still yet other embodiments, $R^2$ for the N²-phosphinyl amidine compounds and/or the N²-phosphinyl amidine chromium complexes can be a $C_3$ to $C_{30}$ aromatic group; alternatively, a $C_3$ to $C_{20}$ aromatic group; alternatively, a $C_3$ to $C_{15}$ aromatic group; or alternatively, a $C_3$ to $C_{10}$ aromatic group. In still yet other embodiments, $R^2$ for the N²-phosphinyl amidine compounds and/or the N²-phosphinyl amidine chromium complexes can be a phenyl group or a $C_6$ to $C_{30}$ substituted phenyl group; alternatively, a phenyl group or a $C_6$ to $C_{20}$ substituted phenyl group; alternatively, a phenyl group or a $C_6$ to $C_{15}$ substituted phenyl group; or alternatively, a phenyl group or a $C_6$ to $C_{10}$ substituted phenyl group. In further embodiments, $R^2$ for the N²-phosphinyl amidine compounds and/or the N²-phosphinyl amidine chromium complexes can be a benzyl group or a $C_6$ to $C_{30}$ substituted benzyl group; alternatively, a benzyl group or a $C_6$ to $C_{20}$ substituted benzyl group; alternatively, a benzyl group or a $C_6$ to $C_{15}$ substituted benzyl group; or alternatively, a benzyl group or a $C_6$ to $C_{10}$ substituted benzyl group. General substituent groups are provided herein and these general substituent groups can be utilized to further describe the substituted phenyl groups and/or substituted benzyl groups which can be utilized as $R^2$ for the N²-phosphinyl amidine compounds and/or the N²-phosphinyl amidine chromium complexes.

Generally, $R^{2a}$ and/or $R^{2b}$ for the N²-phosphinyl guanidine compounds and/or the N²-phosphinyl guanidine chromium complexes, which have an $R^{2a}$ and/or $R^{2b}$ group independently can be hydrogen or an organyl group; alternatively, hydrogen; or alternatively, an organyl group. In another aspect, $R^{2a}$ and/or $R^{2b}$ for the N²-phosphinyl guanidine compounds and/or the N²-phosphinyl guanidine chromium complexes, which have an $R^{2a}$ and/or $R^{2b}$ group independently can be hydrogen or an organyl group consisting essentially of inert functional groups; alternatively, hydrogen; or alternatively, an organyl group consisting essentially of inert functional groups. In an aspect, $R^{2a}$ and/or $R^{2b}$ for the N²-phosphinyl guanidine compounds and/or the N²-phosphinyl guanidine chromium complexes, which have an $R^{2a}$ and/or $R^{2b}$ group independently can be hydrogen or a hydrocarbyl group; alternatively, hydrogen; or alternatively, a hydrocarbyl group. In some embodiments, $R^{2a}$ and/or $R^{2b}$ organyl group for the N²-phosphinyl guanidine compounds and/or the N²-phosphinyl guanidine chromium complexes, which have an $R^{2a}$ and/or $R^{2b}$ organyl group independently can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In other embodiments, $R^{2a}$ and/or $R^{2b}$ organyl group consisting essentially of inert functional group for the N²-phosphinyl guanidine compounds and/or the N²-phosphinyl guanidine chromium complexes, which have an $R^{2a}$ and/or $R^{2b}$ organyl group consisting essentially of inert functional groups independently can be a $C_1$ to $C_{30}$ organyl group consisting essentially of inert functional groups; alternatively, a $C_1$ to $C_{20}$ organyl group consisting essentially of inert functional groups; alternatively, a $C_1$ to $C_{15}$ organyl group consisting essentially of inert functional groups; alternatively, a $C_1$ to $C_{10}$ organyl group consisting essentially of inert functional groups; or alternatively, a $C_1$ to $C_5$ organyl group consisting essentially of inert functional groups. In yet other embodiments, $R^{2a}$ and/or $R^{2b}$ hydrocarbyl group for the N²-phosphinyl guanidine compounds and/or the N²-phosphinyl guanidine chromium complexes, which have an $R^{2a}$ and/or $R^{2b}$ hydrocarbyl group independently can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; alternatively, a $C_1$ to $C_5$ hydrocarbyl group; alternatively, a $C_1$ to $C_{30}$ alkyl group; alternatively, a $C_1$ to $C_{20}$ alkyl group; alternatively, a $C_1$ to $C_{15}$ alkyl group; alternatively, a $C_1$ to $C_{10}$ alkyl group; or alternatively, a $C_1$ to $C_5$ alkyl group. In still yet other embodiments, $R^{2a}$ and/or $R^{2b}$ group for the N²-phosphinyl guanidine compounds and/or the N²-phosphinyl guanidine chromium complexes, which have an $R^{2a}$ and/or $R^{2b}$ group independently can be a $C_3$ to $C_{30}$ aromatic group; alternatively, a $C_3$ to $C_{20}$ aromatic group; alternatively, a $C_3$ to $C_{15}$ aromatic group; or alternatively, a $C_3$ to $C_{10}$ aromatic group. In further embodiments, $R^{2a}$ and/or $R^{2b}$ group for the N²-phosphinyl guanidine compounds and/or the N²-phosphinyl guanidine chromium complexes, which have an $R^{2a}$ and/or $R^{2b}$ group independently can be a phenyl group or a $C_6$ to $C_{30}$ substituted phenyl group; alternatively, a phenyl group or a $C_6$ to $C_{20}$ substituted phenyl group; alternatively, a phenyl group or a $C_6$ to $C_{15}$ substituted phenyl group; or alternatively, a phenyl group or a $C_6$ to $C_{10}$ substituted phenyl group. General substituent groups are provided herein and these general substituent groups can be utilized to further describe the substituted phenyl groups which can be utilized as $R^{2a}$ and/or $R^{2b}$ for the N²-phosphinyl guanidine compounds and/or the N²-phosphinyl guanidine chromium complexes.

In an aspect, $R^1$ and $R^{2a}$ of the N²-phosphinyl guanidine compounds and/or the N²-phosphinyl guanidine chromium complexes can be joined to form a group, $L^{12}$ (e.g., linking group $L^{12}$), wherein $L^{12}$, the $N^1$ nitrogen atom, and the $N^3$ nitrogen atom can form a ring or a ring system. In another aspect, $R^3$ and $R^{2b}$ of the N²-phosphinyl guanidine compounds and/or the N²-phosphinyl guanidine chromium complexes can be joined to form a group, $L^{23}$ (e.g., linking group $L^{23}$), wherein $L^{23}$, the $N^2$ nitrogen atom, and the $N^3$ nitrogen atom can form a ring or a ring system. In an embodiment, $L^{12}$ and/or $L^{23}$ group for the N²-phosphinyl guanidine compounds and/or the N²-phosphinyl guanidine chromium complexes, which have an $L^{12}$ and/or $L^{23}$ group independently can be an organylene group; alternatively, an organylene group consisting of inert functional groups; or alternatively, a hydrocarbylene group. The organylene group which can be utilized as an $L^{12}$ and/or $L^{23}$ group of the N²-phosphinyl guanidine compounds and/or the N²-phosphinyl guanidine chromium complexes, which have an $L^{12}$ and/or $L^{23}$ group independently can be a $C_2$ to $C_{20}$ organylene group; alternatively, a $C_2$ to $C_{15}$ organylene group; alternatively, a $C_2$ to $C_{10}$ organylene group; or alternatively, a $C_2$ to $C_5$ organylene group. The organylene group consisting of inert functional groups which can be utilized as an $L^{12}$ and/or $L^{23}$ group of the N²-phosphinyl guanidine compounds and/or the N²-phosphinyl guanidine chromium complexes, which have an $L^{12}$ and/or $L^{23}$ group can be a $C_2$ to $C_{20}$ organylene group consisting of inert functional groups; alternatively, a $C_2$ to $C_{15}$ organylene group consisting of inert functional groups; alternatively, a $C_2$ to $C_{10}$ organylene group consisting of inert functional groups; or alternatively, a $C_2$ to $C_5$ organylene group consisting of inert functional groups. The hydrocarbylene group which can be utilized as an $L^{12}$ and/or $L^{23}$ group of the $N^2$-phosphinyl guanidine compounds and/or the $N^2$-phosphinyl guanidine chromium complexes, which have an $L^{12}$ and/or $L^{23}$ group can be a $C_2$ to $C_{20}$ hydrocarbylene group; alternatively, a $C_2$ to $C_{15}$ hydrocarbylene group; alternatively, a $C_2$ to $C_{10}$ hydrocarbylene group; or alternatively, a $C_2$ to $C_5$ hydrocarbylene group.

In an embodiment, $L^{12}$ and/or $L^{23}$ can have any structure provided in Table 1. In some embodiments, $L^{12}$ and/or $L^{23}$ can have Structure 1L, Structure 2L, Structure 3L, Structure 4L, or Structure 5L. In some embodiments, $L^{12}$ and/or $L^{23}$ can have Structure 2L or Structure 3L; or alternatively, Structure 4L or Structure 5L. In other embodiments, $L^{12}$ and/or $L^{23}$ can have Structure 1L; alternatively, Structure 2L; alternatively, Structure 3L; alternatively, Structure 4L; or alternatively, Structure 5L. In yet other embodiments, $L^{12}$ or $L^{23}$ can have Structure 6L. It should be noted that when $L^{12}$ or $L^{23}$ has Structure 6L, the other group attached to the $N^3$ nitrogen atom of the guanidine group cannot be Structure 6L (but can be any other linking group having a single bond to both the $N^2$ and $N^3$ nitrogen atoms of the guanidine group) because $L^{12}$ and $L^{23}$ both having Structure 6L would lead to a cationic guanidine compound where $N^2$ or $N^3$ is tetravalent.

TABLE 1

Structures for Linking Groups $L^{12}$ and/or $L^{23}$.

| | |
|---|---|
| —$(CR^{L1}R^{L2})_m$— | Structure 1L |
| —$CR^{L3}R^{L4}$—$CR^{L5}R^{L6}$— | Structure 2L |
| —$CR^{L3}R^{L4}$—$CR^{L7}R^{L8}$—$CR^{L5}R^{L6}$— | Structure 3L |
| —$CR^{11L}$=$CR^{12L}$— | Structure 4L |
| 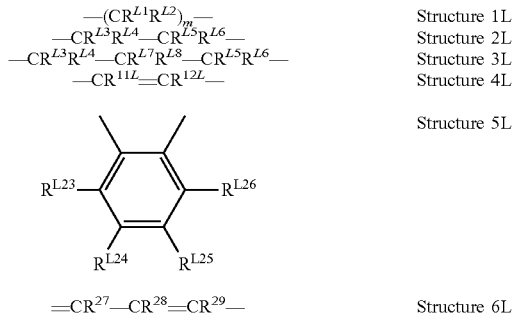 | Structure 5L |
| =$CR^{27}$—$CR^{28}$=$CR^{29}$— | Structure 6L |

Within the structures of Table 1, the undesignated valencies represent points at which $L^{12}$ and/or $L^{23}$, when present, attach to the respective nitrogen atoms of the $N^2$-phosphinyl guanidine compound and/or $N^2$-phosphinyl guanidine chromium complex. Generally, m can be an integer ranging from 2 to 5. In further embodiments, m can be 2 or 3; alternatively, m can be 2; or alternatively, m can be 3. $R^{L1}$ and $R^{L2}$ of the linking group having Structure 1L, $R^{L3}$, $R^{L4}$, $R^{L5}$, and $R^{L6}$ of the linking group having Structure 2L, $R^{L3}$, $R^{L4}$, $R^{L5}$, $R^{L6}$, $R^{L7}$, and $R^{L8}$ of the linking group having Structure 3L, $R^{L11}$ and $R^{L12}$ of the linking group having Structure 4L, $R^{L23}$, $R^{L24}$, $R^{L25}$, and $R^{L26}$ of the linking group having Structure 5L, $R^{L27}$, $R^{L28}$, and $R^{L29}$ of the linking group having Structure 6L independently can be a hydrogen or a non-hydrogen substituent group; or alternatively, hydrogen. Non-hydrogen substituent groups are independently disclosed herein and can be utilized without limitation to further describe the linking group having Structure 1L, Structure 2L, Structure 3L, Structure 4L, Structure 5L, and/or Structure 6L. In an embodiment, $L^{12}$ and/or $L^{23}$ can be an eth-1,2-ylene group (—$CH_2CH_2$—), an ethen-1,2-ylene group (—CH=CH—), a prop-1,3-ylene group (—$CH_2CH_2CH_2$—), a 1-methylethene-1,2-ylene group (—C($CH_3$)=CH—), a but-1,3-ylene group (—$CH_2CH_2CH$($CH_3$)—), a 3-methylbut-1,3-ylene group (—$CH_2CH_2C$($CH_3)_2$—), or a phen-1,2-ylene group. In some embodiments, $L^{12}$ and/or $L^{23}$ be an eth-1,2-ylene group (—$CH_2CH_2$—), a prop-1,3-ylene group (—$CH_2CH_2CH_2$—), a 1-methylethene-1,2-ylene group (—C($CH_3$)=CH—), a but-1,3-ylene group (—$CH_2CH_2CH$($CH_3$)—), or a 3-methylbut-1,3-ylene group (—$CH_2CH_2C$($CH_3)_2$—); alternatively, an eth-1,2-ylene group (—$CH_2CH_2$—), an ethen-1,2-ylene group (—CH=CH—), a prop-1,3-ylene group (—$CH_2CH_2CH_2$—), or a phen-1,2-ylene group; alternatively, an eth-1,2-ylene group (—$CH_2CH_2$—), or a prop-1,3-ylene group (—$CH_2CH_2CH_2$—); or alternatively, an ethen-1,2-ylene group (—CH=CH—), or a phen-1,2-ylene group. In other embodiments, $L^{12}$ and/or $L^{23}$ can be an eth-1,2-ylene group (—$CH_2CH_2$—); alternatively, an ethen-1,2-ylene group (—CH=CH—); alternatively, a prop-1,3-ylene group (—$CH_2CH_2CH_2$—); alternatively, a 1-methylethene-1,2-ylene group (—C($CH_3$)=CH—); alternatively, a but-1,3-ylene group (—$CH_2CH_2CH$($CH_3$)—); alternatively, a 3-methylbut-1,3-ylene group (—$CH_2CH_2C$($CH_3)_2$—); or alternatively, a phen-1,2-ylene group. In yet other embodiments, $L^{12}$ or $L^{23}$ can be a —CH=CH—CH=group. In an embodiment, $L^{12}$ can have a structure that can comprise at least one substituent located on the carbon atom attached to the $N^1$ nitrogen atom of the $N^2$-phosphinyl guanidine compound and/or the $N^2$-phosphinyl guanidine chromium complex; alternatively, can comprise only one substituent located on the carbon atom attached to the $N^1$ nitrogen atom of the $N^2$-phosphinyl guanidine compound and/or $N^2$-phosphinyl guanidine chromium complex; or alternatively, can comprise two substituents located on the carbon atom attached to the $N^1$ nitrogen atom of the $N^2$-phosphinyl guanidine compound and/or the $N^2$-phosphinyl guanidine chromium complex. In another embodiment, $L^{12}$ can have a structure that can consist of one substituent located on the carbon atom attached to the $N^1$ nitrogen atom of the $N^2$-phosphinyl guanidine compound and/or the $N^2$-phosphinyl guanidine chromium complex; or alternatively, can consist of two substituents located on the carbon atom attached to the $N^1$ nitrogen atom of the $N^2$-phosphinyl guanidine compound and/or $N^2$-phosphinyl guanidine chromium complex.

In an embodiment, $R^{2a}$ and $R^{2b}$ of the $N^2$-phosphinyl guanidine compounds and/or the $N^2$-phosphinyl guanidine chromium complexes can be joined to form a group, $L^{22}$ (e.g., linking group $L^{22}$), wherein $R^{2a}$, $R^{2b}$, and the $N^3$ nitrogen (or $L^{22}$ and the $N^3$ nitrogen) can form a ring or ring system. In an embodiment, $L^{22}$ of the $N^2$-phosphinyl guanidine compounds and/or the $N^2$-phosphinyl guanidine chromium complexes, which have an $L^{22}$ group can be an organylene group; alternatively, an organylene group consisting of inert functional groups; or alternatively, a hydrocarbylene group. The organylene group which can be utilized as $L^{22}$ of the $N^2$-phosphinyl guanidine compounds and/or the $N^2$-phosphinyl guanidine chromium complexes having an $L^{22}$ group can be a $C_3$ to $C_{20}$ organylene group; alternatively, a $C_3$ to $C_{15}$ organylene group; or alternatively, a $C_3$ to $C_{10}$ organylene group. The organylene group consisting of inert functional groups which can be utilized as $L^{22}$ of the $N^2$-phosphinyl guanidine compounds and/or the $N^2$-phosphinyl guanidine chromium complexes having an $L^{22}$ group can be a $C_3$ to $C_{20}$ organylene group consisting of inert functional groups; alternatively, a $C_3$ to $C_{15}$ organylene group consisting of inert functional groups; or alternatively, a $C_3$ to $C_{10}$ organylene group consisting of inert functional groups. The hydrocarbylene group which can be utilized as $L^{22}$ of the $N^2$-phosphinyl guanidine compounds and/or the $N^2$-phosphinyl guanidine chromium complexes having an $L^{22}$ group can be a $C_4$ to $C_{20}$ hydrocarbylene group; alternatively, a $C_4$ to $C_{15}$ hydrocarbylene group; or alternatively, a $C_4$ to $C_{10}$ hydrocarbylene group.

In an embodiment, $L^{22}$ can have any structure provided in Table 2. In some embodiments, $L^{22}$ can have Structure 11L, Structure 12L, Structure 13L, Structure 14L, or Structure 15L. In other embodiments, $L^{22}$ can have Structure 11L; alternatively, Structure 12L; alternatively, Structure 13L; alternatively, Structure 14L; or alternatively, Structure 15L.

TABLE 2

Structures for Linking Group $L^{22}$.

| | |
|---|---|
| —(CR$^{L31}$R$^{L32}$)$_n$— <br> Structure 11L | —CR$^{L41}$R$^{L42}$—CR$^{L45}$R$^{L46}$ CR$^{L47}$R$^{L48}$ CR$^{L43}$R$^{L44}$— <br> Structure 12L |
| —CR$^{L41}$R$^{L42}$—CR$^{L45}$R$^{L46}$—CR$^{L49}$R$^{L50}$—CR$^{L47}$R$^{L48}$—CR$^{L43}$R$^{L44}$— <br> Structure 13L | |
| —CR$^{L41}$R$^{L42}$—CR$^{L45}$R$^{L46}$—O—CR$^{L47}$R$^{L48}$—CR$^{L43}$R$^{L44}$— <br> Structure 14L | —CR$^{L51}$=CR$^{L53}$—CR$^{L54}$=CR$^{L52}$— <br> Structure 15L |

Within the structures of Table 2, the undesignated valencies represent points at which $L^{22}$ of the $N^2$-phosphinyl guanidine compound and/or the $N^2$-phosphinyl chromium complex, when present, attaches to the $N^3$ nitrogen atom of the $N^2$-phosphinyl chromium complex. Generally, n can be an integer ranging from 4 to 7. In further embodiments, n can be 4 or 5; alternatively, n can be 4; or alternatively, n can be 5. $R^{L31}$ and $R^{L32}$ of the linking group having Structure 11L, $R^{L41}$, $R^{L42}$, $R^{L43}$, $R^{L44}$, $R^{L45}$, $R^{L46}$, $R^{L47}$, and $R^{L48}$ of the linking group having Structure 12L, $R^{L41}$, $R^{L42}$, $R^{L43}$, $R^{L44}$, $R^{L45}$, $R^{L46}$, $R^{L47}$, $R^{L48}$, $R^{L49}$, and $R^{L50}$ of the linking group having Structure 13L, $R^{L41}$, $R^{L42}$, $R^{L43}$, $R^{L44}$, $R^{L45}$, $R^{L46}$, $R^{L47}$, and $R^{L48}$ of the linking group having Structure 14L, and $R^{L51}$, $R^{L52}$, $R^{L53}$, and $R^{L54}$ of the linking group having Structure 15L independently can be hydrogen or a non-hydrogen substituent group; or alternatively, hydrogen. Non-hydrogen substituent groups are independently disclosed herein and can be utilized without limitation to further describe the linking group having Structure 11L, Structure 12L, Structure 13L, Structure 14L, and/or Structure 15L. In an embodiment, $L^{22}$ can be a but-1,4-ylene group, a pent-1,4-ylene group, a pent-1,5-ylene group, a hex-2,5-ylene group, a hex-1,5-ylene group, a hept-2,5-ylene group, a buta-1,3-dien-1,4-ylene group, or a bis(eth-2-yl)ether group; alternatively, a but-1,4-ylene group, a pent-1,5-ylene group, or a bis(eth-2-yl)ether group; alternatively, a but-1,4-ylene group; alternatively, a pent-1,5-ylene group; alternatively, a buta-1,3-dien-1,4-ylene group; or alternatively, a bis(eth-2-yl)ether group.

Generally, $R^3$ of the $N^2$-phosphinyl formamidine compounds, the $N^2$-phosphinyl formamidine chromium complexes, the $N^2$-phosphinyl amidine compounds, the $N^2$-phosphinyl amidine chromium complexes, the $N^2$-phosphinyl guanidine compounds, and/or the $N^2$-phosphinyl guanidine chromium complexes, which have an $R^3$ group can be hydrogen or an organyl group; hydrogen or an organyl group consisting essentially of inert functional groups; alternatively, hydrogen or a hydrocarbyl group; alternatively, hydrogen; alternatively, an organyl group; alternatively, an organyl group consisting essentially of inert functional groups; or alternatively, a hydrocarbyl group. In some embodiments, the organyl group which can be utilized as $R^3$ of the $N^2$-phosphinyl formamidine compounds, the $N^2$-phosphinyl formamidine chromium complexes, the $N^2$-phosphinyl amidine compounds, the $N^2$-phosphinyl amidine chromium complexes, the $N^2$-phosphinyl guanidine compounds, and/or the $N^2$-phosphinyl guanidine chromium complexes, which have an $R^3$ group can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_m$ organyl group; or alternatively, a $C_1$ to $C_5$ organyl group. In other embodiments, the organyl group consisting of inert functional groups which can be utilized as $R^3$ of the $N^2$-phosphinyl formamidine compounds, the $N^2$-phosphinyl formamidine chromium complexes, the $N^2$-phosphinyl amidine compounds, the $N^2$-phosphinyl amidine chromium complexes, the $N^2$-phosphinyl guanidine compounds, and/or the $N^2$-phosphinyl guanidine chromium complexes, which have an $R^3$ group can be a $C_1$ to $C_{30}$ organyl group consisting essentially of inert functional groups; alternatively, a $C_1$ to $C_{20}$ organyl group consisting essentially of inert functional groups; alternatively, a $C_1$ to $C_{15}$ organyl group consisting essentially of inert functional groups; alternatively, a $C_1$ to $C_{10}$ organyl group consisting essentially of inert functional groups; or alternatively, a $C_1$ to $C_5$ organyl group consisting essentially of inert functional groups. In yet other embodiments, the hydrocarbyl group which can be utilized as $R^3$ of the $N^2$-phosphinyl formamidine compounds, the $N^2$-phosphinyl formamidine chromium complexes, the $N^2$-phosphinyl amidine compounds, the $N^2$-phosphinyl amidine chromium complexes, the $N^2$-phosphinyl guanidine compounds, and/or the $N^2$-phosphinyl guanidine chromium complexes, which have an $R^3$ group can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group. In still yet other embodiments, $R^3$ of the $N^2$-phosphinyl formamidine compounds, the $N^2$-phosphinyl formamidine chromium complexes, the $N^2$-phosphinyl amidine compounds, the $N^2$-phosphinyl amidine chromium complexes, the $N^2$-phosphinyl guanidine compounds, and/or the $N^2$-phosphinyl guanidine chromium complexes, which have an $R^3$ group can be a $C_1$ to $C_{30}$ alkyl group; alternatively, a $C_1$ to $C_{20}$ alkyl group; alternatively, a $C_1$ to $C_{15}$ alkyl group; alternatively, a $C_1$ to $C_{10}$ alkyl group; or alternatively, a $C_1$ to $C_5$ alkyl group. In still yet other embodiments, $R^3$ of the $N^2$-phosphinyl formamidine compounds, the $N^2$-phosphinyl formamidine chromium complexes, the $N^2$-phosphinyl amidine compounds, the $N^2$-phosphinyl amidine chromium complexes, the $N^2$-phosphinyl guanidine compounds, and/or the $N^2$-phosphinyl guanidine chromium complexes, which have an $R^3$ group can be a $C_3$ to $C_{30}$ aromatic group; alternatively, a $C_3$ to $C_{20}$ aromatic group; alternatively, a $C_3$ to $C_{15}$ aromatic group; or alternatively, a $C_3$ to $C_{10}$ aromatic group. In further embodiments, $R^3$ of the $N^2$-phosphinyl formamidine compounds, the $N^2$-phosphinyl formamidine chromium complexes, the $N^2$-phosphinyl amidine compounds, the $N^2$-phosphinyl amidine chromium complexes, the $N^2$-phosphinyl guanidine compounds, and/or the $N^2$-phosphinyl guanidine chromium complexes, which have an $R^3$ group can be a phenyl group or a $C_6$ to $C_{30}$ substituted phenyl group; alternatively, a phenyl group or a $C_6$ to $C_{20}$ substituted phenyl group; alternatively, a phenyl group or a $C_6$ to $C_{15}$ substituted phenyl group; or alternatively, a phenyl group or a $C_6$ to $C_{10}$ substituted phenyl group. General substituent groups are provided herein and these general substituent groups can be utilized to further describe the substituted phenyl groups which can be utilized as $R^3$ for the $N^2$-phosphinyl formamidine compounds, the $N^2$-phosphinyl formamidine chromium complexes, the $N^2$-phosphinyl amidine compounds, the $N^2$-phosphinyl amidine chromium complexes, the $N^2$-phosphinyl guanidine compounds, and/or the $N^2$-phosphinyl guanidine chromium complexes.

Generally, $R^4$ and/or $R^5$ of the $N^2$-phosphinyl formamidine compounds, the $N^2$-phosphinyl formamidine chromium complexes, the $N^2$-phosphinyl amidine compounds, the $N^2$-phosphinyl amidine chromium complexes, the $N^2$-phosphinyl guanidine compounds, and/or the $N^2$-phosphinyl guanidine chromium complexes independently can be an organyl group; alternatively, an organyl group consisting essentially of inert functional groups; or alternatively, a hydrocarbyl group. In some embodiments, $R^4$ and/or $R^5$ of the $N^2$-phosphinyl formamidine compounds, the $N^2$-phosphinyl formamidine chromium complexes, the $N^2$-phosphinyl amidine compounds, the $N^2$-phosphinyl amidine chromium complexes, the $N^2$-phosphinyl guanidine compounds, and/or the $N^2$-phosphinyl guanidine chromium complexes independently can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In other embodiments, $R^4$ and/or $R^5$ of the $N^2$-phosphinyl formamidine compounds, the $N^2$-phosphinyl formamidine chromium complexes, the $N^2$-phosphinyl amidine compounds, the $N^2$-phosphinyl amidine chromium complexes, the $N^2$-phosphinyl guanidine compounds, and/or the $N^2$-phosphinyl guanidine chromium complexes independently can be a $C_1$ to $C_{30}$ organyl group consisting essentially of inert functional groups; alternatively, a $C_1$ to $C_{20}$ organyl group consisting essentially of inert functional groups; alternatively, a $C_1$ to $C_{15}$ organyl group consisting essentially of inert functional groups; alternatively, a $C_1$ to $C_{10}$ organyl group consisting essentially of inert functional groups; or alternatively, a $C_1$ to $C_5$ organyl group consisting essentially of inert functional groups. In yet other embodiments, $R^4$ and/or $R^5$ of the $N^2$-phosphinyl formamidine compounds, the $N^2$-phosphinyl formamidine chromium complexes, the $N^2$-phosphinyl amidine compounds, the $N^2$-phosphinyl amidine chromium complexes, the $N^2$-phosphinyl guanidine compounds, and/or the $N^2$-phosphinyl guanidine chromium complexes independently can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group.

In other embodiments, $R^4$ and/or $R^5$ of the $N^2$-phosphinyl formamidine compounds, the $N^2$-phosphinyl formamidine chromium complexes, the $N^2$-phosphinyl amidine compounds, the $N^2$-phosphinyl amidine chromium complexes, the $N^2$-phosphinyl guanidine compounds, and/or the $N^2$-phosphinyl guanidine chromium complexes independently can be a $C_1$ to $C_{30}$ alkyl group; alternatively, a $C_1$ to $C_{20}$ alkyl group; alternatively, a $C_1$ to $C_{15}$ alkyl group; alternatively, a $C_1$ to $C_{10}$ alkyl group; or alternatively, a $C_1$ to $C_5$ alkyl group. In still yet other embodiments, $R^4$ and/or $R^5$ of the $N^2$-phosphinyl formamidine compounds, the $N^2$-phosphinyl formamidine chromium complexes, the $N^2$-phosphinyl amidine compounds, the $N^2$-phosphinyl amidine chromium complexes, the $N^2$-phosphinyl guanidine compounds, and/or the $N^2$-phosphinyl guanidine chromium complexes independently can be a $C_6$ to $C_{30}$ aromatic group; alternatively, a $C_6$ to $C_{20}$ aromatic group; alternatively, a $C_6$ to $C_{15}$ aromatic group; or alternatively, a $C_6$ to $C_{10}$ aromatic group. In still yet other embodiments, $R^4$ and/or $R^5$ of the $N^2$-phosphinyl formamidine compounds, the $N^2$-phosphinyl formamidine chromium complexes, the $N^2$-phosphinyl amidine compounds, the $N^2$-phosphinyl amidine chromium complexes, the $N^2$-phosphinyl guanidine compounds, and/or the $N^2$-phosphinyl guanidine chromium complexes independently can be a phenyl group or a $C_6$ to $C_{30}$ substituted phenyl group; alternatively, a phenyl group or a $C_6$ to $C_{20}$ substituted phenyl group; alternatively, a phenyl group or a $C_6$ to $C_{15}$ substituted phenyl group; alternatively, a phenyl group or a $C_6$ to $C_{10}$ substituted phenyl group; or alternatively, a phenyl group. In further embodiments, $R^4$ and $R^5$ of the $N^2$-phosphinyl formamidine compounds, the $N^2$-phosphinyl formamidine chromium complexes, the $N^2$-phosphinyl amidine compounds, the $N^2$-phosphinyl amidine chromium complexes, the $N^2$-phosphinyl guanidine compounds, and/or the $N^2$-phosphinyl guanidine chromium complexes can be joined to form a ring (regardless of particular type of group—organyl, organyl consisting of inert functional groups, hydrocarbyl, or any species within) containing the phosphorus atom of the $N^2$-phosphinyl formamidine compound, the $N^2$-phosphinyl formamidine chromium complex, the $N^2$-phosphinyl amidine compound, the $N^2$-phosphinyl amidine chromium complex, the $N^2$-phosphinyl guanidine compound, and/or the $N^2$-phosphinyl guanidine chromium complex. General substituent groups are provided herein and these general substituent groups can be utilized to further describe the substituted phenyl groups which can be utilized as $R^4$ and/or $R^5$ for the $N^2$-phosphinyl formamidine compounds, the $N^2$-phosphinyl formamidine chromium complexes, the $N^2$-phosphinyl amidine compounds, the $N^2$-phosphinyl amidine chromium complexes, the $N^2$-phosphinyl guanidine compounds, and/or the $N^2$-phosphinyl guanidine chromium complexes.

Various aspects and embodiments described herein refer to substituents or non-hydrogen substituents (or alternatively, substituent groups). Each substituent (alternatively, substituent group, or alternatively, general substituent group) or non-hydrogen substituent (or alternatively, non-hydrogen substituent group) can be a halide, a hydrocarbyl group, or a hydrocarboxy group; alternatively, a halide or a hydrocarbyl group; alternatively, a halide or a hydrocarboxy group; alternatively, a hydrocarbyl group or a hydrocarboxy group; alternatively, a halide; alternatively, a hydrocarbyl group; or alternatively, a hydrocarboxy group. In some embodiments, each substituent or non-hydrogen substituent of any aspect or embodiment calling for a substituent independently can be a halide, a $C_1$ to $C_{10}$ hydrocarbyl group, or a $C_1$ to $C_{10}$ hydrocarboxy group; alternatively, a halide or a $C_1$ to $C_{10}$ hydrocarbyl group; alternatively, a halide or a $C_1$ to $C_{10}$ hydrocarboxy group; alternatively, a $C_1$ to $C_{10}$ hydrocarbyl group or a $C_1$ to $C_{10}$ hydrocarboxy group; alternatively, a halide; alternatively, a $C_1$ to $C_{10}$ hydrocarbyl group; or alternatively, a $C_1$ to $C_{10}$ hydrocarboxy group. In other embodiments, each substituent or non-hydrogen substituent of any aspect or embodiment calling for a substituent independently can be a halide, a $C_1$ to $C_5$ hydrocarbyl group, or a $C_1$ to $C_5$ hydrocarboxy group; alternatively, a halide or a $C_1$ to $C_5$ hydrocarbyl group; alternatively, a halide or a $C_1$ to $C_5$ hydrocarboxy group; alternatively, a $C_1$ to $C_5$ hydrocarbyl group or a $C_1$ to $C_5$ hydrocarboxy group;

alternatively, a halide; alternatively, a $C_1$ to $C_5$ hydrocarbyl group; or alternatively, a $C_1$ to $C_5$ hydrocarboxy group.

In an embodiment, each halide substituent of any aspect or embodiment calling for a substituent or non-hydrogen substituent independently can be fluoride, chloride, bromide, or iodide; or alternatively, fluoride or chloride. In some embodiments, each halide substituent of any aspect or embodiment calling for a substituent or non-hydrogen substituent independently can be fluoride; alternatively, chloride; alternatively, bromide; or alternatively, iodide.

In an embodiment, each hydrocarbyl substituent of any aspect or embodiment calling for a substituent or non-hydrogen substituent independently can be an alkyl group, an aryl group, or an aralkyl group; alternatively, an alkyl group; alternatively, an aryl group; or alternatively, an aralkyl group. In some embodiments, each alkyl substituent of any aspect or embodiment calling for a substituent or non-hydrogen substituent independently can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In other embodiments, each aryl substituent of any aspect or embodiment calling for a substituent or non-hydrogen substituent independently can be a phenyl group, a tolyl group, a xylyl group, or a 2,4,6-trimethylphenyl group; alternatively, a phenyl group; alternatively, a tolyl group; alternatively, a xylyl group; or alternatively, a 2,4,6-trimethylphenyl group. In yet other embodiments, each aralkyl substituent of any aspect or embodiment calling for a substituent or non-hydrogen substituent independently can be a benzyl group or an ethylphenyl group (2-phenyleth-1-yl or 1-phenyleth-1-yl); alternatively, a benzyl group; alternatively, an ethylphenyl group; alternatively a 2-phenyleth-1-yl group; or alternatively, a 1-phenyleth-1-yl group.

In an embodiment, each hydrocarboxy substituent of any aspect or embodiment calling for a substituent or non-hydrogen substituent independently can be an alkoxy group, an aryloxy group, or an aralkoxy group; alternatively, an alkoxy group; alternatively, an aryloxy group; or alternatively, an aralkoxy group. In some embodiments, each alkoxy substituent of any aspect or embodiment calling for a substituent or non-hydrogen substituent independently can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In other embodiments, each aryloxy substituent of any aspect or embodiment calling for a substituent or non-hydrogen substituent independently can be a phenoxy group, a toloxy group, a xyloxy group, or a 2,4,6-trimethylphenoxy group; alternatively, a phenoxy group; alternatively, a toloxy group; alternatively, a xyloxy group; or alternatively, a 2,4,6-trimethylphenoxy group. In yet other embodiments, each aralkoxy substituent of any aspect or embodiment calling for a substituent or non-hydrogen substituent independently can be a benzoxy group.

Generally, the neutral ligand, Q, of the $N^2$-phosphinyl formamidine chromium complexes, the $N^2$-phosphinyl amidine chromium complexes, and/or the $N^2$-phosphinyl guanidine chromium complexes, if present, independently can be any neutral ligand that forms an isolatable compound with the $N^2$-phosphinyl formamidine chromium complexes, the $N^2$-phosphinyl amidine chromium complexes, and/or the $N^2$-phosphinyl guanidine chromium complexes. In an aspect, each neutral ligand independently can be a nitrile or an ether. In an embodiment, the neutral ligand can be a nitrile; or alternatively, an ether. The number of neutral ligands, q, of the $N^2$-phosphinyl formamidine chromium complexes, the $N^2$-phosphinyl amidine chromium complexes, and/or the $N^2$-phosphinyl guanidine chromium complexes can be any number that forms an isolatable compound with the $N^2$-phosphinyl formamidine chromium complexes, the $N^2$-phosphinyl amidine chromium complexes, and/or the $N^2$-phosphinyl guanidine chromium complexes. In an aspect, the number of neutral ligands can be from 0 to 6; alternatively, from 0 to 3; alternatively, 0; alternatively, 1; alternatively, 2; alternatively, 3; or alternatively, 4.

Generally, each neutral nitrile ligand independently can be a $C_2$ to $C_{20}$ nitrile; or alternatively, a $C_2$ to $C_{10}$ nitrile. In an embodiment, each neutral nitrile ligand independently can be a $C_2$ to $C_{20}$ aliphatic nitrile, a $C_7$ to $C_{20}$ aromatic nitrile, a $C_8$ to $C_{20}$ aralkane nitrile, or combinations thereof; alternatively, a $C_2$ to $C_{20}$ aliphatic nitrile; alternatively, a $C_7$ to $C_{20}$ aromatic nitrile; or alternatively, a $C_8$ to $C_{20}$ aralkane nitrile. In some embodiments, each neutral nitrile ligand independently can be a $C_2$ to $C_{10}$ aliphatic nitrile, a $C_7$ to $C_{10}$ aromatic nitrile, a $C_8$ to $C_{10}$ aralkane nitrile, or combinations thereof; alternatively, a $C_1$ to $C_{10}$ aliphatic nitrile; alternatively, a $C_7$ to $C_{10}$ aromatic nitrile; or alternatively, a $C_8$ to $C_{10}$ aralkane nitrile. In other embodiments, each neutral nitrile ligand independently can be acetonitrile, propionitrile, a butyronitrile, benzonitrile, or combinations thereof; alternatively, acetonitrile; alternatively, propionitrile; alternatively, a butyronitrile; or alternatively, benzonitrile.

Generally, each neutral ether ligand independently can be a $C_2$ to $C_{40}$ ether; alternatively, a $C_2$ to $C_{30}$ ether; or alternatively, a $C_2$ to $C_{20}$ ether. In an embodiment, each neutral ether ligand independently can be a $C_2$ to $C_{40}$ aliphatic ether, a $C_3$ to $C_{40}$ aliphatic cyclic ether, or a $C_4$ to $C_{40}$ aromatic cyclic ether; alternatively, a $C_2$ to $C_{40}$ aliphatic acyclic ether, or a $C_3$ to $C_{40}$ aliphatic cyclic ether; alternatively, a $C_2$ to $C_{40}$ aliphatic acyclic ether; alternatively, a $C_3$ to $C_{40}$ aliphatic cyclic ether; or alternatively, a $C_4$ to $C_{40}$ aromatic cyclic ether. In some embodiments, each neutral ether ligand independently can be a $C_2$ to $C_{30}$ aliphatic ether, a $C_3$ to $C_{30}$ aliphatic cyclic ether, or a $C_4$ to $C_{30}$ aromatic cyclic ether; alternatively, a $C_2$ to $C_{30}$ aliphatic acyclic ether, or a $C_3$ to $C_{30}$ aliphatic cyclic ether; alternatively, a $C_2$ to $C_{30}$ aliphatic acyclic ether; alternatively, a $C_3$ to $C_{30}$ aliphatic cyclic ether; or alternatively, a $C_4$ to $C_{30}$ aromatic cyclic ether. In other embodiments, each neutral ether ligand independently can be a $C_2$ to $C_{20}$ aliphatic ether, a $C_3$ to $C_{20}$ aliphatic cyclic ether, or a $C_4$ to $C_{20}$ aromatic cyclic ether; alternatively, a $C_2$ to $C_{20}$ aliphatic acyclic ether, or a $C_3$ to $C_{20}$ aliphatic cyclic ether; alternatively, a $C_2$ to $C_{20}$ aliphatic acyclic ether; alternatively, a $C_3$ to $C_{20}$ aliphatic cyclic ether; or alternatively, a $C_4$ to $C_{20}$ aromatic cyclic ether. In yet other embodiments, each neutral ether ligand independently can be dimethyl ether, diethyl ether, a dipropyl ether, a dibutyl ether, methyl ethyl ether, a methyl propyl ether, a methyl butyl ether, tetrahydrofuran, a dihydrofuran, 1,3-dioxolane, tetrahydropyran, a dihydropyran, a pyran, a dioxane, furan, benzofuran, isobenzofuran, dibenzofuran, diphenyl ether, a ditolyl ether, or combinations thereof; alternatively, dimethyl ether, diethyl ether, a dipropyl ether, a dibutyl ether, methyl ethyl ether, a methyl propyl ether, a methyl butyl ether, or combinations thereof; alternatively, tetrahydrofuran, a dihydrofuran, 1,3-dioxolane, tetrahydropyran, a dihydropyran, a pyran, a dioxane, or combinations thereof; alternatively, furan, benzofuran, isobenzofuran, dibenzofuran, or combinations thereof; alternatively, diphenyl ether, a ditolyl ether, or combinations thereof; alternatively, dimethyl ether; alternatively, diethyl ether; alternatively, a dipropyl ether; alternatively, a dibutyl ether; alternatively, methyl ethyl ether; alternatively, a methyl propyl ether; alternatively, a methyl butyl ether; alternatively, tetrahydrofuran; alternatively, a dihydrofuran; alternatively, 1,3-dioxolane; alternatively, tetrahydropyran; alternatively, a dihydropyran; alternatively, a pyran; alternatively, a dioxane; alternatively, furan; alternatively, benzofuran; alternatively, isobenzofuran; alternatively, dibenzofuran; alternatively, diphenyl ether; or alternatively, a ditolyl ether.

In an embodiment, the metal alkyl compound can be an alkylaluminum compound. In some embodiments, the alkylaluminum compound can be a trialkylaluminum compound, an alkylaluminum halide, an alkylaluminum alkoxide, an aluminoxane, or combinations thereof. In other embodiments, the alkylaluminum compound can be a trialkylaluminum compound, an alkylaluminum halide, an aluminoxane, or combinations thereof; alternatively, a trialkylaluminum compound, an alkylaluminum halide, or combinations thereof; or alternatively, a trialkylaluminum compound, an aluminoxane, or combinations thereof. In yet other embodiments, the alkylaluminum compound can be a trialkylaluminum compound; alternatively, an alkylaluminum halide; alternatively, an alkylaluminum alkoxide; or alternatively, an aluminoxane.

In an embodiment, the aluminoxane can have a repeating unit characterized by Formula I:

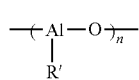

Formula I wherein R' can be a linear or branched alkyl group. Alkyl groups for metal alkyl compounds (or alternatively, alkylaluminum compounds) are independently described herein and can be utilized without limitation to further describe the aluminoxanes having Formula I. Generally, n of Formula I can be greater than 1; or alternatively, greater than 2. In an embodiment, n can range from 2 to 15; or alternatively, from 3 to 10.

In an aspect, each halide of any alkylaluminum halide disclosed herein independently can be fluoride, chloride, bromide, or iodide; or alternatively, chloride, bromide, or iodide. In an embodiment, each halide of any metal alkyl halide disclosed herein can be fluoride; alternatively, chloride; alternatively, bromide; or alternatively, iodide.

In an aspect, each alkyl group of any alkylaluminum compound disclosed herein (non-halide alkylaluminum compound or alkylaluminum halide) independently can be a $C_1$ to $C_{20}$ alkyl group; alternatively, a $C_1$ to $C_{10}$ alkyl group; or alternatively, a $C_1$ to $C_6$ alkyl group. In an embodiment, each alkyl group of any alkylaluminum compound disclosed herein (non-halide alkylaluminum compound or alkylaluminum halide) independently can be a methyl group, an ethyl group, a propyl group, a butyl group, a pentyl group, a hexyl group, a heptyl group, or an octyl group; or alternatively, a methyl group, an ethyl group, a butyl group, a hexyl group, or an octyl group. In some embodiments, each alkyl group of any alkylaluminum compound disclosed herein (non-halide alkylaluminum compound or alkylaluminum halide) independently can be a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group.

In an aspect, each alkoxide group of any alkylaluminum alkoxide disclosed herein independently can be a $C_1$ to $C_{20}$ alkoxy group; alternatively, a $C_1$ to $C_{10}$ alkoxy group; or alternatively, a $C_1$ to $C_6$ alkoxy group. In an embodiment, each alkoxide group of any alkylaluminum alkoxide disclosed herein independently can be a methoxy group, an ethoxy group, a propoxy group, a butoxy group, a pentoxy group, a hexoxy group, a heptoxy group, or an octoxy group; or alternatively, a methoxy group, an ethoxy group, a butoxy group, a hexoxy group, or an octoxy group. In some embodiments, each alkoxide group of any alkylaluminum alkoxide disclosed herein independently can be a methoxy group, an ethoxy group, an n-propoxy group, an n-butoxy group, an iso-butoxy group, an n-hexoxy group, or an n-octoxy group; alternatively, a methoxy group, an ethoxy group, an n-butoxy group, or an iso-butoxy group; alternatively, a methoxy group; alternatively, an ethoxy group; alternatively, an n-propoxy group; alternatively, an n-butoxy group; alternatively, an iso-butoxy group; alternatively, an n-hexoxy group; or alternatively, an n-octoxy group.

In an embodiment, the trialkylaluminum compound can comprise, can consist essentially of, or can be, trimethylaluminum, triethylaluminum, tripropylaluminum, tributylaluminum, trihexylaluminum, trioctylaluminum, or combinations thereof. In some embodiments, the trialkylaluminum compound can comprise, can consist essentially of, or can be trimethylaluminum, triethylaluminum, tripropylaluminum, tri-n-butylaluminum, tri-isobutylaluminum, trihexylaluminum, tri-n-octylaluminum, or combinations thereof; alternatively, triethylaluminum, tri-n-butylaluminum, tri-isobutylaluminum, trihexylaluminum, tri-n-octylaluminum, or combinations thereof; alternatively, triethylaluminum, tri-n-butylaluminum, trihexylaluminum, tri-n-octylaluminum, or combinations thereof. In other embodiments, the trialkylaluminum compound can comprise, can consist essentially of, or can be, trimethylaluminum; alternatively, triethylaluminum; alternatively, tripropylaluminum; alternatively, tri-n-butylaluminum; alternatively, tri-isobutylaluminum; alternatively, trihexylaluminum; or alternatively, tri-n-octylaluminum.

In an embodiment, the alkylaluminum halide can comprise, can consist essentially of, or can be, diethylaluminum chloride, diethylaluminum bromide, ethylaluminum dichloride, ethylaluminum sesquichloride, or combinations thereof. In some embodiments, the alkylaluminum halide can comprise, can consist essentially of, or can be, diethylaluminum chloride, ethylaluminum dichloride, ethylaluminum sesquichloride, or combinations thereof. In other embodiments, the alkylaluminum halide can comprise, can consist essentially of, or can be, diethylaluminum chloride;

alternatively, diethylaluminum bromide; alternatively, ethylaluminum dichloride; or alternatively, ethylaluminum sesquichloride.

In an embodiment, the aluminoxane can comprise, can consist essentially of, or can be, methylaluminoxane (MAO), ethylaluminoxane, modified methylaluminoxane (MMAO), n-propylaluminoxane, iso-propyl-aluminoxane, n-butylaluminoxane, sec-butylaluminoxane, iso-butylaluminoxane, t-butylaluminoxane, 1-pentyl-aluminoxane, 2-entylaluminoxane, 3-pentyl-aluminoxane, iso-pentyl-aluminoxane, neopentylaluminoxane, or combinations thereof. In some embodiments, the aluminoxane can comprise, can consist essentially of, or can be, methylaluminoxane (MAO), modified methylaluminoxane (MMAO), isobutyl aluminoxane, t-butyl aluminoxane, or combinations thereof. In other embodiments, the aluminoxane can comprise, can consist essentially of, or can be, methylaluminoxane (MAO); alternatively, ethylaluminoxane; alternatively, modified methylaluminoxane (MMAO); alternatively, n-propylaluminoxane; alternatively, iso-propyl-aluminoxane; alternatively, n-butylaluminoxane; alternatively, sec-butylaluminoxane; alternatively, iso-butylaluminoxane; alternatively, t-butyl aluminoxane; alternatively, 1-pentyl-aluminoxane; alternatively, 2-pentylaluminoxane; alternatively, 3-pentyl-aluminoxane; alternatively, iso-pentyl-aluminoxane; or alternatively, neopentylaluminoxane.

In an embodiment, the halogen containing compound can comprise a chloride containing compound, a bromide containing compound, an iodide containing compound, or combinations thereof. In some embodiments, the halogen containing compound, regardless of whether it is a chloride, bromide, or iodide containing compound, can comprise a metal halide, an alkyl metal halide, or an organic halide; alternatively, a metal halide; alternatively, an alkyl metal halide; or alternatively, an organic halide. In other embodiments, the halogen containing compound can comprise a group 3 metal halide, a group 4 metal halide, a group 5 metal halide, a group 13 metal halide, a group 14 metal halide, a group 15 metal halide, or combinations thereof. Non-limiting examples of halogen containing compounds suitable for use in the present disclosure as an optional component of the catalyst system include scandium chloride, yttrium chloride, lanthanum chloride, titanium tetrachloride, zirconium tetrachloride, hafnium tetrachloride, boron trichloride, aluminum chloride, gallium chloride, silicon tetrachloride, trimethyl chlorosilane, germanium tetrachloride, tin tetrachloride, phosphorus trichloride, antimony trichloride, antimony pentachloride, bismuth trichloride, boron tribromide, aluminum tribromide, silicon tetrachloride, silicon tetrabromide, aluminum fluoride, molybdenum pentachloride, tungsten hexachloride, trityl hexachloroantimonate, or combinations thereof.

In some embodiments, the halogen containing compound can comprise a dialkylaluminum halide, an alkylaluminum dihalide, an alkylaluminum sesquihalide, or combinations thereof. In other embodiments, the halogen containing compound can comprise diethylaluminum chloride, ethylaluminum sesquichloride, ethylaluminum dichloride, tributyltin chloride, dibutyltin dichloride, or combinations thereof; or alternatively, diethylaluminum chloride, ethylaluminum sesquichloride, ethylaluminum dichloride, or combinations thereof. In yet other embodiments, the halogen containing compound can comprise a $C_1$ to $C_{15}$ organic halide; alternatively, a $C_1$ to $C_{10}$ organic halide; or alternatively, a $C_1$ to $C_8$ organic halide. Non-limiting examples of halogen containing compounds suitable for use in the present disclosure as an optional component of the catalyst system include carbon tetrachloride, carbon tetrabromide, chloroform, bromoform, dichloromethane, dibromoethane, diiodomethane, chloromethane, bromomethane, iodomethane, dichloroethane, tetrachloroethane, trichloroacetone, hexachloroacetone, hexachlorocyclohexane, 1,3,5-trichlorobenzene, hexachlorobenzene, trityl chloride, benzyl chloride, benzyl bromide, benzyl iodide, chlorobenzene, bromobenzene, iodobenzene, hexafluorobenzene, or combinations thereof.

In an aspect, the catalyst system which can be utilized to produce the compositions disclosed herein can be selected from a catalyst system comprising a) a chromium containing compound, a pyrrole compound, a metal alkyl compound, and optionally a halide containing compound, b) a chromium containing compound, a diphosphino aminyl compound, and a metal alkyl compound, c) a chromium containing compound complexed to a diphosphino aminyl compound, and a metal alkyl compound, d) a chromium containing compound, an $N^2$-phosphinyl amidine compound, and a metal alkyl compound, e) a chromium containing compound complexed to an $N^2$-phosphinyl amidine compound, and a metal alkyl compound, f) a chromium containing compound, an $N^2$-phosphinyl formamidine compound, and a metal alkyl compound, g) a chromium containing compound complexed to an $N^2$-phosphinyl formamidine compound, and a metal alkyl compound, h) a chromium containing compound, an $N^2$-phosphinyl guanidine compound, and a metal alkyl compound, i) a chromium containing compound complexed to an $N^2$-phosphinyl guanidine compound, and a metal alkyl compound, and j) combinations thereof.

In an aspect, the catalyst system which can be utilized to produce the compositions disclosed herein can be selected from the group consisting of a) a chromium containing compound, a pyrrole compound, an alkylaluminum compound, and optionally a halide containing compound, b) a chromium containing compound, a diphosphino aminyl compound, and an alkylaluminum compound, c) a chromium containing compound complexed to a diphosphino aminyl compound, and an alkylaluminum compound, d) a chromium containing compound, an $N^2$-phosphinyl amidine compound, and an alkylaluminum compound, e) a chromium containing compound complexed to an $N^2$-phosphinyl amidine compound, and an alkylaluminum compound, f) a chromium containing compound, an $N^2$-phosphinyl formamidine compound, and an alkylaluminum compound, g) a chromium containing compound complexed to an $N^2$-phosphinyl formamidine compound, and an alkylaluminum compound, h) a chromium containing compound, an $N^2$-phosphinyl guanidine compound, and an alkylaluminum compound, i) a chromium containing compound complexed to an $N^2$-phosphinyl guanidine compound, and an alkylaluminum compound, and j) combinations thereof.

In an embodiment, the catalyst system can comprise i) a chromium containing compound, ii) an amine, amide, or imide compound, iii) an alkylaluminum compound, and iv) optionally a halide containing compound. In some embodiments, the catalyst system can comprise i) a chromium containing compound, ii) a pyrrole compound, iii) an alkylaluminum compound, and iv) optionally a halide containing compound. For purposes of the disclosure herein, the catalyst systems using a pyrrole compound can be referred to as a "chromium-pyrrole catalyst systems." The chromium-pyrrole catalyst system can be an ethylene trimerization catalyst system wherein the oligomer product (or trimerization product) typically comprises at least 70 wt. % hexenes. In some chromium-pyrrole catalyst system embodiments, the chromium containing compound can comprise, or consist essentially of, a chromium carboxylate; and the alkylaluminum compound can comprise, or consist essentially of, a trialkylaluminum compound, a dialkylaluminum halide, an alkylaluminum dihalide, an alkylaluminum sesquihalide, or combinations thereof. In some chromium-pyrrole catalyst system embodiments, the optional halide containing compound can be an organo halide compound, a metal halide compound (e.g., an inorganic metal halide compound or an alkyl metal halide compound), or combinations thereof. In a chromium-pyrrole catalyst system embodiment, the catalyst system can comprise chromium(III) 2-ethylhexanoate, 2,5-dimethyl pyrrole, triethylaluminum, and diethylaluminum chloride. Additional information regarding the use of chromium-pyrrole catalyst systems for trimerizing ethylene (including specific examples) can be found in, but not limited to, EP 608447A1; EP 706983A1; U.S. Pat. Nos. 5,198,563; 5,288,823; 5,331,104; 5,340,785; 5,360,879; 5,376,612; 5,382,738; 5,399,539; 5,438,027; 5,470,926; 5,543,375; 5,523,507; 5,563,312; 5,689,028; 5,750,816; 5,763,723; 5,814,575; 5,856,257; 5,856,612; 5,859,303; 5,910,619; 6,133,495; 6,380,451; 6,455,648; 7,157,612; 7,384,886; 7,476,775; 7,718,838; 7,820,581; 7,910,670; 8,049,052; 8,329,608; 8,344,198; 8,471,085; and U.S. Publication Nos. 2010/0036185; 2010/0113257; 2010/0113851; 2010/0113852; 2010/0331503; 2013/0150605; and 2013/0150642.

In another embodiment, the catalyst system can comprise i) a chromium containing compound, ii) a diphosphino aminyl compound, and iii) an alkylaluminum compound; or alternatively, i) a chromium containing compound complexed to a diphosphino aminyl compound, and ii) an alkylaluminum compound. For purposes of the disclosure herein, the catalyst systems using a diphosphino aminyl compound can be generically referred to as "chromium-PNP catalyst systems." Depending upon the diphosphino aminyl compound, the chromium-PNP catalyst systems can be an ethylene tetramerization catalyst system wherein the oligomer product (or tetramerization product) comprises at least 70 wt. % octenes; or a trimerization and tetramerization catalyst system wherein the oligomer product (or trimerization and tetramerization product) comprises at least 70 wt. % hexenes and octenes. In some chromium-PNP catalyst system embodiments, the chromium containing compound of the catalyst system or the chromium containing compound of the chromium containing compound complexed to a diphosphino aminyl compound of the catalyst system, can comprise, or consist essentially of, a chromium halide, carboxylate, β-diketonate, hydrocarboxide, nitrate, sulfate, phosphate, or chlorate; alternatively, a chromium halide, carboxylate, or β-diketonate; alternatively, a chromium halide; alternatively, a chromium carboxylate; or alternatively, chromium β-diketonate. In some chromium-PNP catalyst system embodiments, the alkylaluminum compound can comprise, or consist essentially of, a trialkylaluminum compound, an alkylaluminum halide (e.g., a dialkylaluminum halide, an alkylaluminum dihalide, and/or an alkylaluminum sesquihalide), an aluminoxane, or combinations thereof; or alternatively, an aluminoxane. Additional information regarding the use of chromium-PNP catalyst systems for trimerizing, or trimerizing and tetramerizing ethylene (including specific examples) can be found in, but not limited to, WO 2013013300; U.S. Pat. Nos. 7,285,607; 7,297,832; 7,323,524; 7,378,537; 7,511,183; 7,525,009; 7,829,749; 7,906,681; 7,964,763; 7,994,363; 8,076,523; 8,134,038; 8,252,956; 8,252,955; 8,268,941; 8,334,420; 8,367,786; 8,461,406; and U.S. Publication Nos. 2009/0306442; 2011/0257350; 2011/0282016; 2012/0041241; 2012/0088933; 2012/0101321; 2012/0142989; 2012/0199467; 2012/0271087; and 2012/0316303.

In yet another embodiment, the catalyst system can comprise i) a chromium containing compound, ii) an $N^2$-phosphinyl amidine compound, and iii) an alkylaluminum compound; or alternatively, i) a chromium containing compound complexed to an $N^2$-phosphinyl amidine compound, and ii) an alkylaluminum compound. For purposes of the disclosure herein, the catalyst systems using an $N^2$-phosphinyl amidine compound can be generically referred to as "chromium-$N^2$-phosphinyl amidine catalyst systems." Depending upon the $N^2$-phosphinyl amidine compound, the chromium-$N^2$-phosphinyl amidine catalyst systems can be an ethylene trimerization catalyst system wherein the oligomer product (or trimerization product) comprises at least 70 wt. % hexenes; or a trimerization and tetramerization catalyst system wherein the oligomer product (or trimerization and tetramerization product) comprises at least 70 wt. % hexenes and octenes. In some chromium-$N^2$-phosphinyl amidine catalyst system embodiments, the chromium containing compound of the catalyst system or the chromium containing compound of the chromium containing compound complexed to an $N^2$-phosphinyl amidine compound of the catalyst system, can comprise, or consist essentially of, a chromium halide, carboxylate, β-diketonate, hydrocarboxide, nitrate, or chlorate; alternatively, a chromium halide, carboxylate, hydrocarboxide, or β-diketonate; alternatively, a chromium halide; alternatively, a chromium carboxylate; alternatively, a chromium hydrocarboxide; or alternatively, chromium β-diketonate. In some chromium-$N^2$-phosphinyl amidine catalyst system embodiments, the alkylaluminum compound can comprise, or consist essentially of, a trialkylaluminum compound, an alkylaluminum halide (e.g., a dialkylaluminum halide, an alkylaluminum dihalide, and/or an alkylaluminum sesquihalide), an alkylaluminum alkoxide, an aluminoxane, or combinations thereof; or alternatively, an aluminoxane. Additional information regarding the use of chromium-$N^2$-phosphinyl amidine catalyst systems for trimerizing, or trimerizing and tetramerizing ethylene (including specific examples) can be found in, but not limited to, U.S. Pat. No. 8,680,003.

In still yet another embodiment, the catalyst system can comprise i) a chromium containing compound, ii) an $N^2$-phosphinyl formamidine compound, and iii) an alkylaluminum compound; or alternatively, i) a chromium containing compound complexed to an $N^2$-phosphinyl formamidine compound, and ii) an alkylaluminum compound. For purposes of the disclosure herein, the catalyst systems using an $N^2$-phosphinyl formamidine compound can be generically referred to as "chromium containing compound-$N^2$-phosphinyl formamidine catalyst systems." Depending upon the $N^2$-phosphinyl formamidine compound, the chromium containing compound-$N^2$-phosphinyl formamidine catalyst systems can be an ethylene trimerization catalyst system wherein the oligomer product (or trimerization product) comprises at least 70 wt. % hexenes; or a trimerization and tetramerization catalyst system wherein the oligomer product (or trimerization and tetramerization product) comprises at least 70 wt. % hexenes and octenes. In some chromium-$N^2$-phosphinyl formamidine catalyst system embodiments, the chromium containing compound of the catalyst system or the chromium containing compound of the chromium containing compound complexed to an $N^2$-phosphinyl formamidine compound of the catalyst system, can comprise, or consist essentially of, a chromium halide, carboxylate, β-diketonate, hydrocarboxide, nitrate, or chlorate; alternatively, a chromium halide, carboxylate, hydrocarboxide, or β-diketonate; alternatively, a chromium halide; alternatively, a chromium carboxylate; alternatively, a chromium hydrocarboxide; or alternatively, chromium β-diketonate. In some chromium-$N^2$-phosphinyl formamidine catalyst system embodiments, the alkylaluminum compound can comprise, or consist essentially of, a trialkylaluminum compound, an alkylaluminum halide (e.g., a dialkylaluminum halide, an alkylaluminum dihalide, and/or an alkylaluminum sesquihalide), an alkylaluminum alkoxide, an aluminoxane, or combinations thereof; or alternatively, an aluminoxane. Additional information regarding the use of the chromium containing compound-$N^2$-phosphinyl formamidine catalyst systems for trimerizing, or trimerizing and tetramerizing, ethylene (including specific examples) can be found in, but not limited to, PCT Patent Application PCT/US13/75936.

In still yet another embodiment, the catalyst system can comprise i) a chromium containing compound, ii) an $N^2$-phosphinyl guanidine compound, and iii) an alkylaluminum compound; or alternatively, i) a chromium containing compound complexed to an $N^2$-phosphinyl guanidine compound, and ii) an alkylaluminum compound. For purposes of the disclosure herein, the catalyst systems using an $N^2$-phosphinyl guanidine compound can be generically referred to as "chromium containing compound-$N^2$-phosphinyl guanidine catalyst systems." Depending upon the $N^2$-phosphinyl guanidine compound, the chromium containing compound-$N^2$-phosphinyl guanidine catalyst systems can be an ethylene trimerization catalyst system wherein the oligomer product (or trimerization product) comprises at least 70 wt. % hexenes; or a trimerization and tetramerization catalyst system wherein the oligomer product (or trimerization and tetramerization product) comprises at least 70 wt. % hexenes and octenes. In some chromium-$N^2$-phosphinyl guanidine catalyst system embodiments, the chromium containing compound of the catalyst system or the chromium containing compound of the chromium containing compound complexed to an $N^2$-phosphinyl guanidine compound of the catalyst system, can comprise, can consist essentially of, or can be, a chromium halide, carboxylate, β-diketonate, hydrocarboxide, nitrate, or chlorate; alternatively, a chromium halide, carboxylate, hydrocarboxide, or β-diketonate; alternatively, a chromium halide; alternatively, a chromium carboxylate; alternatively, a chromium hydrocarboxide; or alternatively, chromium β-diketonate. In some chromium-$N^2$-phosphinyl guanidine catalyst system embodiments, the alkylaluminum compound can comprise, or consist essentially of, a trialkylaluminum compound, an alkylaluminum halide (e.g., a dialkylaluminum halide, an alkylaluminum dihalide, and/or an alkylaluminum sesquihalide), an alkylaluminum alkoxide, an aluminoxane, or combinations thereof; or alternatively, an aluminoxane. Additional information regarding the use of chromium containing compound-$N^2$-phosphinyl guanidine catalyst systems for trimerizing, or trimerizing and tetramerizing, ethylene (including specific examples) can be found in, but not limited to, U.S. Publication No. 2013/0331629.

Combinations of more than one catalyst systems described herein can be employed, if desired. Moreover, the processes disclosed herein are not limited solely to the catalyst systems provided hereinabove.

In an embodiment, the catalyst system can be prepared by contacting the catalyst system with hydrogen. In the process embodiments disclosed herein, hydrogen can be added to the reaction system to accelerate the reaction and/or increase catalyst system activity. If desired, hydrogen can also be added to suppress polymer production. When hydrogen is utilized, a hydrogen partial pressure at which the oligomer product can be formed can range from 2 psi to 100 psi; alternatively, 5 psi to 75 psi; or alternatively, 10 psi to 50 psi.

In an embodiment, the catalyst system can be prepared in an optional catalyst system solvent. In some embodiments, the oligomer product can be formed in an optional reaction system diluent. In some embodiments, the catalyst system solvent and reaction system diluent can be the same; or alternatively, the catalyst system solvent and reaction system diluent can be different. Catalyst system solvents and reaction system diluents are independently provided herein and can be utilized without limitation to further describe the optional catalyst system solvent utilized for preparing the catalyst system and the reaction system diluent in which the oligomer product can be formed.

In some embodiments, the compositions disclosed herein can be prepared by a process comprising a) contacting 1) ethylene, 2) the catalyst system comprising i) a chromium containing compound, ii) a heteroatomic ligand, and iii) an alkylaluminum compound, and 3) optionally a reaction system diluent; b) forming an oligomer product comprising 1-hexene and/or 1-octene in a reaction system; c) discharging a reaction system effluent from the reaction system; d) contacting the reaction system effluent with a catalyst system deactivating agent; and e) isolating the composition. In an embodiment, the process can comprise a) contacting 1) ethylene, 2) the catalyst system comprising i) a chromium containing compound, ii) a heteroatomic ligand, and iii) an alkylaluminum compound, and 3) optionally a reaction system diluent; b) forming an oligomer product comprising 1-hexene and/or 1-octene in a reaction system; c) discharging a reaction system effluent from the reaction system; d) contacting the reaction system effluent with a catalyst system deactivating agent; and e) isolating a composition comprising (a) at least 76 mol %, at least 78 mol %, at least 80 mol %, or at least 82 mol % $C_{10}$ monoolefins, the $C_{10}$ monoolefins comprising (i) at least 3 mol %, at least 4 mol %, at least 5 mol %, at least 6 mol %, at least 7 mol %, or at least 8 mol % 2-butyl-1-hexene, (ii) at least 8 mol %, at least 9 mol %, at least 10 mol %, at least 11 mol %, at least 12 mol %, or at least 13 mol % 3-propyl-1-heptene, (iii) at least 6 mol %, at least 7 mol %, at least 8 mol %, at least 9 mol %, at least 10 mol %, or at least 11 mol % 4-ethyl-1-octene, and (iv) at least 20 mol %, at least 22 mol %, at least 24 mol %, at least 26 mol %, at least 28 mol %, or at least 30 mol % 5-methyl-1-nonene, and (b) at least 1 mol %, at least 2 mol %, at least 3 mol %, or at least 4 mol % $C_{14}$ monoolefins. In another embodiment, the process can comprise a) contacting 1) ethylene, 2) the catalyst system comprising i) a chromium containing compound, ii) a heteroatomic ligand, and iii) an alkylaluminum compound, and 3) optionally a reaction system diluent; b) forming an oligomer product comprising 1-hexene and/or 1-octene in a reaction system; c) discharging a reaction system effluent from the reaction system; d) contacting the reaction system effluent with a catalyst system deactivating agent; and e) isolating a composition comprising at least 95 mol %, at least 96 mol %, at least 97 mol %, at least 98 mol %, or at least 99 mol % $C_{10}$ monoolefins, the $C_{10}$ monoolefins comprising (i) at least 3 mol %, at least 4 mol %, at least 5 mol %, at least 6 mol %, or at least 7 mol % 2-butyl-1-hexene, (ii) at least 10 mol %, at least 11 mol %, at least 12 mol %, at least 13 mol %, or at least 14 mol % 3-propyl-1-heptene, (iii) at least 7 mol %, at least 8 mol %, at least 9 mol %, at least 10 mol %, or at least 11 mol % 4-ethyl-1-octene, and (iv) at least 24 mol %, at least 26 mol %, at least 28 mol %, at least 30 mol %, or at least 32 mol % 5-methyl-1-nonene. In yet another embodiment, the process can comprise a)

contacting 1) ethylene, 2) the catalyst system comprising i) a chromium containing compound, ii) a heteroatomic ligand, and iii) an alkylaluminum compound, and 3) optionally a reaction system diluent; b) forming an oligomer product comprising 1-hexene and/or 1-octene in a reaction system; c) discharging a reaction system effluent from the reaction system; d) contacting the reaction system effluent with a catalyst system deactivating agent; e) isolating a first composition comprising (a) at least 76 mol %, at least 78 mol %, at least 80 mol %, or at least 82 mol % $C_{10}$ monoolefins, the $C_{10}$ monoolefins comprising (i) at least 3 mol %, at least 4 mol %, at least 5 mol %, at least 6 mol %, at least 7 mol %, or at least 8 mol % 2-butyl-1-hexene, (ii) at least 8 mol %, at least 9 mol %, at least 10 mol %, at least 11 mol %, at least 12 mol %, or at least 13 mol % 3-propyl-1-heptene, (iii) at least 6 mol %, at least 7 mol %, at least 8 mol %, at least 9 mol %, at least 10 mol %, or at least 11 mol % 4-ethyl-1-octene, and (iv) at least 20 mol %, at least 22 mol %, at least 24 mol %, at least 26 mol %, at least 28 mol %, or at least 30 mol % 5-methyl-1-nonene, and (b) at least 1 mol %, at least 2 mol %, at least 3 mol %, or at least 4 mol % $C_{14}$ monoolefins; and f) recovering a second composition comprising at least 95 mol %, at least 96 mol %, at least 97 mol %, at least 98 mol %, or at least 99 mol % $C_{10}$ monoolefins, the $C_{10}$ monoolefins comprising (i) at least 3 mol %, at least 4 mol %, at least 5 mol %, at least 6 mol %, or at least 7 mol % 2-butyl-1-hexene, (ii) at least 10 mol %, at least 11 mol %, at least 12 mol %, at least 13 mol %, or at least 14 mol % 3-propyl-1-heptene, (iii) at least 7 mol %, at least 8 mol %, at least 9 mol %, at least 10 mol %, or at least 11 mol % 4-ethyl-1-octene, and (iv) at least 24 mol %, at least 26 mol %, at least 28 mol %, at least 30 mol %, or at least 32 mol % 5-methyl-1-nonene from the first composition. In some embodiments, these processes can further comprise forming a catalyst system mixture comprising, or consisting essentially of, i) a chromium containing compound, ii) a heteroatomic ligand, iii) an alkylaluminum compound, and iv) a catalyst system solvent; or alternatively, forming a catalyst system mixture comprising, or consisting essentially of, i) a heteroatomic ligand complexed to a chromium containing compound, ii) an alkylaluminum compound, and iii) a catalyst system solvent. When the process further comprises forming a catalyst system mixture, the catalyst system mixture is contacted with ethylene, and the optional reaction system diluent. In some embodiments, the step of contacting the catalyst system (or catalyst system mixture) with ethylene and the optional reaction system diluent can be a step of contacting the catalyst system (or catalyst system mixture) with ethylene, an optional reaction system diluent, and hydrogen. The catalyst system, chromium containing compound, a heteroatomic ligand, alkylaluminum compound, ethylene, solvents, are independently described herein and can be utilized, without limitation to further describe the processes for forming the first composition and/or second composition.

In an embodiment, the reaction system can operate at any pressure that can facilitate the formation of the oligomer product (or trimerization product, or ethylene tetramerization product, or trimerization and tetramerization product). In an embodiment, the pressure at which the reaction system can operate can be any pressure that produces a desired oligomer product (or trimerization product, or tetramerization product, or trimerization and tetramerization product). In some embodiments, the oligomer product (or trimerization product, or tetramerization product, or trimerization and tetramerization product) can be formed at a pressure greater than or equal to 0 psig (0 KPa); alternatively, greater than or equal to 50 psig (344 KPa); alternatively, greater than or equal to 100 psig (689 KPa); or alternatively, greater than or equal to 150 psig (1.0 MPa). In other embodiments, the oligomer product (or trimerization product, or tetramerization product, or trimerization and tetramerization product) can be formed at a pressure ranging from 0 psig (0 KPa) to 2,500 psig (17.3 MPa); alternatively, from 0 psig (KPa) to 1,600 psig (11.0 MPa); alternatively, from 0 psig (KPa) to 1,500 psig (10.4 MPa); alternatively, from 50 psig (344 KPa) to 2,500 psig (17.3 MPa); alternatively, from 100 psig (689 KPa) to 2,500 psig (17.3 MPa); alternatively, from 150 psig (1.0 MPa) to 2,000 psig (13.8 MPa); or alternatively, from 300 psig (2.0 MPa) to 900 psig (6.2 MPa). In some embodiments, the ethylene pressure (or ethylene partial pressure) at which the oligomer product (or trimerization product, or tetramerization product, or trimerization and tetramerization product) can be formed can be greater than or equal to 0 psig (0 KPa); alternatively, greater than or equal to 50 psig (344 KPa); alternatively, greater than or equal to 100 psig (689 KPa); or alternatively, greater than or equal to 150 psig (1.0 MPa). In other embodiments, the ethylene pressure (or ethylene partial pressure) at which the oligomer product (or trimerization product, or tetramerization product, or trimerization and tetramerization product) can be formed can range from 0 psig (0 KPa) to 2,500 psig (17.3 MPa); alternatively, from 50 psig (344 KPa) to 2,500 psig (17.3 MPa); alternatively, from 100 psig (689 KPa) to 2,500 psig (17.3 MPa); or alternatively, from 150 psig (1.0 MPa) to 2,000 psig (13.8).

In an embodiment, a temperature (e.g., a minimum temperature) at which the oligomer product (or trimerization product, or tetramerization product, or trimerization and tetramerization product) can be formed can be at least 0° C.; alternatively, at least 10° C.; alternatively, at least 20° C.; alternatively, at least 30° C.; alternatively, at least 40° C.; alternatively, at least 50° C.; alternatively, at least 60° C.; alternatively, at least 70° C.; alternatively, at least 80° C.; alternatively, at least 90° C.; alternatively, at least 100° C.; alternatively, at least 110° C.; alternatively, at least 120° C.; alternatively, at least 130° C.; alternatively, at least 140° C.; alternatively, at least 150° C.; alternatively, at least 160° C.; alternatively, at least 170° C.; or alternatively, at least 180° C. In some embodiments, a temperature (e.g., maximum temperature) at which the oligomer product (or trimerization product, or tetramerization product, or trimerization and tetramerization product) can be formed can be less than 180° C.; alternatively, less than 160° C.; alternatively, less than 140° C.; alternatively, less than 120° C.; alternatively, less than 100° C.; alternatively, less than 90° C.; or alternatively, less than 80° C. In some embodiments, the temperature at which the oligomer product (or trimerization product, or tetramerization product, or trimerization and tetramerization product) can be formed can range from any minimum temperature described herein to any maximum reaction temperature described herein as long as the maximum temperature is greater than the minimum temperature. In an embodiment, the temperature at which the oligomer product (or trimerization product, or ethylene tetramerization product, or trimerization and tetramerization product) can be formed can range from 0° C. to 180° C.; alternatively, from 10° C. to 160° C.; alternatively, from 20° C. to 140° C.; alternatively, from 30° C. to 120° C.; alternatively, from 40° C. to 100° C.; alternatively, from 50° C. to 100° C.; or alternatively, from 60° C. to 140° C. Other temperature ranges at which the oligomer product (or trimerization product, or tetramerization product, or trimerization and tetramerization product) can be formed can be understood by those skilled in the art with the help of this disclosure.

In an embodiment, a reaction time can comprise any time that can produce a desired quantity of oligomer product (or trimerization product, or tetramerization product, or trimerization and tetramerization product); alternatively, any time that can provide a desired catalyst system productivity; or alternatively, any time that can provide a desired conversion of ethylene. For example, an ethylene conversion can be at least 30 wt. % percent; alternatively, at least 35 wt. % percent; alternatively, at least 40 wt. % percent; or alternatively, at least 45 wt. % percent.

In an embodiment, the oligomer product (or trimerization product) can comprise at least 70 wt. % hexene; alternatively, at least 75 wt. % hexene; alternatively, at least 80 wt. % hexene; alternatively, at least 85 wt. % hexene; or alternatively, at least 90 wt. % hexene, based upon the weight of the oligomer product (or trimerization product). In some embodiments, the oligomer product (or trimerization product) can comprise from 70 wt. % to 99.8 wt. % hexene; alternatively, from 75 wt. % to 99.7 wt. % hexene; or alternatively, from 80 wt. % to 99.6 wt. % hexane, based upon the weight of the oligomer product (or trimerization product). In an embodiment, the oligomer product (or tetramerization product) can comprise at least 70 wt. % octene; alternatively, at least 75 wt. % octene; alternatively, at least 80 wt. % octene; alternatively, at least 85 wt. % octene; or alternatively, at least 90 wt. % octene, based upon the weight of the oligomer product (or tetramerization product). In some embodiments, the oligomer product (or tetramerization product) can comprise from 70 wt. % to 99.8 wt. % octene; alternatively, from 75 wt. % to 99.7 wt. % octene; or alternatively, from 80 wt. % to 99.6 wt. % octene, based upon the weight of the oligomer product (or tetramerization product). In an embodiment, the oligomer product (or trimerization and tetramerization product) can comprise at least 70 wt. % hexene and octene; alternatively, at least 75 wt. % hexene and octene; alternatively, at least 80 wt. % hexene and octene; alternatively, at least 85 wt. % hexene and octene; or alternatively, at least 90 wt. % hexene and octene, based upon the weight of the oligomer product (or trimerization and tetramerization product). In some embodiments, the oligomer product (or trimerization and tetramerization product) can comprise from 70 wt. % to 99.8 wt. % hexene and octene; alternatively, from 75 wt. % to 99.7 wt. % hexene and octene; or alternatively, from 80 wt. % to 99.6 wt. % hexene and octene, based upon the weight of the oligomer product (or trimerization and tetramerization product).

In an embodiment, the oligomer product (or trimerization product, tetramerization product, or trimerization and tetramerization product) can further comprise the $C_{10}$ monoolefins (as described herein) which can be present in the compositions comprising at least 76 mol %, at least 78 mol %, at least 80 mol %, or at least 82 mol % $C_{10}$ monoolefins; or alternatively, the compositions comprising at least 95 mol %, at least 96 mol %, at least 97 mol %, at least 98 mol %, or at least 99 mol % $C_{10}$ monoolefins. Additionally, the oligomer product (or trimerization product, tetramerization product, or trimerization and tetramerization product) can further comprise the $C_{9-}$ monoolefins (as described herein) and/or the $C_{11+}$ monoolefins (as described herein) which can be present in the compositions comprising at least 76 mol %, at least 78 mol %, at least 80 mol %, or at least 82 mol % $C_{10}$ monoolefins; or alternatively, the compositions comprising at least 95 mol %, at least 96 mol %, at least 97 mol %, at least 98 mol %, or at least 99 mol % $C_{10}$ monoolefins.

In ethylene trimerization, or ethylene trimerization and tetramerization embodiments, the trimer can comprise at least 85 wt. % 1-hexene; alternatively, at least 87.5 wt. % 1-hexene; alternatively, at least 90 wt. % 1-hexene; alternatively, at least 92.5 wt. % 1-hexene; alternatively, at least 95 wt. % 1-hexene; alternatively, at least 97 wt. % 1-hexene; or alternatively, at least 98 wt. % 1-hexene, based upon the weight of the trimer. In some ethylene trimerization, or ethylene trimerization and tetramerization embodiments, the trimer can comprise from 85 wt. % to 99.9 wt. % 1-hexene; alternatively, from 87.5 wt. % to 99.9 wt. % 1-hexene; alternatively, from 90 wt. % to 99.9 wt. % 1-hexene; alternatively, from 92.5 wt. % to 99.9 wt. % 1-hexene; alternatively, from 95 wt. % to 99.9 wt. % 1-hexene; alternatively, from 97 wt. % to 99.9 wt. % 1-hexene; or alternatively, from 98 wt. % to 99.9 wt. % 1-hexene, based upon the weight of the trimer.

In ethylene tetramerization, or ethylene trimerization and tetramerization embodiments, the tetramer can comprise at least 85 wt. % 1-octene; alternatively, at least 87.5 wt. % 1-octene; alternatively, at least 90 wt. % 1-octene; alternatively, at least 92.5 wt. % 1-octene; alternatively, at least 95 wt. % 1-octene; alternatively, at least 97 wt. % 1-octene; or alternatively at least 98 wt. % 1-octene, based upon the weight of the tetramer. In some ethylene tetramerization, or ethylene trimerization and tetramerization embodiments, the tetramer can comprise from 85 wt. % to 99.9 wt. % 1-octene; alternatively, from 87.5 wt. % to 99.9 wt. % 1-octene; alternatively, from 90 wt. % to 99.9 wt. % 1-octene; alternatively, from 92.5 wt. % to 99.9 wt. % 1-octene; alternatively, from 95 wt. % to 99.9 wt. % 1-octene; alternatively, from 97 wt. % to 99.9 wt. % 1-octene; or alternatively, from 98 wt. % to 99.9 wt. % 1-octene, based upon the weight of the tetramer.

For purposes of the disclosure herein, the term "reaction system effluent," and its derivatives (e.g., trimerization reaction system effluent, tetramerization reaction system effluent, or trimerization and tetramerization reaction system effluent) generally refers to all the material which exits the reaction system through a reaction system outlet/discharge, which discharges a reaction mixture and can include reaction mixture (e.g., ethylene, catalyst system or catalyst system components, and/or optional reaction system diluent or solvent), and/or reaction product(s) (e.g., oligomerization product including oligomers and non-oligomers). The term "reaction system effluent" and its derivatives can be qualified to refer to certain portions by use of additional qualifying terms. For example, while reaction system effluent refers to all material which exits the reaction system through the reaction system outlet/discharge, the term "reaction system oligomerization product effluent" refers to only the oligomerization product within the reaction system effluent.

In an embodiment, the reaction system effluent can comprise an oligomer product comprising at least 60 mol %; at least 65 mol %; at least 70 mol %; at least 75 mol %; or at least 80 mol % 1-hexene and/or 1-octene, the catalyst system, and the optional reaction system diluent. In some ethylene trimerization, or ethylene trimerization and tetramerization embodiments, the reaction system effluent can comprise i) an oligomer product comprising at least 60 mol %, at least 65 mol %, at least 70 mol %, at least 75 mol %, or at least 80 mol % 1-hexene, ii) the catalyst system, and iii) the optional reaction system diluent. In some ethylene tetramerization, or ethylene trimerization and tetramerization embodiments, the reaction system effluent can comprise i) an oligomer product comprising at least 60 mol %, at least 65 mol %, at least 70 mol %; at least 75 mol %, or at least 80 mol % 1-octene, ii) the catalyst system, and iii) the optional reaction system diluent. In some ethylene trimerization and tetramerization embodiments, the reaction system effluent can comprise i) an oligomer product comprising at least 60 mol %, at least 65 mol %, at least 70 mol %, at least 75 mol %, or at least 80 mol % 1-hexene and 1-octene, ii) the catalyst system, and iii) the optional reaction system diluent.

In an embodiment, the reaction system effluent can further comprise the $C_{10}$ monoolefins (as described herein) which can be present in the compositions comprising at least 76 mol %, at least 78 mol %, at least 80 mol %, or at least 82 mol % $C_{10}$ monoolefins; or alternatively, the compositions comprising at least 95 mol %, at least 96 mol %, at least 97 mol %, at least 98 mol %, or at least 99 mol % $C_{10}$ monoolefins. Additionally, the reaction system effluent can further comprise the $C_{9-}$ monoolefins (as described herein) and/or the monoolefins (as described herein) which can be present in the compositions comprising at least 76 mol %, at least 78 mol %, at least 80 mol %, or at least 82 mol % $C_{10}$ monoolefins; or alternatively, the compositions comprising at least 95 mol %, at least 96 mol %, at least 97 mol %, at least 98 mol %, or at least 99 mol % $C_{10}$ monoolefins.

In some embodiments, the reaction system effluent can be treated and subjected to one or more separation processes to recover components from the reaction system effluent (e.g., unreacted ethylene, solvent, oligomer product(s), and/or by-product(s), among others).

Prior to recovery of the trimer, tetramer, or trimer and tetramer, the reaction system effluent can be contacted with a catalyst system deactivating and quench agent (alternatively, referred to herein as a "catalyst system kill agent") to deactivate and quench the active catalyst system (e.g., to form a deactivated and quenched reaction system effluent). In an embodiment, the reaction system effluent can be contacted with a catalyst system deactivating agent to at least partially deactivate the catalyst system and produce a deactivated catalyst system (e.g., to form a deactivated reaction system effluent, or alternatively a reaction system effluent containing a deactivated catalyst system); and then at least a portion of the reaction system effluent containing the deactivated catalyst system or deactivated catalyst system components can be contacted with a catalyst system quench agent to quench the catalyst system. The catalyst system deactivating and quench agent, catalyst system deactivating agent, and/or catalyst system quench agent can be independently selected from mono-alcohols, diols, polyols, or combinations thereof. In an embodiment, the catalyst system deactivating and quench agent, catalyst system deactivating agent, and/or catalyst system quench agent can comprise any mono-alcohol, diol, or polyol which is soluble in the reaction system effluent. The mono-alcohol, diol, or polyol can be selected by boiling point, molecular weight, and/or such that the mono-alcohol, diol, or polyol does not form an azeotrope with the oligomer(s), trimer, and/or tetramer (and/or reaction system solvent). In some embodiments, the mono-alcohol, diol, or polyol can have a boiling point different from the oligomer(s), trimer, and/or tetramer (and/or reaction system solvent) in the reaction system effluent. In an embodiment, the mono-alcohol can be a $C_4$ to $C_{30}$ mono-alcohol, alternatively, a $C_4$ to $C_{20}$ mono-alcohol, or alternatively, a $C_4$ to $C_{12}$ mono-alcohol. In some embodiments, the mono-alcohol can be selected to be easily removable from the oligomer(s), trimer, or tetramer (e.g., 1-hexene in an ethylene trimerization process). Non-limiting examples of mono-alcohols suitable for use in the present disclosure include 1-hexanol, 2-hexanol, 3-hexanol, 2-ethyl-1-hexanol, 1-heptanol, 2-heptanol, 3-heptanol, 4-heptanol, 2-methyl-3-heptanol, 1-octanol, 2-octanol, 3-octanol, 4-octanol, 7-methyl-2-decanol, 1-decanol, 2-decanol, 3-decanol, 4-decanol, 5-decanol, 2-ethyl-1-decanol, or combinations thereof. In one or more specific embodiments, the mono-alcohol can comprise 2-ethyl-1-hexanol.

In an embodiment, the catalyst system deactivating and quench agent can be contacted with the reaction system effluent in an amount sufficient to deactivate the catalyst system (i.e., an amount that can inhibit, or halt: (1) production of undesirable solids, i.e., polymer; and/or (2) oligomer(s), trimer, and/or tetramer product purity degradation due to isomerization) in subsequent product separation processes and quench the catalyst system (i.e., an amount that can inhibit a pyrophoric nature of residual catalyst components). In these catalyst system deactivation and quench agent embodiments, the catalyst system deactivating and quench agent can be contacted with the reaction system effluent at an alcohol to metal of the metal alkyl compound (including metal alkyl compound which can be designated as a halogen containing compound) molar ratio (also referred to as an alcohol to metal molar ratio) of up to 100:1; alternatively, up to 50:1; alternatively, up to 25:1; alternatively, up to 10:1; alternatively, up to 5:1; alternatively, from 0.01:1 to 100:1; alternatively, from 0.1:1 to 50:1; alternatively, from 0.5:1 to 25:1; alternatively, from 0.75:1 to 5:1; alternatively, from 1:1 to 4:1; or alternatively, from 2:1 to 3:1. Catalyst system deactivation and quench processes are described in more detail in U.S. Pat. Nos. 5,689,028 and 8,344,198, among other documents.

In an embodiment, the reaction system effluent can be contacted with a catalyst system deactivation agent to at least partially deactivate the catalyst system; and later, a portion of the reaction system effluent containing at least a portion of the deactivated catalyst system (e.g., a portion of the reaction system effluent remaining after separating the oligomer, trimer, tetramer, and/or reaction system solvent from a reaction system effluent stream containing at least a portion of the at least partially deactivated catalyst system) can be contacted with the catalyst system quench agent to quench the catalyst system. In these catalyst system deactivating embodiments, the catalyst system deactivating agent can be contacted with the reaction system effluent at a catalyst deactivating agent to metal of the metal alkyl compound (including metal alkyl compound which can be designated as a halogen containing compound) molar ratio of from 0.75:1 to 1.25:1; alternatively, from 0.8:1 to 1.2:1; alternatively, from 0.85:1 to 1.15:1; or alternatively, about 1:1. In these embodiments, the catalyst system quench agent can be contacted with at least a portion of a stream containing at least a portion of the at least partially deactivated catalyst system at a catalyst system quench agent to metal of the metal alkyl compound (including metal alkyl compound which can be designated as a halogen containing compound) molar ratio of from 0.5:1 to 1.5:1; alternatively, from 0.7:1 to 1.2:1; alternatively, from 0.8:1 to 1.1:1; or alternatively, about 1:1. Additional information regarding a split catalyst system deactivation and catalyst system quench can be found in U.S. Pat. No. 8,049,052.

In an embodiment, the reaction system effluent can comprise components present in the reaction mixture, as previously discussed herein. For example, in an ethylene trimerization, ethylene tetramerization, or ethylene trimerization and tetramerization, the reaction system effluent can generally include ethylene, the oligomer product (or alternatively, trimerization product, tetramerization product, or trimerization and tetramerization product), the catalyst system (including a chromium containing compound which may or may not be in the same form as the chromium containing compound contacted to form the catalyst system), and/or the reaction system solvent, among other components (e.g., the $C_{10}$ monoolefins of the first composition or second composition as described herein). A deactivated reaction system effluent or deactivated and quenched reaction system effluent generally represents the reaction system effluent which has been contacted with the catalyst system deactivating agent or the catalyst system deactivating and quench agent, respectively; and generally comprises ethylene, the oligomer product (or alternatively, trimerization product, tetramerization product, or trimerization and tetramerization product), the deactivated catalyst system or the deactivated and quenched catalyst system (including a chromium containing compound, and other deactivated quenched catalyst system components or deactivated and quenched catalyst system components), and/or the reaction system solvent, among other components. In regards to the reaction system effluent, deactivated reaction system effluent, or deactivated and quenched reaction system effluent, the chromium containing compound, may be the same as (or alternatively, may not be in the same form as) the chromium containing compound present in the catalyst system prior to the oligomerization reaction As such, the term "chromium containing compound" and their derivatives, when used in regards to the reaction system effluent, deactivated reaction system effluent, or deactivated and quenched reaction system effluent, refers to all chromium containing compounds, regardless of form, that are present in the reaction system effluent, deactivated reaction system effluent, deactivated and quenched reaction system effluent, or reaction system effluent stream (deactivated, or deactivated and quenched) which has been processed to remove one or more materials comprising all or a portion of ethylene, the oligomerization product (or alternatively, ethylene trimerization product, ethylene tetramerization product, or ethylene trimerization and tetramerization product), and/or the reaction system solvent. The term "chromium containing compounds" and their derivatives, when used in regards to the reaction system effluent, deactivated reaction system effluent, or deactivated and quenched reaction system effluent, refers to the chromium containing compounds which are used to form the catalyst system or refer to the chromium containing compound complexed to a heteroatomic ligand of the catalyst system. After the catalyst system has been deactivated, or deactivated and quenched, the oligomer(s), trimer, tetramer, trimer and tetramer, and/or reaction system solvent can be separated (e.g., isolated) from a deactivated reaction system effluent or deactivated and quenched reaction system effluent. Any separation process or combination of processes can be used, including, for example, distillation. In one or more embodiments, the separation process can comprise at least one separation vessel comprising columns, tanks, flash vessels, distillation columns, or combinations thereof.

In an embodiment, the oligomer(s) (alternatively, trimer; alternatively, tetramer; or alternatively, trimer and tetramer) can be isolated from a deactivated reaction system effluent or deactivated and quenched reaction system effluent to yield a stream (e.g., isolated stream) comprising (a) at least 90 mol % 1-hexene; alternatively, at least 92.5 wt. % 1-hexene; alternatively, at least 95 wt. % 1-hexene; alternatively, at least 97 wt. % 1-hexene; or alternatively, at least 98 wt. % 1-hexene, based upon the weight of the stream; (b) at least 90 mol % 1-octene; alternatively, at least 92.5 wt. % 1-octene; alternatively, at least 95 wt. % 1-octene; alternatively, at least 97 wt. % 1-octene; or alternatively, at least 98 wt. % 1-octene, based upon the weight of the stream; or (c) at least 90 mol % 1-hexene and 1-octene; alternatively, at least 92.5 wt. % 1-hexene and 1-octene; alternatively, at least 95 wt. % 1-hexene and 1-octene; alternatively, at least 97 wt. % 1-hexene and 1-octene; or alternatively, at least 98 wt. % 1-hexene and 1-octene, based upon the weight of the stream. In some ethylene trimerization, or ethylene trimerization and tetramerization embodiments, the isolated stream can comprise from 90 wt. % to 99.9 wt. % 1-hexene; alternatively, from 92.5 wt. % to 99.9 wt. % 1-hexene; alternatively, from 95 wt. % to 99.9 wt. % 1-hexene; alternatively, from 97 wt. % to 99.9 wt. % 1-hexene; or alternatively, from 98 wt. % to 99.9 wt. % 1-hexene, based upon the weight of the isolated stream. In some ethylene tetramerization, or ethylene trimerization and tetramerization embodiments, the isolated stream can comprise from 90 wt. % to 99.9 wt. % 1-octene; alternatively, from 92.5 wt. % to 99.9 wt. % 1-octene; alternatively, from 95 wt. % to 99.9 wt. % 1-octene; alternatively, from 97 wt. % to 99.9 wt. % 1-octene; or alternatively, from 98 wt. % to 99.9 wt. % 1-octene, based upon the weight of the isolated stream. In some ethylene trimerization and tetramerization embodiments, the isolated stream can comprise from 90 wt. % to 99.9 wt. % 1-hexene and 1-octene; alternatively, from 92.5 wt. % to 99.9 wt. % 1-hexene and 1-octene; alternatively, from 95 wt. % to 99.9 wt. % 1-hexene and 1-octene; alternatively, from 97 wt. % to 99.9 wt. % 1-hexene and 1-octene; or alternatively, from 98 wt. % to 99.9 wt. % 1-hexene and 1-octene, based upon the weight of the isolated stream.

In an embodiment, the process(es) for isolating the oligomer(s) (alternatively, trimer; alternatively, tetramer; or alternatively, trimer and tetramer) from a deactivated reaction system effluent or deactivated and quenched reaction system effluent can also isolate a composition (e.g., a first composition) comprising (a) at least 76 mol %, at least 78 mol %, at least 80 mol %, or at least 82 mol % $C_{10}$ monoolefins, the $C_{10}$ monoolefins comprising (i) at least 3 mol %, at least 4 mol %, at least 5 mol %, at least 6 mol %, at least 7 mol %, or at least 8 mol % 2-butyl-1-hexene, (ii) at least 8 mol %, at least 9 mol %, at least 10 mol %, at least 11 mol %, at least 12 mol %, or at least 13 mol % 3-propyl-1-heptene, (iii) at least 6 mol %, at least 7 mol %, at least 8 mol %, at least 9 mol %, at least 10 mol %, or at least 11 mol % 4-ethyl-1-octene, and (iv) at least 20 mol %, at least 22 mol %, at least 24 mol %, at least 26 mol %, at least 28 mol %, or at least 30 mol % 5-methyl-1-nonene, and (b) at least 1 mol %, at least 2 mol %, at least 3 mol %, or at least 4 mol % $C_{14}$ monoolefins. In an embodiment, a composition (e.g., a second composition) can be isolated from a deactivated reaction system effluent or deactivated and quenched reaction system effluent, or can be recovered (e.g., isolated, separated, etc.) from the first composition, the second composition comprising at least 95 mol %, at least 96 mol %, at least 97 mol %, at least 98 mol %, or at least 99 mol % $C_{10}$ monoolefins, the $C_{10}$ monoolefins comprising (i) at least 3 mol %, at least 4 mol %, at least 5 mol %, at least 6 mol %, or at least 7 mol % 2-butyl-1-hexene, (ii) at least 10 mol %, at least 11 mol %, at least 12 mol %, at least 13 mol %, or at least 14 mol % 3-propyl-1-heptene, (iii) at least 7 mol %, at least 8 mol %, at least 9 mol %, at least 10 mol %, or at least 11 mol % 4-ethyl-1-octene, and (iv) at least 24 mol %, at least 26 mol %, at least 28 mol %, at least 30 mol %, or at least 32 mol % 5-methyl-1-nonene. As will be appreciated by one of skill in the art, and with the help of this disclosure, the compositions disclosed herein comprise olefins, and could be used as intermediates for a variety of other processes.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Compositions comprising $C_{10}$ monoolefins as disclosed herein were isolated from an ethylene trimerization process (e.g., a commercial ethylene trimerization plant) utilizing a chromium pyrrole catalyst system. The compositions comprising $C_{10}$ monoolefins were analyzed by gas chromatograph-mass spectrometry (GC-MS) using a 15 m×0.25 mm×0.5 μm DB-5 column and/or a 40 m×0.1 mm×0.1 μm DB-1 column to determine component identities, and standard gas chromatography (GC) using a 60 m×0.32 mm×1 μm DB-1 column to determine the quantity of the components present in the compositions. The data and analysis of the compositions from the commercial ethylene trimerization plant are provided in Table 3, Table 4, and Table 5. The data in Table 3 provides the component identities for the hydrocarbon components present in an amount of at least 0.03 wt. %, and identified heteroatomic compounds present in at least 0.1 wt. %, which were then converted to mol %. Table 4 provides a compositional make-up of the composition in terms of aliphatic hydrocarbon carbon number, aromatic hydrocarbon, and alcohol of the compositions isolated from the commercial ethylene trimerization plant. Table 5 provides the distribution of decene in the composition isolated from the commercial ethylene trimerization plant.

TABLE 3

Component Analysis of Compositions Isolated From a Commercial Ethylene Trimerization Plant.

| Component | GC-MS Retention Time (Minutes) | Sample 1 (Mol %) | Sample 2 (Mol %) | Sample 3 (Mol %) |
| --- | --- | --- | --- | --- |
| Cyclohexane | 11.684 | 3.58% | 3.73% | 3.45% |
| Octene | 16.327 | 0.04% | 0.04% | 0.04% |
| 1-Octene | 17.313 | 1.42% | 1.42% | 1.33% |
| Octane | 17.743 | 0.18% | 0.18% | 0.17% |
| Ethylbenzene | 19.547 | 2.31% | 2.27% | 2.12% |
| 3-Propyl-1-heptene | 21.932 | 14.59% | 14.52% | 14.74% |
| Decene | 22.031 | 0.16% | 0.16% | 0.16% |
| 4-Ethyl-1-octene | 22.347 | 13.14% | 13.07% | 13.28% |
| 5-Methyl-1-nonene | 22.646 | 32.15% | 31.94% | 32.19% |
| Decene | 22.646 | 0.65% | 0.65% | 0.65% |
| 2-Butyl-1-hexene | 22.933 | 9.96% | 9.90% | 9.94% |
| Decenes | 23.006 | 0.16% | 0.16% | 0.16% |
| Decenes | 23.183 | 0.16% | 0.16% | 0.16% |
| 1-Decene | 23.366 | 4.09% | 4.07% | 4.04% |
| 4/5-Decene | 23.448 | 9.12% | 9.09% | 9.06% |
| Decane | 23.625 | 0.36% | 0.36% | 0.31% |
| $C_8$ alcohol | 23.945 | 1.49% | 1.55% | 1.51% |
| Dodecene | 26.38 | 0.04% | 0.05% | 0.04% |
| Dodecene | 26.495 | 0.05% | 0.06% | 0.05% |
| Dodecene | 26.65 | 0.02% | 0.02% | 0.02% |
| Dodecene | 26.806 | 0.04% | 0.04% | 0.04% |
| Dodecene | 26.881 | 0.15% | 0.16% | 0.16% |
| Dodecene | 27.267 | 0.07% | 0.07% | 0.07% |
| 1-Dodecene | 27.703 | 0.70% | 0.72% | 0.71% |
| Dodecane | 27.911 | 0.29% | 0.30% | 0.30% |

TABLE 3-continued

Component Analysis of Compositions Isolated From a Commercial Ethylene Trimerization Plant.

| Component | GC-MS Retention Time (Minutes) | Sample 1 (Mol %) | Sample 2 (Mol %) | Sample 3 (Mol %) |
| --- | --- | --- | --- | --- |
| Tetradecenes | 28.853-31.305 | 4.80% | 5.01% | 4.98% |
| Tetradecane | 31.474 | 0.14% | 0.15% | 0.15% |
| Octadecene | 34.454 | 0.11% | 0.11% | 0.11% |

TABLE 4

Aliphatic Hydrocarbon Carbon Number, Aromatic Hydrocarbon, and Alcohol Make-up of Compositions Isolated From a Commercial Ethylene Trimerization Plant.

| | Sample 1 (Mol %) | Sample 2 (Mol %) | Sample 3 (Mol %) |
| --- | --- | --- | --- |
| Cyclohexane | 3.58% | 3.73% | 3.45% |
| $C_8$ | 1.65% | 1.64% | 1.55% |
| $C_{10}$ | 84.53% | 84.08% | 84.69% |
| $C_{12}$ | 1.36% | 1.42% | 1.40% |
| $C_{14}$ | 4.94% | 5.16% | 5.13% |
| $C_{18}$ | 0.14% | 0.15% | 0.15% |
| Ethylbenzene | 2.31% | 2.27% | 2.12% |
| 2-Ethyl-1-hexanol | 1.49% | 1.55% | 1.51% |

TABLE 5

Distribution of Decenes within Compositions Isolated From a Commercial Ethylene Trimerization Plant.

| | Sample 1 (Mol %) | Sample 2 (Mol %) | Sample 3 (Mol %) |
| --- | --- | --- | --- |
| 1-Decene | 4.85% | 4.86% | 4.78% |
| 2-Butyl-1-hexene | 11.83% | 11.82% | 11.78% |
| 3-Propyl-1-heptene | 17.34% | 17.35% | 17.47% |
| 4-Ethyl-1-octene | 15.61% | 15.61% | 15.74% |
| 5-Methyl-1-nonene | 38.20% | 38.15% | 38.15% |
| 4/5-Decenes | 10.83% | 10.86% | 10.73% |
| Other Decenes | 1.34% | 1.35% | 1.34% |

ADDITIONAL DISCLOSURE

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

Group A

Embodiment 1

A composition comprising: a) at least 76 mol %, at least 78 mol %, at least 80 mol %, or at least 82 mol % $C_{10}$ monoolefins, the $C_{10}$ monoolefins comprising i) at least 3 mol %, at least 4 mol %, at least 5 mol %, at least 6 mol %, at least 7 mol %, or at least 8 mol % 2-butyl-1-hexene, ii) at least 8 mol %, at least 9 mol %, at least 10 mol %, at least 11 mol %, at least 12 mol %, or at least 13 mol %

3-propyl-1-heptene, iii) at least 6 mol %, at least 7 mol %, at least 8 mol %, at least 9 mol %, at least 10 mol %, or at least 11 mol % 4-ethyl-1-octene, and iv) at least 20 mol %, at least 22 mol %, at least 24 mol %, at least 26 mol %, at least 28 mol %, or at least 30 mol % 5-methyl-1-nonene, and b) at least 1 mol %, at least 2 mol %, at least 3 mol %, or at least 4 mol % $C_{14}$ monoolefins.

Embodiment 2

The composition of embodiment 1 or 2, wherein the composition comprises from 76 mol % to 92 mol %, from 78 mol % to 90 mol %, from 80 mol % to 88 mol %, or from 82 mol % to 86 mol % $C_{10}$ monoolefins.

Embodiment 3

The composition of embodiment 1 or 2, wherein the composition comprises from 1 mol % to 12 mol %, from 2 mol % to 10 mol %, from 3 mol % to 8 mol %, or from 4 mol % to 7 mol % $C_{14}$ monoolefins.

Embodiment 4

The composition of any one of embodiments 1 to 3, further comprising from 0.1 mol % to 5 mol %, from 0.25 mol % to 4 mol %, or from 0.5 mol % to 3 mol % $C_{12}$ monoolefins, the $C_{12}$ monoolefins comprising from 54 mol % to 74 mol %, from 56 mol % to 72 mol %, from 58 mol % to 70 mol %, or from 60 mol % to 68 mol % 1-dodecene.

Embodiment 5

The composition of embodiment 1 or 4, further comprising from 0.1 mol % to 5 mol %, from 0.25 mol % to 4 mol %, or from 0.5 mol % to 3 mol % $C_8$ monoolefins, the $C_8$ monoolefins comprising at least 95 mol %, at least 96 mol %, at least 97 mol %, at least 98 mol %, or at least 99 mol % 1-octene.

Embodiment 6

The composition of any one of embodiments 1 to 5, further comprising from 0.05 mol % to 2 mol %, from 0.04 mol % to 1.5 mol %, from 0.06 mol % to 1.25 mol %, from 0.08 mol % to 1 mol %, or from 0.1 mol % to 0.75 mol % $C_{16}$ monoolefins and/or $C_{18}$ monoolefins.

Embodiment 7

The composition of any one of embodiments 1 to 6, further comprising from 0.2 mol % to 6 mol %, from 0.3 mol % to 4 mol %, from 0.4 mol % to 2 mol %, or from 0.5 mol % to 1.5 mol % acyclic saturated hydrocarbons.

Embodiment 8

The composition of embodiment 7, wherein the acyclic saturated hydrocarbons comprise octane, decane, dodecane, tetradecane, or combinations thereof.

Embodiment 9

The composition of embodiment 7 or 8, wherein the acyclic saturated hydrocarbons comprise a) from 10 mol % to 26 mol %, from 12 mol % to 24 mol %, or from 14 mol % to 22 mol % octane, b) from 24 mol % to 48 mol %, from 27 mol % to 45 mol %, or from 30 mol % to 42 mol % decane, c) from 22 mol % to 40 mol %, from 24 mol % to 38 mol %, or from 26 mol % to 36 mol % dodecane, and d) from 7 mol % to 23 mol %, from 9 mol % to 21 mol %, or from 11 mol % to 19 mol % tetradecane.

Embodiment 10

The composition of any one of embodiments 1 to 9, further comprising from 1.9 mol % to 5.1 mol %, from 2.1 mol % to 4.9 mol %, from 2.3 mol % to 4.7 mol %, or from 2.5 mol % to 4.5 mol % cyclic saturated hydrocarbons.

Embodiment 11

The composition of embodiment 10, wherein the cyclic saturated hydrocarbon is methylcyclopentane, cyclohexane, methylcyclohexane, or combinations thereof.

Embodiment 12

The composition of any one of embodiments 1 to 11, further comprising from 1 mol % to 3.4 mol %, from 1.2 mol % to 3.2 mol %, from 1.4 mol % to 3.0 mol %, or from 1.6 mol % to 2.8 mol % of a $C_6$ to $C_{12}$ aromatic hydrocarbon.

Embodiment 13

The composition of embodiment 12, wherein the $C_6$ to $C_{12}$ aromatic hydrocarbon is benzene, toluene, ethylbenzene, xylene, mesitylene, hexamethylbenzene, or combinations thereof.

Embodiment 14

The composition of any one of embodiments 1 to 13, further comprising from 0.4 mol % to 3 mol %, from 0.6 mol % to 3 mol %, from 0.8 mol % to 2.5 mol %, or from 1 mol % to 2 mol % of a $C_4$ to $C_{12}$ alcohol.

Embodiment 15

The composition of embodiment 14, wherein the $C_4$ to $C_{12}$ alcohol is 1-hexanol, 2-hexanol, 3-hexanol, 2-ethyl-1-hexanol, 1-heptanol, 2-heptanol, 3-heptanol, 4-heptanol, 2-methyl-3-heptanol, 1-octanol, 2-octanol, 3-octanol, 4-octanol, 7-methyl-2-decanol, 1-decanol, 2-decanol, 3-decanol, 4-decanol, 5-decanol, 2-ethyl-1-decanol, or combinations thereof.

Embodiment 16

A composition comprising at least 95 mol %, at least 96 mol %, at least 97 mol %, at least 98 mol %, or at least 99 mol % $C_{10}$ monoolefins, the $C_{10}$ monoolefins comprising i) at least 3 mol %, at least 4 mol %, at least 5 mol %, at least 6 mol %, or at least 7 mol % 2-butyl-1-hexene, ii) at least 10 mol %, at least 11 mol %, at least 12 mol %, at least 13 mol %, or at least 14 mol % 3-propyl-1-heptene, iii) at least 7 mol %, at least 8 mol %, at least 9 mol %, at least 10 mol %, or at least 11 mol % 4-ethyl-1-octene, and iv) at least 24 mol %, at least 26 mol %, at least 28 mol %, at least 30 mol %, or at least 32 mol % 5-methyl-1-nonene.

Embodiment 17

The composition of embodiment 16, wherein the composition comprises less than 3 mol %, less than 2.5 mol %, less than 2 mol %, less than 1.5 mol %, less than 1 mol %, or less than 0.5 mol % $C_{9-}$ hydrocarbons.

Embodiment 18

The composition of embodiment 15 or 16, wherein composition comprises less than 3 mol %, less than 2.5 mol %, less than 2 mol %, less than 1.5 mol %, less than 1 mol %, or less than 0.5 mol % $C_{11+}$ hydrocarbons.

Embodiment 19

The composition of any one of embodiments 1 to 15, or the composition of any one of embodiments 14 to 18, wherein the $C_{10}$ monoolefins comprise from 3 mol % to 20 mol %, from 4 mol % to 18 mol %, from 5 mol % to 17 mol %, from 6 mol % to 16 mol %, or from 7 mol % to 15 mol % 2-butyl-1-hexene.

Embodiment 20

The composition of any one of embodiments 1 to 15, or the composition of any one of embodiments 14 to 19, wherein the $C_{10}$ monoolefins comprise from 10 mol % to 32 mol %, from 11 mol % to 30 mol %, from 12 mol % to 28 mol %, from 13 mol % to 26 mol %, or from 14 mol % to 24 mol % 3-propyl-1-heptene.

Embodiment 21

The composition of any one of embodiments 1 to 15, or the composition of any one of embodiments 16 to 20, wherein the $C_{10}$ monoolefins comprise from 7 mol % to 25 mol %, from 8 mol % to 24 mol %, from 9 mol % to 23 mol %, from 10 mol % to 22 mol %, or from 11 mol % to 21 mol % 4-ethyl-1-octene.

Embodiment 22

The composition of any one of embodiments 1 to 15, or the composition of any one of embodiments 16 to 21, wherein the $C_{10}$ monoolefins comprise from 24 mol % to 52 mol %, from 26 mol % to 50 mol %, from 28 mol % to 48 mol %, from 30 mol % to 46 mol %, or from 32 mol % to 44 mol % 5-methyl-1-nonene.

Embodiment 23

The composition of any one of embodiments 1 to 15, or the composition of any one of embodiments 16 to 22, wherein a molar ratio of 5-methyl-1-nonene to 2-butyl-1-hexene is at least 2:1, at least 2.4:1, at least 2.6:1, or at least 2.8:1.

Embodiment 24

The composition of any one of embodiments 1 to 15 or the composition of any one of embodiments 16 to 23, wherein a molar ratio of 5-methyl-1-nonene to 3-propyl-1-heptene is at least 1.2:1, at least 1.4:1, at least 1.6:1, or at least 1.8:1.

Embodiment 25

The composition of any one of embodiments 1 to 15 or the composition of any one of embodiments 16 to 24, wherein a molar ratio of 5-methyl-1-nonene to 4-ethyl-1-octene is at least 1.6:1, at least 1.7:1, at least 1.9:1, or at least 2.1:1.

Embodiment 26

The composition of any one of embodiments 1 to 15 or the composition of any one of embodiments 16 to 25, wherein the $C_{10}$ monoolefins comprises from 1 mol % to 16 mol %, from 2 mol % to 15 mol %, from 3 mol % to 14 mol %, from 4 mol % to 13 mol %, or from 6 mol % to 12 mol % 4-decene and/or 5-decene.

Embodiment 27

The composition of any one of embodiments 1 to 15 or the composition of any one of embodiments 16 to 26, wherein the $C_{10}$ monoolefins comprises less than or equal to 10 mol %, less than or equal to 9 mol %, less than or equal to 8 mol %, less than or equal to 7 mol %, or less than or equal to 6 mol % 1-decene.

Embodiment 28

The composition of any one of embodiments 1 to 15 or the composition of any one of embodiments 16 to 27, wherein the $C_{10}$ monoolefins comprises from 0.5 mol % to 9 mol %, from 1 mol % to 8 mol %, from 1.5 mol % to 7 mol %, or from 2 mol % to 6 mol % 1-decene.

Embodiment 29

A process comprising: a) contacting 1) ethylene, 2) a catalyst system comprising i) a chromium containing compound, ii) a heteroatomic ligand, and iii) an alkylaluminum compound, and 3) optionally a reaction system diluent; b) forming an oligomer product comprising 1-hexene and/or 1-octene in a reaction system; c) discharging a reaction system effluent from the reaction system; d) contacting the reaction system effluent with a catalyst system deactivating agent; and e) isolating the composition of any one of embodiments 1 to 15, or the composition of any one of embodiments 16 to 28.

Embodiment 30

A process comprising: a) contacting 1) ethylene, 2) a catalyst system comprising i) a chromium containing compound, ii) a heteroatomic ligand, and iii) an alkylaluminum compound, and 3) optionally a reaction system diluent; b) forming an oligomer product comprising 1-hexene and/or 1-octene in a reaction system; c) discharging a reaction system effluent from the reaction system; d) contacting the reaction system effluent with a catalyst system deactivating agent; and e) isolating a first composition defined by any one of embodiments 1 to 15.

Embodiment 31

The process of embodiment 30, the process further comprising recovering a second composition defined by any one of embodiments 16 to 28 from the first composition defined by any one of embodiments 1 to 15.

Embodiment 32

The process of any one of embodiments 29 to 31, wherein the catalyst system is prepared in a catalyst system solvent.

Embodiment 33

The process of embodiment 32, wherein the reaction system effluent comprises the oligomer product comprising at least 60 mol % 1-hexene and/or 1-octene, the catalyst system, and the optional reaction system diluent.

Embodiment 34

The process of any one of embodiments 29 to 33, wherein the process further comprises isolating a stream comprising (a) at least 90 mol % 1-hexene, (b) at least 90 mol % 1-octene, or (c) at least 90 mol % 1-hexene and 1-octene.

Embodiment 35

The process of any one of embodiments 29 to 34, wherein the heteroatomic ligand is a pyrrole compound, a diphosphino aminyl compound, an $N^2$-phosphinyl amidine compound, an $N^2$-phosphinyl formamidine compound, an $N^2$-phosphinyl guanidine compound, or combinations thereof.

Embodiment 36

The process of any one of embodiments 29 to 35, wherein the catalyst system is selected from the group consisting of a) a chromium containing compound, a pyrrole compound, an alkylaluminum compound, and optionally a halide containing compound; b) a chromium containing compound, a diphosphino aminyl compound, an alkylaluminum compound; c) a chromium containing compound complexed to a diphosphino aminyl compound, and an alkylaluminum compound; d) a chromium containing compound, an $N^2$-phosphinyl amidine compound, and an alkylaluminum compound; e) a chromium containing compound complexed to an $N^2$-phosphinyl amidine compound, and an alkylaluminum compound; f) a chromium containing compound, an $N^2$-phosphinyl formamidine compound, an alkylaluminum compound; g) a chromium containing compound complexed to an $N^2$-phosphinyl formamidine compound, and an alkylaluminum compound; h) a chromium containing compound, an $N^2$-phosphinyl guanidine compound, and an alkylaluminum compound; i) a chromium containing compound complexed to an $N^2$-phosphinyl guanidine compound, and an alkylaluminum compound; and j) any combinations thereof.

Group B

A first embodiment, which is a composition comprising:
a) at least 76 mol % $C_{10}$ monoolefins, the $C_{10}$ monoolefins comprising i) at least 3 mol % 2-butyl-1-hexene, ii) at least 8 mol % 3-propyl-1-heptene, iii) at least 6 mol % 4-ethyl-1-octene, and iv) at least 20 mol % 5-methyl-1-nonene; and b) at least 1 mol % $C_{14}$ monoolefins.

A second embodiment, which is the composition of the first embodiment, wherein the $C_{10}$ monoolefins comprise i) from 3 mol % to 20 mol % 2-butyl-1-hexene, ii) from 10 mol % to 32 mol % 3-propyl-1-heptene, iii) from 7 mol % to 25 mol % 4-ethyl-1-octene, and iv) from 24 mol % to 52 mol % 5-methyl-1-nonene.

A third embodiment, which is the composition of any one of the first and the second embodiments, wherein the composition comprises a) from 76 mol % to 92 mol % $C_{10}$ monoolefins and b) from 1 mol % to 12 mol % $C_{14}$ monoolefins.

A fourth embodiment, which is the composition of any one of the first through the third embodiments further comprising from 0.1 mol % to 5 mol % $C_{12}$ monoolefins, the $C_{12}$ monoolefins comprising from 54 mol % to 74 mol % 1-dodecene.

A fifth embodiment, which is the composition of any one of the first through the fourth embodiments further comprising from 0.1 mol % to 5 mol % $C_8$ monoolefins, the $C_8$ monoolefins comprising at least 95 mol % 1-octene.

A sixth embodiment, which is the composition of any one of the first through the fifth embodiments further comprising from 0.05 mol % to 2 mol % $C_{16}$ monoolefins and/or $C_{18}$ monoolefins.

A seventh embodiment, which is the composition of any one of the first through the sixth embodiments further comprising from 0.2 mol % to 6 mol % acyclic saturated hydrocarbons.

An eighth embodiment, which is the composition of the seventh embodiment, wherein the acyclic saturated hydrocarbons comprise octane, decane, dodecane, tetradecane, or combinations thereof.

A ninth embodiment, which is the composition of any one of the first through the eighth embodiments, wherein the acyclic saturated hydrocarbons comprise a) from 10 mol % to 26 mol % octane, b) from 24 mol % to 48 mol % decane, c) from 22 mol % to 40 mol % dodecane, and d) from 7 mol % to 23 mol % tetradecane.

A tenth embodiment, which is the composition of any one of the first through the ninth embodiments further comprising from 1.9 mol % to 5.1 mol % cyclic saturated hydrocarbons.

An eleventh embodiment, which is the composition of the tenth embodiment, wherein the cyclic saturated hydrocarbon is methylcyclopentane, cyclohexane, methylcyclohexane, or combinations thereof.

A twelfth embodiment, which is the composition of any one of the first through the eleventh embodiments further comprising from 1 mol % to 3.4 mol % of a $C_6$ to $C_{12}$ aromatic hydrocarbon.

A thirteenth embodiment, which is the composition of the twelfth embodiment, wherein the aromatic hydrocarbon is benzene, toluene, ethylbenzene, xylene, mesitylene, hexamethylbenzene, or combinations thereof.

A fourteenth embodiment, which is the composition of any one of the first through the thirteenth embodiments further comprising from 0.4 mol % to 3 mol % of a $C_4$ to $C_{12}$ alcohol.

A fifteenth embodiment, which is the composition of the fourteenth embodiment, wherein the $C_4$ to $C_{12}$ alcohol is 1-hexanol, 2-hexanol, 3-hexanol, 2-ethyl-1-hexanol, 1-heptanol, 2-heptanol, 3-heptanol, 4-heptanol, 2-methyl-3-heptanol, 1-octanol, 2-octanol, 3-octanol, 4-octanol, 7-methyl-2-decanol, 1-decanol, 2-decanol, 3-decanol, 4-decanol, 5-decanol, 2-ethyl-1-decanol, or combinations thereof.

A sixteenth embodiment, which is a composition comprising at least 95 mol % $C_{10}$ monoolefins, the $C_{10}$ monoolefins comprising i) at least 3 mol % 2-butyl-1-hexene, ii) at least 10 mol % 3-propyl-1-heptene, iii) at least 7 mol % 4-ethyl-1-octene, and iv) at least 24 mol % 5-methyl-1-nonene.

A seventeenth embodiment, which is the composition of the sixteenth embodiment, wherein the composition comprises less than 3 mol % $C_{9-}$ hydrocarbons, and less than 3 mol % $C_{11+}$ hydrocarbons.

An eighteenth embodiment, which is the composition of any one of the sixteenth and the seventeenth embodiments, wherein the $C_{10}$ monoolefins comprise i) from 3 mol % to 20 mol % 2-butyl-1-hexene, ii) from 10 mol % to 32 mol % 3-propyl-1-heptene, iii) from 7 mol % to 25 mol % 4-ethyl-1-octene, and iv) from 24 mol % to 52 mol % 5-methyl-1-nonene.

A nineteenth embodiment, which is the composition of any one of the sixteenth through the eighteenth embodiments, wherein a molar ratio of 5-methyl-1-nonene to 2-butyl-1-hexene is at least 2:1.

A twentieth embodiment, which is the composition of any one of the sixteenth through the nineteenth embodiments, wherein a molar ratio of 5-methyl-1-nonene to 3-propyl-1-heptene is at least 1.2:1.

A twenty-first embodiment, which is the composition of any one of the sixteenth through the twentieth embodiments, wherein a molar ratio of 5-methyl-1-nonene to 4-ethyl-1-octene is at least 1.6:1.

A twenty-second embodiment, which is the composition of any one of the sixteenth through the twenty-first embodiments, wherein the $C_{10}$ monoolefins comprise from 1 mol % to 16 mol % 4-decene and/or 5-decene.

A twenty-third embodiment, which is the composition of any one of the sixteenth through the twenty-second embodiments, wherein the $C_{10}$ monoolefins comprise from 0.5 mol % to 9 mol % 1-decene.

A twenty-fourth embodiment, which is a process comprising: a) contacting 1) ethylene, 2) a catalyst system comprising i) a chromium containing compound, ii) a heteroatomic ligand, and iii) an alkylaluminum compound, and 3) optionally a reaction system diluent; b) forming an oligomer product comprising 1-hexene and/or 1-octene in a reaction system; c) discharging a reaction system effluent from the reaction system; d) contacting the reaction system effluent with a catalyst system deactivating agent; and e) isolating a first composition comprising: (1) at least 76 mol % $C_{10}$ monoolefins, the $C_{10}$ monoolefins comprising (i) at least 3 mol % 2-butyl-1-hexene, (ii) at least 8 mol % 3-propyl-1-heptene, (iii) at least 6 mol % 4-ethyl-1-octene, and (iv) at least 20 mol % 5-methyl-1-nonene, and (2) at least 1 mol % $C_{14}$ monoolefins.

A twenty-fifth embodiment, which is the process of the twenty-fourth embodiment further comprising recovering a second composition comprising 95 mol % $C_{10}$ monoolefins from the first composition, the $C_{10}$ monoolefins comprising (i) at least 3 mol % 2-butyl-1-hexene, (ii) at least 10 mol % 3-propyl-1-heptene, (iii) at least 7 mol % 4-ethyl-1-octene, and (iv) at least 24 mol % 5-methyl-1-nonene.

A twenty-sixth embodiment, which is process of any one of the twenty-fourth and the twenty-fifth embodiments, wherein the catalyst system is prepared in a catalyst system solvent.

A twenty-seventh embodiment, which is the process of any one of the twenty-fourth through the twenty-sixth embodiments, wherein the reaction system effluent comprises the oligomer product comprising at least 60 mol % 1-hexene and/or 1-octene, the catalyst system, and the optional reaction system diluent.

A twenty-eighth embodiment, which is the process of any one of the twenty-fourth through the twenty-seventh embodiments, wherein the process further comprises isolating a stream comprising (a) at least 90 mol % 1-hexene, (b) at least 90 mol % 1-octene, or (c) at least 90 mol % 1-hexene and 1-octene.

A twenty-ninth embodiment, which is the process of any one of the twenty-fourth through the twenty-eighth embodiments, wherein the heteroatomic ligand is a pyrrole compound, a diphosphino aminyl compound, an $N^2$-phosphinyl amidine compound, an $N^2$-phosphinyl formamidine compound, an $N^2$-phosphinyl guanidine compound, or combinations thereof.

A thirtieth embodiment, which is the process of any one of the twenty-fourth through the twenty-ninth embodiments, wherein the catalyst system is selected from the group consisting of: a) a chromium containing compound, a pyrrole compound, an alkylaluminum compound, and optionally a halide containing compound; b) a chromium containing compound, a diphosphino aminyl compound, an alkylaluminum compound; c) a chromium containing compound complexed to a diphosphino aminyl compound, and an alkylaluminum compound; d) a chromium containing compound, an $N^2$-phosphinyl amidine compound, and an alkylaluminum compound; e) a chromium containing compound complexed to an $N^2$-phosphinyl amidine compound, and an alkylaluminum compound; f) a chromium containing compound, an $N^2$-phosphinyl formamidine compound, an alkylaluminum compound; g) a chromium containing compound complexed to an $N^2$-phosphinyl formamidine compound, and an alkylaluminum compound; h) a chromium containing compound, an $N^2$-phosphinyl guanidine compound, and an alkylaluminum compound; i) a chromium containing compound complexed to an $N^2$-phosphinyl guanidine compound, and an alkylaluminum compound; and j) any combinations thereof.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent . . . 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A composition comprising: a) at least 76 mol % $C_{10}$ monoolefins, the $C_{10}$ monoolefins comprising i) at least 3 mol % 2-butyl-1-hexene, ii) at least 8 mol % 3-propyl-1-heptene, iii) at least 6 mol % 4-ethyl-1-octene, and iv) at least 20 mol % 5-methyl-1-nonene; and b) at least 1 mol % $C_{14}$ monoolefins.

2. The composition of claim 1, wherein the $C_{10}$ monoolefins comprise i) from 3 mol % to 20 mol % 2-butyl-1-hexene, ii) from 10 mol % to 32 mol % 3-propyl-1-heptene, iii) from 7 mol % to 25 mol % 4-ethyl-1-octene, and iv) from 24 mol % to 52 mol % 5-methyl-1-nonene.

3. The composition of claim 1, wherein the composition comprises a) from 76 mol % to 92 mol % $C_{10}$ monoolefins and b) from 1 mol % to 12 mol % $C_{14}$ monoolefins.

4. The composition of claim 1, wherein the composition comprises a) from 0.1 mol % to 5 mol % $C_{12}$ monoolefins, the $C_{12}$ monoolefins comprising from 54 mol % to 74 mol % 1-dodecene, b) from 0.1 mol % to 5 mol % $C_8$ monoolefins, the $C_8$ monoolefins comprising at least 95 mol % 1-octene or c) from 0.05 mol % to 2 mol % $C_{16}$ monoolefins and/or $C_{18}$ monoolefins.

5. The composition of claim 1, further comprising from 0.2 mol % to 6 mol % acyclic saturated hydrocarbons.

6. The composition of claim 4, wherein the acyclic saturated hydrocarbons comprise a) from 10 mol % to 26 mol % octane, b) from 24 mol % to 48 mol % decane, c) from 22 mol % to 40 mol % dodecane, and d) from 7 mol % to 23 mol % tetradecane.

7. The composition of claim 1, further comprising from 1.9 mol % to 5.1 mol % cyclic saturated hydrocarbons, from 1 mol % to 3.4 mol % of a $C_6$ to $C_{12}$ aromatic hydrocarbon, or from 0.4 mol % to 3 mol % of a $C_4$ to $C_{12}$ alcohol.

8. A composition comprising at least 95 mol % $C_{10}$ monoolefins, the $C_{10}$ monoolefins comprising i) at least 3 mol % 2-butyl-1-hexene, ii) at least 10 mol % 3-propyl-1-heptene, iii) at least 7 mol % 4-ethyl-1-octene, and iv) at least 24 mol % 5-methyl-1-nonene.

9. The composition of claim 8, wherein the composition comprises less than 3 mol % $C_{9-}$ hydrocarbons, and less than 3 mol % $C_{11+}$ hydrocarbons.

10. The composition of claim 8, wherein the $C_{10}$ monoolefins comprise i) from 3 mol % to 20 mol % 2-butyl-1-hexene, ii) from 10 mol % to 32 mol % 3-propyl-1-heptene, iii) from 7 mol % to 25 mol % 4-ethyl-1-octene, and iv) from 24 mol % to 52 mol % 5-methyl-1-nonene.

11. The composition of claim 8, wherein a molar ratio of 5-methyl-1-nonene to 2-butyl-1-hexene is at least 2:1, a molar ratio of 5-methyl-1-nonene to 3-propyl-1-heptene is at least 1.2:1, or a molar ratio of 5-methyl-1-nonene to 4-ethyl-1-octene is at least 1.6:1.

12. The composition of claim 8, wherein the $C_{10}$ monoolefins comprise from 1 mol % to 16 mol % 4-decene and/or 5-decene.

13. The composition of claim 8, wherein the $C_{10}$ monoolefins comprise from 0.5 mol % to 9 mol % 1-decene.

14. A process comprising: a) contacting 1) ethylene, 2) a catalyst system comprising i) a chromium containing compound, ii) a heteroatomic ligand, and iii) an alkylaluminum compound, and 3) optionally a reaction system diluent; b) forming an oligomer product comprising 1-hexene and/or 1-octene in a reaction system; c) discharging a reaction system effluent from the reaction system; d) contacting the reaction system effluent with a catalyst system deactivating agent; and e) isolating a first composition comprising: (1) at least 76 mol % $C_{10}$ monoolefins, the $C_{10}$ monoolefins comprising (i) at least 3 mol % 2-butyl-1-hexene, (ii) at least 8 mol % 3-propyl-1-heptene, (iii) at least 6 mol % 4-ethyl-1-octene, and (iv) at least 20 mol % 5-methyl-1-nonene, and (2) at least 1 mol % $C_{14}$ monoolefins.

15. The process of claim 14, the process further comprising recovering a second composition comprising 95 mol % $C_{10}$ monoolefins from the first composition, the $C_{10}$ monoolefins comprising (i) at least 3 mol % 2-butyl-1-hexene, (ii) at least 10 mol % 3-propyl-1-heptene, (iii) at least 7 mol % 4-ethyl-1-octene, and (iv) at least 24 mol % 5-methyl-1-nonene.

16. The process of claim 14, wherein the catalyst system is prepared in a catalyst system solvent.

17. The process of claim 14, wherein the reaction system effluent comprises the oligomer product comprising at least 60 mol % 1-hexene and/or 1-octene, the catalyst system, and the optional reaction system diluent.

18. The process of claim 14, wherein the process further comprises isolating a stream comprising (a) at least 90 mol % 1-hexene, (b) at least 90 mol % 1-octene, or (c) at least 90 mol % 1-hexene and 1-octene.

19. The process of claim 14, wherein the heteroatomic ligand is a pyrrole compound, a diphosphino aminyl compound, an $N^2$-phosphinyl amidine compound, an $N^2$-phosphinyl formamidine compound, an $N^2$-phosphinyl guanidine compound, or combinations thereof.

20. The process of claim 14, wherein the catalyst system is selected from the group consisting of: a) a chromium containing compound, a pyrrole compound, an alkylaluminum compound, and optionally a halide containing compound; b) a chromium containing compound, a diphosphino aminyl compound, an alkylaluminum compound; c) a chromium containing compound complexed to a diphosphino aminyl compound, and an alkylaluminum compound; d) a chromium containing compound, an $N^2$-phosphinyl amidine compound, and an alkylaluminum compound; e) a chromium containing compound complexed to an $N^2$-phosphinyl amidine compound, and an alkylaluminum compound; f) a chromium containing compound, an $N^2$-phosphinyl formamidine compound, an alkylaluminum compound; g) a chromium containing compound complexed to an $N^2$-phosphinyl formamidine compound, and an alkylaluminum compound; h) a chromium containing compound, an $N^2$-phosphinyl guanidine compound, and an alkylaluminum compound; i) a chromium containing compound complexed to an $N^2$-phosphinyl guanidine compound, and an alkylaluminum compound; and j) any combinations thereof.

* * * * *